US009096638B2

(12) United States Patent
Paquette et al.

(10) Patent No.: US 9,096,638 B2

(45) Date of Patent: Aug. 4, 2015

(54) **DETECTION OF TOXIGENIC STRAINS OF *CLOSTRIDIUM DIFFICILE***

(75) Inventors: Nancy Paquette, Quebec (CA); Marie-Eve Rochette, Quebec (CA); Rachel Labourdette, Quebec (CA)

(73) Assignee: GENEOHM SCIENCES CANADA, INC., Quebec (CA)

( * ) Notice: Subject to any disclaimer, the term of this patent is extended or adjusted under 35 U.S.C. 154(b) by 876 days.

(21) Appl. No.: 12/203,694

(22) Filed: Sep. 3, 2008

(65) Prior Publication Data

US 2009/0208948 A1 Aug. 20, 2009

Related U.S. Application Data

(60) Provisional application No. 60/970,492, filed on Sep. 6, 2007.

(51) Int. Cl.

*C12Q 1/68* (2006.01)
*C07H 21/00* (2006.01)
*C07H 21/04* (2006.01)

(52) U.S. Cl.

CPC ................ *C07H 21/04* (2013.01); *C07H 21/00* (2013.01); *C12Q 1/689* (2013.01); *C12Q 2561/101* (2013.01); *C12Q 2561/113* (2013.01)

(58) Field of Classification Search

None

See application file for complete search history.

(56) References Cited

U.S. PATENT DOCUMENTS 8,114,601 B2 * 2/2012 Bergeron et al. ............ 435/6.12

FOREIGN PATENT DOCUMENTS

JP 2006333785 12/2006
WO WO 2008/041354 4/2008

OTHER PUBLICATIONS

GenBank Accession No. X53138, Barroso et al, "*Clostridium difficile* toxB gene for toxin B," Apr. 2005.*

GenBank Accession No. AJ011301, Kohl, "*Clostridium difficile* (strain 8864) pathogenicity DNA locus,"Jan. 2001.*

GenBank Accession No. Z23277, von Eichel-Streiber et al, "*C. difficile* gene for toxin B," Apr. 2005.*

Plant-Microbe Genomics Facility (PMGF) at the Ohio State University, "Procedures and Recommendations for Quantitative PCR," version 1.2, Apr. 2003.*

Abed, Y. et al. World Journal of Microbiology & Biotechnology 11(5):478-480 (Sep. 1995).*

Belanger, S.D. et al. Rapid detection of *Clostridium difficile* in Feces by RealTime PCR. Journal of Clinical Microbiology. Feb. 2003, vol. 41, No. 2, pp. 730-734, ISSN 0095-1137.

Van Den Berg, RJ. et al. Rapid diagnosis of toxinogenic *Clostridium difficile* in faecal samples with internally controlled real-time PCR. Clinical Microbiology and Infection. Feb. 2006, vol. 12, No. 2, pp. 184-186, ISSN 1198-743X.

(Continued)

*Primary Examiner* — Diana B Johannsen

(74) *Attorney, Agent, or Firm* — Knobbe, Martens, Olson & Bear LLP

(57) ABSTRACT

Primers and probes for detection of toxin-producing (toxigenic) strains of *Clostridium difficile*, and to methods of detecting toxigenic strains using these primers and probes. Toxigenic strains of *C. difficile* are detected by nucleic acid-based amplification methods using particular primers and probes that bind to the toxin B (TcdB) gene. These primers and probes are used to amplify *C. difficile* nucleic acids in clinical samples to determine the presence of these toxigenic strains.

15 Claims, 3 Drawing Sheets

(56) References Cited

OTHER PUBLICATIONS

Lemee, L. et al. Multiplex PCR Targeting tpi (Triose Phosphate Isomerase), tcdA (Toxin A), and tcdB (Toxin B) Genes for Toxigenic Culture of *Clostridium difficile*. Journal of Clinical Microbiology. Dec. 2004, vol. 42, No. 12, pp. 5710-5714, ISSN 0095-1137.
Alonso, R. et al. Toxigenic status of *Clostridium difficile* in a large Spanish teaching hospital. Journal of Medical Microbiology. Feb. 2005, vol. 54, Pt. 2, pp. 159-162, ISSN 0022-2615.
Peterson, L.R. et al. Detection of Toxigenic *Clostridium difficile* in Stool Samples by Real-Time PCR for the Diagnosis of *C. difficile*-Associated Diarrhea. Clinical Infectious Diseases. Nov. 2007, vol. 45, No. 9, pp. 1152-1160, ISSN 1058-4838.
International Search Report issued on the corresponding PCT Application No. PCT/CA2008/001564, dated Dec. 22, 2008.
Goh, S., "Phenotypic and genotypic characterization of bacteriophages of *Clostridium difficile*" Ph.D. Thesis, Australia 2003, Retrieved from the Internet: URL: http://repository.uwa.edu.au/R/HLA2PK2H6KQRBNYXHMVPX6SMK9VYYXL4EPFXAA DV73KE3NXALT-01439?func_results-full, retrieved on Mar. 23, 2011.
Kato, et al., "Identification A-negative, toxin B-positive *Clostridium difficile* by PCT" *J. Clin. Microbio*. (1998) 36: 2178-2182.
Lee, et al., "LuxS/autoinducer-2 quorum sensing molecule regulates transcriptional virulence gene expression in *Clostridium difficile" Biochem and Biophysical Res Comm*. (2005) 335: 659-666.
Ott, et al., "Quantification of intestinal bacterial populations by real-time PCR with a universal primer set and minor groove binder probes: a global approach to the enteric flora" *J. Clin. Microbio*. (2004) 42: 2566-2572.
European Search Report, dated Mar. 23, 2011, issued in European patent application No. 08800272.
Extended European Search Report, dated May 20, 2011, issued in European patent application No. 08800272.
Summons to attend oral proceedings dated Sep. 19, 2013 for European Application No. 08800272.0.
Goh et al., Effect of phage infection on toxin production by *Clostridium difficile*; J. Med. Microbiol., Feb. 2005; 54: 129-135.
Office Action dated Jul. 2, 2013 of Japanese Application No. 2010-523247, filed Sep. 5, 2008.
Chaves-Olarte et al., A Novel Cytotoxin from *Clostridium difficile* Serogroup F is a Functional Hybrid between Two Other Large Clostridial Cytotoxins., J Biol Chem. (1999) 274(16): 1146-1152.
Cohen et al., Isolation of a Toxin B-deficient Mutant Strain of *Clostridium difficile* in a Case of Recurrent *C. difficile*-associated Diarrhea., Clin Infect Dis. (1998) 26(2): 410-412.
Cohen et al., Analysis of the Pathogenicity Locus in *Clostridium difficile* Strains., J Infect Dis. (2000) 181(2): 659-663.
Drudy et al., Toxin A-negative, Toxin B-positive *Clostridium difficile*., Int J Infect Dis. (2007) 11(1): 510.
Geric et al., Frequency of Binary Toxin Genes among *Clostridium difficile* Strains that do not Produce Large Clostridial Toxins., J Clin Microbiol. (2003) 41(11): 5227-5232.
Geric et al., Distribution of *Clostridium difficile* Variant Toxinotypes and Strains with Binary Toxin Genes among Clinical Isolates in an American Hospital., J Med Microbiol. (2004) 53(Pt9): 887-894.
Geric Stare et al., Variant Forms of the Binary Toxin CDT Locus and tcdC Gene in *Clostridium difficile* Strains., J Med Microbiol. (2007) 56(Pt 3): 329-335.
Kato et al., Identification of Toxin A-negative, Toxin B-positive *Clostridium difficile* by PCR., J Clin Microbiol. (1998) 36(8): 2178-2182.
Knoop et al., *Clostridium difficile*: Clinical Disease and Diagnosis., Clin Microbiol. Rev. (1993) 6(3): 251-265.
Kuijper et al., Emergence of *Clostridium difficile*-associated disease in North America and Europe., Clin Micro Infect., (2006) 12(supp6): 2-18.
MacCannell et al., Characterization of a Novel, TcdB-deficient, NPA1 Variant Strain of *Clostridium difficile*., ICAAC 2006; University of Calgary, Canada, Faculty of Medicine; p. 1 [Abstract].
McDonald et al., An Epidemic, Toxin Gene-variant Strain of *Clostridium difficile*., N Engl J Med. (2005) 353(23): 2433-2441.
Mehlig et al., Variant toxin B and a functional toxin a produced by *Clostridium difficile* C34., FEMS Microbiol. Lett. (2001) 198(2): 171-176.
Rupnik et al., Characterization of polymorphisms in the toxin A and B genes of *Clostridium difficile*., FEMS Microbiol Lett. (1997) 148(2): 197-202.
Rupnik et al., A novel Toxinotyping Scheme and Correlation of Toxinotypes with Serogroups of *Clostridium difficile* Isolates. J Clin Microbiol (1998) 36(8): 2240-2247.
Rupnik et al., Comparison of Toxinotyping and PCR Ribotyping of *Clostridium difficile* Strains and Dexcription of Novel Toxinotypes., Microbiology (2001) 147(Pt1): 439-447.
Rupnik et al., New types of Toxin A-negative, Toxin B-positive Strains among *Clostridium difficile* Isolates from Asia., J Clin Microbiol. (2003) 41(3): 1118-1125.
Rupnik et al., Revised nomenclature of *Clostridium difficile* toxins and associated genes., J Med Microbiol. (2005) 54: 113-117.
Van Den Berg et al., Rapid Diagnosis of Toxinogenic *Clostridium difficile* in Faecal Samples with Internally Controlled Real-time PCR. Clin Microbiol Infect. (2006) 12(2): 184-186.
Von Eichel-Streiber et al., Comparative sequence analysis of the *Clostridium difficile* toxins A and B., Mol Gen Genet. (1992) 233(1-2): 260-268.
Von Eichel-Streiber et al., Closing in on the toxic domain through analysis of a variant *Clostridium difficile* cytotoxin B., Mol Microbiol. (1995) 17(2): 313-321.
Voth et al., *Clostridium difficile* Toxins: Mechanism of Action and Role in Disease., Clin. Microbiol. Rev. (2005) 18(2): 247-263.
International Preliminary Report on Patentability and Written Opinion dated Mar. 9, 2010 for PCT/CA2008/001564, filed Sep. 5, 2008.
Examination Report dated Jun. 21, 2013 in Australian Patent Application No. 2008295396, filed Sep. 5, 2008.
Australian Examination Report dated Dec. 11, 2014 in Application No. 2008295396, filed Sep. 5, 2008.

* cited by examiner

5' -(FAM) CGG TTG TTG AAT TAG TAT CAA CTG CAC AAC CG (Dabcyl)- 3'

ΔG -4.33 kcal.mole- 1 (synthesis conditions)
ΔG -0.74 kcal.mole- 1 (PCR conditions)

5' -(TET) CGG GCG ATG CCT CTT CAC ATT GCT CCA CCT TTC CTC GCC GG (Dabcyl)- 3'

ΔG -5.84 kcal.mole- 1 (synthesis conditions)
ΔG -1.83 kcal.mole- 1 (PCR conditions)

SEQUENCE LISTING

<160> NUMBER OF SEQ ID NOS: 33

<210> SEQ ID NO 1
<211> LENGTH: 7110
<212> TYPE: DNA
<213> ORGANISM: Clostridium difficile

<400> SEQUENCE: 1
attttatgag tttagttaat agaaaacagt tagaaaaaat ggcaaatgta agatttcgta 60
ctcaagaaga tgaatatgtt gcaatattgg atgctttaga agaatatcat aatatgtcag 120
agaatactgt agtcgaaaaa tatttaaaat taaaagatat aaatagttta acagatattt 180
atatagatac atataaaaaa tctggtagaa ataaagcctt aaaaaaattt aaggaatatc 240
tagttacaga agtattagag ctaaagaata ataatttaac tccagttgag aaaaatttac 300
attttgtttg gattggaggt caaataaatg acactgctat taattatata aatcaatgga 360
aagatgtaaa tagtgattat aatgttaatg tttttatga tagtaatgca tttttgataa 420
acacattgaa aaaaactgta gtagaatcag caataaatga tacacttgaa tcatttagag 480
aaaacttaaa tgaccctaga tttgactata ataaattctt cagaaaacgt atggaaataa 540
tttatgataa acagaaaaat ttcataaact actataaagc tcaaagagaa gaaaatcctg 600
aacttataat tgatgatatt gtaaagacat atctttcaaa tgagtattca aaggagatag 660
atgaacttaa tacctatatt gaagaatcct taaataaaat tacacagaat agtggaaatg 720
atgttagaaa ctttgaagaa tttaaaaatg gagagtcatt caacttatat gaacaagagt 780
tggtagaaag gtggaattta gctgctgctt ctgaagtcta tagagaaacc tagttcagta 840
acagtggatt tttgggaaat gacaaagtta gaagctataa tgaaatacaa agaatatata 900
ccagaatata cctccatatt aagaatatct gcattaaaag aaattggtgg tatgtattta 960
gatgttgata tgttaccagg aatacaacca gacttatttg agaacatttt gacatgttag 1020
acgaagaagt tcaaagtagt tttgaatctg ttctagcttc taagtcagat aaatcagaaa 1080
tattctcatc acttggtgat atggaggcat caccactaga agttaaaatt gcatttaata 1140
gtaagggtat tataaatcaa gggctaattt ctgtgaaaga ctcatattgt agcaatttaa 1200
tagtaaaaca aatcgagaat agatataaaa tattgaataa tagtttaaat ccagctatta 1260
gcgaggataa tgattttaat actacaacga atacctttat tgatagtata atggctgaag 1320
ctaatgcaga taatggtaga tttatgatgg aactaggaaa gtatttaaga gttggtttct 1380
tcccagatgt taaaactact attaacttaa gtggccctga agcatatgcg gcagcttatc 1440
aagatttatt aatgtttaaa gaaggcagta tgaatatcca tttgatagaa gctgatttaa 1500
gaaactttga aatctctaaa actaatattt ctcaatcaac tgaacaagaa atggctagct 1560
tatggtcatt tgacgatgca agagctaaag ctcaatttga agaatataaa aggaattatt 1620
ttgaaggttc tcttggtgaa gatgataatc ttgatttttc tcaaaatata gtagttgaca 1680
aggagtatct tttagaaaaa atatcttcat tagcaagaag ttcagagaga ggatatatac 1740
actatattgt tcagttacaa ggagataaaa ttagttatga agcagcatgt aacttatttg 1800
caaagactcc ttatgatagt gtactgtttc agaaaaatat agaagattca gaaattgcat 1860
attattataa tcctggagat ggtgaaatac aagaaataga caagtataaa attccaagta 1920
taatttctga tagacctaag attaaattaa catttattgg tcatggtaaa gatgaattta 1980
atactgatat atttgcaggt tttgatgtag attcattatc cacagaaata gaagcagcaa 2040
tagatttagc taaagaggat atttctccta agtcaataga aataaattta ttaggatgta 2100

-continued

```
atatgtttag ctactctatc aacgtagagg agacttatcc tggaaaatta ttacttaaag   2160
ttaaagataa aatatcagaa ttaatgccat ctataagtca agactctatt atagtaagtg   2220
caaatcaata tgaagttaga ataaatagtg aaggaagaag agaattattg gatcattctg   2280
gtgaatggat aaataaagaa gaaagtatta taaaggatat ttcatcaaaa gaatatatat   2340
catttaatcc taaagaaaat aaaattacag taaaatctaa aaatttacct gagctatcta   2400
cattattaca agaaattaga aataattcta attcaagtga tattgaacta gaagaaaaag   2460
taatgttaac agaatgtgag ataaatgtta tttcaaatat agatacgcaa attgttgagg   2520
aaaggattga agaagctaag aatttaactt ctgactctat taattatata aaagatgaat   2580
ttaaactaat agaatctatt tctgatgcac tatgtgactt aaaacaacag aatgaattag   2640
aagattctca ttttatatct tttgaggaca tatcagagac tgatgaggga tttagtataa   2700
gatttattaa taaagaaact ggagaatcta tatttgtaga aactgaaaaa acaatattct   2760
ctgaatatgc taatcatata actgaagaga tttctaagat aaaaggtact atatttgata   2820
ctgtaaatgg taagttagta aaaaaagtaa atttagatac tacacacgaa gtaaatactt   2880
taaatgctgc atttttata caatcattaa tagaatataa tagttctaaa gaatctctta   2940
gtaatttaag tgtagcaatg aaagtccaag tttacgctca attatttagt actggtttaa   3000
atactattac agatgcagcc aaagttgttg aattagtatc aactgcatta gatgaaacta   3060
tagacttact tcctacatta tctgaaggat tacctataat tgcaactatt atagatggtg   3120
taagtttagg tgcagcaatc aaagagctaa gtgaaacgag tgacccatta ttaagacaag   3180
aaatagaagc taagataggt ataatggcag taaatttaac aacagctaca actgcaatca   3240
ttacttcatc tttggggata gctagtggat ttagtatact tttagttcct ttagcaggaa   3300
tttcagcagg tataccaagc ttagtaaaca atgaacttgt acttcgagat aaggcaacaa   3360
aggttgtaga ttattttaaa catgtttcat tagttgaaac tgaaggagta tttactttat   3420
tagatgataa aataatgatg ccacaagatg atttagtgat atcagaaata gattttaata   3480
ataattcaat agttttaggt aaatgtgaaa tctggagaat ggaaggtggt tcaggtcata   3540
ctgtaactga tgatatagat cacttctttt cagcaccatc aataacatat agagagccac   3600
acttatctat atatgacgta ttggaagtac aaaaagaaga acttgatttg tcaaaagatt   3660
taatggtatt acctaatgct ccaaatagag tatttgcttg ggaaacagga tggacaccag   3720
gtttaagaag cttagaaaat gatggcacaa aactgttaga ccgtataaga gataactatg   3780
aaggtgagtt ttattggaga tattttgctt ttatagctga tgctttaata acaacattaa   3840
aaccaagata tgaagatact aatataagaa taaatttaga tagtaatact agaagtttta   3900
tagttccaat aataactaca gaatatataa gagaaaaatt atcatattct ttctatggtt   3960
caggaggaac ttatgcattg tctctttctc aatataatat gggtataaat atagaattaa   4020
gtgaaagtga tgtttggatt atagatgttg ataatgttgt gagagatgta actatagaat   4080
ctgataaaat taaaaaaggt gatttaatag aaggtatttt atctacacta agtattgaag   4140
agaataaaat tatcttaaat agccatgaga ttaatttttc tggtgaggta aatggaagta   4200
atggatttgt ttctttaaca ttttcaattt tagaaggaat aaatgcaatt atagaagttg   4260
atttattatc taaatcatat aaattactta tttctggcga attaaaaata ttgatgttaa   4320
attcaaatca tattcaacag aaaatagatt atataggatt caatagcgaa ttacagaaaa   4380
atataccata tagctttgta gatagtgaag gaaaagagaa tggttttatt aatggttcaa   4440
```

-continued

```
caaaagaagg tttatttgta tctgaattac ctgatgtagt tcttataagt aaggtttata   4500
tggatgatag taagccttca tttggatatt atagtaataa tttgaaagat gtcaaagtta   4560
taactaaaga taatgttaat atattaacag gttattatct taaggatgat ataaaaatct   4620
ctctttcttt gactctacaa gatgaaaaaa ctataaagtt aaatagtgtg catttagatg   4680
aaagtggagt agctgagatt ttgaagttca tgaatagaaa aggtaataca aatacttcag   4740
attctttaat gagcttttta gaaagtatga atataaaaag tattttcgtt aatttcttac   4800
aatctaatat taagtttata ttagatgcta attttataat aagtggtact acttctattg   4860
gccaatttga gtttatttgt gatgaaaatg ataatataca accatatttc attaagttta   4920
atacactaga aactaattat actttatatg taggaaatag acaaaatatg atagtggaac   4980
caaattatga tttagatgat tctggagata tatcttcaac tgttatcaat ttctctcaaa   5040
agtatcttta tggaatagac agttgtgtta ataaagttgt aatttcacca aatatttata   5100
cagatgaaat aaatataacg cctgtatatg aaacaaataa tacttatcca gaagttattg   5160
tattagatgc aaattatata aatgaaaaaa taaatgttaa tatcaatgat ctatctatac   5220
gatatgtatg gagtaatgat ggtaatgatt ttattcttat gtcaactagt gaagaaaata   5280
aggtgtcaca agttaaaata agattcgtta atgtttttaa agataagact ttggcaaata   5340
agctatcttt taactttagt gataaacaag atgtacctgt aagtgaaata atcttatcat   5400
ttacaccttc atattatgag gatggattga ttggctatga tttgggtcta gtttctttat   5460
ataatgagaa attttatatt aataactttg gaatgatggt atctggatta atatatatta   5520
atgattcatt atattatttt aaaccaccag taaataattt gataactgga tttgtgactg   5580
taggcgatga taaatactac tttaatccaa ttaatggtgg agctgcttca attggagaga   5640
caataattga tgacaaaaat tattatttca accaaagtgg agtgttacaa acaggtgtat   5700
ttagtacaga agatggattt aaatattttg ccccagctaa tacacttgat gaaaacctag   5760
aaggagaagc aattgatttt actggaaaat taattattga cgaaaatatt tattattttg   5820
atgataatta tagaggagct gtagaatgga aagaattaga tggtgaaatg cactatttta   5880
gcccagaaac aggtaaagct tttaaaggtc taaatcaaat aggtgattat aaatactatt   5940
tcaattctga tggagttatg caaaaaggat ttgttagtat aaatgataat aaacactatt   6000
ttgatgattc tggtgttatg aaagtaggtt acactgaaat agatggcaag catttctact   6060
ttgctgaaaa cggagaaatg caaataggag tatttaatac agaagatgga tttaaatatt   6120
ttgctcatca taatgaagat ttaggaaatg aagaaggtga agaaatctca tattctggta   6180
tattaaattt caataataaa atttactatt ttgatgattc atttacagct gtagttggat   6240
ggaaagattt agaggatggt tcaaagtatt attttgatga agatacagca gaagcatata   6300
taggtttgtc attaataaat gatggtcaat attattttaa tgatgatgga attatgcaag   6360
ttggatttgt cactataaat gataaagtct tctacttctc tgactctgga attatagaat   6420
ctggagtaca aaacatagat gacaattatt tctatataga tgataatggt atagttcaaa   6480
ttggtgtatt tgatacttca gatggatata aatattttgc acctgctaat actgtaaatg   6540
ataatattta cggacaagca gttgaatata gtggtttagt tagagttggg gaagatgtat   6600
attattttgg agaaacatat acaattgaga ctggatggat atatgatatg gaaaatgaaa   6660
gtgataaata ttatttcaat ccagaaacta aaaaagcatg caaaggtatt aatttaattg   6720
atgatataaa atattatttt gatgagaagg gcataatgag aacgggtctt atatcatttg   6780
aaaataataa ttattacttt aatgagaatg gtgaaatgca atttggttat ataaatatag   6840
```

```
aagataagat gttctatttt ggtgaagatg gtgtcatgca gattggagta tttaatacac   6900

cagatggatt taaatacttt gcacatcaaa atactttgga tgagaatttt gagggagaat   6960

caataaacta tactggttgg ttagatttag atgaaaagag atattatttt acagatgaat   7020

atattgcagc aactggttca gttattattg atggtgagga gtattatttt gatcctgata   7080

cagctcaatt agtgattagt gaatagataa                                    7110
```

<210> SEQ ID NO 2
<211> LENGTH: 7013
<212> TYPE: DNA
<213> ORGANISM: Clostridium difficile

<400> SEQUENCE: 2

```
atgagtttag ttaatagaaa acagttagaa aaaatggcaa atgtaagatt tcgtgttcag     60

gaagatgaat atgtagcaat attagatgca ttagaagaat atcataatat gtcagaaaat    120

actgtagttg aaaagtatct aaaattaaaa gatataaaca gtttaacaga tacttatata    180

gatacatata aaaaatctgg tcgaaataaa gccttaaaaa aatttaaaga gtacttagtt    240

atagagatat tagaattaga agaatagcaa tttaactcca gtcgagaaaa atttacattt    300

tatatggatt ggagggcaaa taaatgatac tgctattaat tatataaatc aatggaaaga    360

tgtaaatagt gactataatg ttaatgtttt ttatgatagt aatgcatttt aaccacactg    420

caattttcag aaaacgtatg caaataactt atgataaaca gcaaaatttc ataaattact    480

ataaagctca aaaagaagaa aatcctgttt tgataaacac attgaaaaaa actataatag    540

aatcagcatc aaatgatacc cttgaatcat ttagagaaaa tttaaatgat cctgaaacct    600

tataattgat gatattgtaa agacatatct ttcaaacgag tattcaaagg atatagatga    660

acttaatgct tatattgaag agtcattaaa caaagtcaca gaaaatagtg gaaatgatgt    720

tagaaacttt gaagaattta aaactggaga agtattcaat ttatatgaac aagagttagt    780

agaaagatgg aatcttgctg gtgcatctga tatattaaga gtcgctatat tgaaaaatat    840

tggtggagtc tatctagatg ttgatatgtt accaggaata cacccagatt tatttaaaga    900

tataaataag cctgattcag taaagacagc tgtagatttg ggaagagatg cagttagaag    960

ccataatgaa acataaagaa tatataccag aatatacttc gaaacatttt gatacattgg   1020

atgaagaagt tcaaagtagc tttgaatctg ttttagcttc taagtctgat aagtcagaaa   1080

tatttttacc actaggagat atagaggtat cacctttaga agtaaaaatt gcatttgcca   1140

aaggttctat tataaatcaa gctctaattt ctgcaaaaga ttcatattgt agtgacttac   1200

taataaaaca aatccaaaac agatataaga tactgaatga tactttaggt ccagctatta   1260

gtcaaggtaa tgattttaat actacaatga acaattttgg tgaaagtttg ggagctatag   1320

ctaatgaaga gaatataagt tttatagcaa aaatcggaag ttatttaagg gttggatttt   1380

atcctgaagc taatactaca gttactttaa gtggtcctac aatatatgca ggagcttata   1440

aagatttatt aacatttaaa gagatgagca atagatactt ctatattgtc gatctgagtt   1500

aagaaatttt gaatttccta aggttaatat atctcaagca acagaacaag agaaaaatag   1560

tttatggcaa tttaatgaag aaagagctaa aattcaattt gaagaataca agaaaaatta   1620

ttttgaaggt gcacttggag aagatgataa tcttgatttt tctcaaaata cagtaactga   1680

caaagaatat cttttagaaa agatctcttc atcaacgaag aagttcagaa agaggatatg   1740

ttcattatat tgttcaatta caaggagata aaattagcta tgaagcagca tgtaacttat   1800
```

ttgcaaaaaa tccttatgac agtatactat ttcaaaaaaa tatagaagat tcagaagtag 1860
catattacta taatcctaca gatagtgaaa tacaagaaat tgataagtat agaattcctg 1920
atagaatctc tgatagacct aagattaaat taacattcat tggtcatggc aaagctgaat 1980
ttaatactga tatatttgca ggtcttgatg tagattcatt atcttcagaa atagaaacag 2040
caataggttt agccaaagag gatatttctc ctaaatctat agaaataaac ttactgggat 2100
gtaacatgtt tagctattct gtaaatgtag aagagactta tcctgggaaa ttattactta 2160
gagttaaaga taaagtatca gaattaatgc catctatgag tcaagactct attatagtaa 2220
gtgcaaatca atatgaagtt agaataaata gtgaaggaag aagagaatta ttagaccatt 2280
ctggtgaatg gataaacaaa gaagaaagta ttataaagga tatttcatca aaagaatata 2340
tatcatttaa tcctaaagag aataaagtta tagtaaaatc taaaaattta cctgaattat 2400
ctacattatt acaagaaatt agaaataatt ctaattcaag tgatattgaa ctagaagaaa 2460
aagtaatgtt agcagaatgt gagataaatg ttatttcaaa tatagagaca caagtggtag 2520
aagaaagaat tgaagaagct aaaagcttaa cttctgactc tattaattat ataaagaatg 2580
aatttaaact aatagaatct atttctgatg cactatgtga cttaaaacaa cagaatgaat 2640
tagaagattc tcattttata tcttttgagg acatatcaga gactgatgag ggtttagta 2700 taagatttat taataaagaa actggagaat ctatatttgt agaaactgaa aaaacaatat 2760
tctctgaata tgctaatcat ataactgaag agatttctaa gataaaaggt actatatttg 2820
atactgtaaa tggtaagtta gtaaaaaaag taaatttaga tactacacac gaagtaaata 2880
ctttaaatgc tgcatttttt atacaatcat taatagaata taatagttct aaagaatctc 2940
ttagtaattt aagtgtagca atgaaagttc aagtttacgc tcaattattt agtactggtt 3000
taaatactat tacagatgca gccagagttg ttgaattagt atcaactgca ttagatgaaa 3060
ctatagactt acttcctaca ttatctgaag gattacctat aattgcaact attatagatg 3120
gtgtaagttt aggtgcagca atcaaagagc taagtgaaac gagtgaccca ttattaagac 3180
aagaaataga agctaagata ggtataatgg cagtaaattt aacaacagct acaactgcaa 3240
tcattacttc atctttgggg atagctagtg gatttagtat acttttagtt cctttagcag 3300
gaatttcagc aggtatacca agcttagtaa acaatgaact tgtacttcga gataaggcaa 3360
caaaggttgt agattatttt aaacatgttt cattagttga aactgaagga gtatttactt 3420
tattagatga taaagtaatg atgccacaag atgatttagt gatatcagaa atagatttta 3480
ataataattc aatagtttta ggtaaatgtg aaatctggag aatggaaggt ggttcaggtc 3540
atactgtaac tgatgatata gatcacttct tttcagcacc atcaataaca tatagagagc 3600
cacacttatc tatatatgac gtattggaag tacaaaaaga agaacttgat ttgtcaaaag 3660
atttaatggt attacctaat gctccaaata gagtatttgc ttgggaaaca ggatggacac 3720
caggtttaag aagcttagaa aatgatggca caaaactgtt agaccgtata agagataact 3780
atgaaggtga gttttattgg agatattttg cttttatagc tgatgcttta ataacaacat 3840
taaaaccaag atatgaagat actaatataa gaataaattt agatagtaat actagaagtt 3900
ttagggtata aatatagaat taagtgaaag tgatgtttgg attatagatg ttgataatgt 3960
tgtgagagat gtaactatag aatctgataa aattaaaaaa ggtgatttaa tagaaggtat 4020
tttatctaca ctaagtattg aagagaataa aattatctta aatagccatg agattaattt 4080
ttctggtgag gtaaatggaa gtaatggatt tgtttcttta acattttcaa ttttagaagg 4140
aataaatgca attatagaag ttgatttatt atctaaatca tataaattac ttatttctgg 4200

-continued

```
cgaattaaaa atattgatgt taaattcaaa tcatattcaa cagaaaatag attatatagg   4260

attcaatagc gaattacaga aaaatatacc atatagcttt gtagatagtg aaggaaaaga   4320

gaatggtttt attaatggtt caacaaaaga aggtttattt gtatctgaat tacctgatgt   4380

agttcttata agtaaggttt atatggatga tagtaagcct tcatttggat attatagtaa   4440

taatttgaaa gatgtcaaag ttataactaa agataatgtt aatatattaa caggttatta   4500

tcttaaggat gatataaaaa tctctctttc tttgactcta caagatgaaa aaactataaa   4560

gttaaatagt gtgcatttag atgaaagtgg agtagctgag attttgaagt tcatgaatag   4620

aaaaggtagt acaaatactt cagattcttt aatgagcttt ttagaaagta tgaatataaa   4680

aagtattttc gttaatttct tacaatctaa tattaagttt atattagatg ctaattttat   4740

aataagtggt actacttcta ttggccaatt tgagtttatt tgtgatgaaa ataataatat   4800

acaaccatat ttcattaagt ttaatacact agaaactaat tatactttat atgtaggaaa   4860

tagacaaaat atgatagtgg aaccaaatta tgatttagat gattctggag atatatcttc   4920

aactgttatc aatttctctc aaaagtatct ttatggaata gacagttgtg ttaataaagt   4980

tgtaatttca ccaaatattt atacagatga aataaatata acgcctgtat atgaaacaaa   5040

taatacttat ccagaagtta ttgtattaga tgcaaattat ataaacgaaa aaataaatgt   5100

taatatcaat gatctatcta tacgatatgt atggagtaat gatggtaatg attttattct   5160

tatgtcaact agtgaagaaa ataaggtgtc acaagttaaa ataagattcg ttaatgtttt   5220

taaagataag actttggcaa ataagctatc ttttaacttt agtgataaac aagatgtacc   5280

tgtaagtgaa ataatcttat catttacacc ttcatattat gaggatggat tgattggcta   5340

tgatttgggt ctagtttctt tatataatga gaaattttat attaataact ttggaatgat   5400

ggtatctgga ttaatatata ttaatgattc attatattat tttaaaccac cagtaaataa   5460

tttgataact ggatttgtga ctgtaggcga tgataaatac tactttaatc caattaatgg   5520

tggagctgct tcaattggag agacaataat tgatgacaaa aattattatt tcaaccaaag   5580

tggagtgtta caaacaggtg tatttagtac agaagatgga tttaaatatt ttgccccagc   5640

taatacactt gatgaaaacc tagaaggaga agcaattgat tttactggaa aattaattat   5700

tgacgaaaat atttattatt ttgaagataa ttatagagga gctgtagaat ggaaagaatt   5760

agatggtgaa atgcactatt ttagcccaga aacaggtaaa gcttttaaag gtctaaatca   5820

aataggtgat gataaatact atttcaattc tgatggagtt atgcaaaaag gatttgttag   5880

tataaatgat aataaacact attttgatga ttctggtgtt atgaaagtag gttacactga   5940

aatagatggc aagcatttct actttgctga aaacggagaa atgcaaatag gagtatttaa   6000

tacagaagat ggatttaaat attttgctca tcataatgaa gatttaggaa atgaagaagg   6060

tgaagaaatc tcatattctg gtatattaaa tttcaataat aaaatttact attttgatga   6120

ttcatttaca gctgtagttg gatggaaaga tttagaggat ggttcaaagt attattttga   6180

tgaagataca gcagaagcat atataggttt gtcattaata aatgatggtc aatattattt   6240

taatgatgat ggaattatgc aagttggatt tgtcactata aatgataaag tcttctactt   6300

ctctgactct ggaattatag aatctggagt acaaaacata gatgacaatt atttctatat   6360

agatgataat ggtatagttc aaattggtgt atttgatact tcagatggat ataaatattt   6420

tgcacctgct aatactgtaa atgataatat ttacggacaa gcagttgaat atagtggttt   6480

agttagagtt ggtgaagatg tatattattt tggagaaaca tatacaattg agactggatg   6540
```

gatatatgat atggaaaatg aaagtgataa atattatttc gatccagaaa ctaaaaaagc 6600
atgcaaaggt attaatttaa ttgatgatat aaaatattat tttgatgaga agggcataat 6660
gagaacgggt cttatatcat ttgaaaataa taattattac tttaatgaga atggtgaaat 6720
gcaatttggt tatataaata tagaagataa gatgttctat tttggtgaag atggtgtcat 6780
gcagattgga gtatttaata caccagatgg atttaaatac tttgcacatc aaaatacttt 6840
ggatgagaat tttgagggag aatcaataaa ctatactggt tggttagatt tagatgaaaa 6900
gagatattat tttacagatg aatatattgc agcaactggt tcagttatta ttgatggtga 6960
ggagtattat tttgatcctg atacagctca attagtgatt agtgaataga taa 7013

<210> SEQ ID NO 3
<211> LENGTH: 7010
<212> TYPE: DNA
<213> ORGANISM: Clostridium difficile

<400> SEQUENCE: 3
atgagtttag ttaatagaaa acagttagaa aaaatggcaa atgtaagatt tcgtgttcag 60
gaagatgaat atgtagcaat attagatgca ttagaagaat atcataatat gtcagaaaat 120
actgtagttg aaaagtatct aaaattaaaa gatataaaca gtttaacaga tacttatata 180
gatacatata aaaaatctgg tcgaaataaa gccttaaaaa aatttaaaga gtacttagtt 240
atagagatat tagaattaaa aaatagcaat ttaactccag tcgagaaaaa tttacatttt 300
atatggattg gagggcaaat aaatgatact gctattaatt atataaatca atggaaagat 360
gtaaatagtg actataatgt taatgttttt tatgatttaa ccacactgca attttcagaa 420
aacgtatgca aataatctat gataaacagc aaaatttcat aaattactat aaagctcaaa 480
aagaagaaaa tcctgacctt ataattgatg atattgtaaa gacatatctt tcaaacgagt 540
attcaaagga tatagatgaa cttaatgctt atattgaaga gtcattaaac aaagtcacag 600
aaaatagtgg aaatgatgtt agaaactttg aagaatttaa aactggagaa gtattcaatt 660
tatatgaaca agagtcagta gaaagatgga atcttgctgg tgcatctgat atattaagag 720
tcgctatatt gaaaaatatt ggtggagtct atctagatgt tgatatgtta ccaggaatac 780
acccagattt atttaaagat ataaataagc ctgattcagt aaagacagct gtagatttgg 840
gaagagatgc agttagaagc cataatgaaa cataaagaat atataccaga atatacttcg 900
aaacattttg atacattgga tgaagaagtt caaagtagct ttgaatctgt tttagcttct 960
aagtctgata agtcagaaat atttttacca ctaggagata tagaggtatc acctttagaa 1020
gtaaaaattg catttgccaa aggttctatt ataaatcaag ctctaatttc tgcaaaagat 1080
tcatattgta gtgacttact aataaaacaa atccaaaaca gatataagat actgaatgat 1140
actttaggtc caattattag tcaaggtaat gattttaata ctacaatgaa caattttggt 1200
gaaagtttgg gagctatagc taatgaagag aatataagtt ttatagcaaa aatcggaagt 1260
tatttaaggg ttggatttta tcctgaagct aatactacat tactttaagt ggtcctacaa 1320
tatatgcagg agcttataaa gatttattaa catttaaaga gatgagcata gatacttcta 1380
tattgtcgat ctgagttaag aaattttgaa tttcctaagg ttaatatatc tcaagcaaca 1440
gaacaagaga aaaatagttt atggcaattt aatgaagaaa gagctaaaat tcaatttgaa 1500
gaatacaaga aaaattattt tgaaggtgca cttggagaag atgataatct tgatttttct 1560
caaaatacag taactgacaa agaatatctt ttagaaaaga tctcttcatc aacgaagaag 1620
ttcagaaaga ggatatgttc attatattgt tcaattacaa ggagataaaa ttagctatga 1680

-continued

```
agcagcatgt aacttatttg caaaaaatcc ttatgacagt atactatttc aaagaaatat   1740
agaagattca gaagtagcat attactataa tcctacagat agtgaaatac aagaaattga   1800
taagtataga attcctgata gaatctctga tagacctaag attaaattaa cattcattgg   1860
tcatggcaaa gctgaattta atactgatat atttgcaggt cttgatgtag attcattatc   1920
ttcagaaata gaaacagcaa taggtttagc caaagaggat atttctccta aatctataga   1980
aataaactta ctgggatgta acatgtttag ctattctgta aatgtagaag agacttatcc   2040
tgggaaatta ttacttagag ttaaagataa agtatcagaa ttaatgccat ctatgagtca   2100
agactctatt atagtaagtg caaatcaata tgaagttaga ataaatagtg aaggaagaag   2160
agaattatta gaccattctg gtgaatggat aaacaaagaa gaaagtatta taaaggatat   2220
ttcatcaaaa gaatatatat catttaatcc taaagagaat aaaattatag taaaatctaa   2280
aaatttacct gaattatcta cattattaca agaaattaga aataattcta attcaagtga   2340
tattgaacta gaagaaaaag taatgttagc agaatgtgag ataaatgtta tttcaaatat   2400
agagacacaa gtggtagaag aaagaattga agaagctaaa agcttaactt ctgactctat   2460
taattatata aagaatgaat ttaaactaat agaatctatt tctgaggcac tatgtgactt   2520
aaaacaacag aatgaattag aagattctca ttttatatct tttgaggaca tatcagagac   2580
tgatgagggg tttagtataa gatttattaa taaagaaact ggagaatcta tatttgtaga   2640
aactgaaaaa acaatattct ctgaatatgc taatcatata actgaagaga tttctaagat   2700
aaaaggtact atatttgata ctgtaaatgg taagttagta aaaaaagtaa atttagatac   2760
tacacacgaa gtaaatactt taaatgctgc atttttttata caatcattaa tagaatataa   2820
tagttctaaa gaatctctta gtaatttaag tgtagcaatg aaagttcaag tttacgctca   2880
attatttagt actggtttaa atactattac agatgcagcc agagttgttg aattagtatc   2940
aactgcatta gatgaaacta tagacttact tcctacatta tctgaaggat tacctataat   3000
tgcaactatt atagatggtg taagtttagg tgcagcaatc aaagagctaa gtgaaacgag   3060
tgacccatta ttaagacaag aaatagaagc taagataggt ataatggcag taaatttaac   3120
aacagctaca actgcaatca ttacttcatc tttggggata gctagtggat ttagtatact   3180
tttagttcct ttagcaggaa tttcagcagg tataccaagc ttagtaaaca atgaacttgt   3240
acttcgagat aaggcaacaa aggttgtaga ttattttaaa catgtttcat tagttgaaac   3300
tgaaggagta tttactttat tagatgataa agtaatgatg caacaagatg atttagtgat   3360
atcagaaata gattttaata ataattcaat agttttaggt aaatgtgaaa tctggagaat   3420
ggaaggtggt tcaggtcata ctgtaactga tgatatagat cacttctttt cagcaccatc   3480
aataacatat agagagccac acttatctat atatgacgta ttggaagtac aaaaagaaga   3540
acttgatttg tcaaaagatt taatggtatt acctaatgct ccaaatagag tatttgcttg   3600
ggaaacagga tggacaccag gtttaagaag cttagaaaat gatggcacaa aactgttaga   3660
ccgtataaga gataactatg aaggtgagtt ttattggaga tattttgctt ttatagctga   3720
tgctttaata acaacattaa aaccaagata tgaagatact aatataagaa taaatttaga   3780
tagtaatact agaagtttta tagttccaat aataactaca gaatatataa gagaaaaatt   3840
atcatattct ttctatggtt caggaggaac ttatgcattg cctctttctc aatataatat   3900
gggtataaat atagaattaa gtgaaagtga tgtttggatt atagatgttg ataatgttgt   3960
gagagatgta actatagaat ctgataaaat taaaaaaggt gatttaatag aaggtatttt   4020
```

-continued

```
atctacacta agtattgaag agaataaaat tatcttaaat agccatgaga ttaatttttc   4080
tggtgaggta aatggaagta atggatttgt ttctttaaca ttttcaattt tagaaggaat   4140
aaatgcaatt atagaagttg atttattatc taaatcatat aaattactta tttctggcga   4200
attaaaaata ttgatgttaa attcaaatca tattcaacag aaaatagatt atataggatt   4260
caatagcgaa ttacagaaaa atataccata tagctttgta gatagtgaag gaaaagagaa   4320
tggttttatt aatggttcaa caaaagaagg tttatttgta tcagaattac ctgatgtagt   4380
tcttataagt aaggtttata tggatgatag taagccttca tttggatatt atagtaataa   4440
tttgaaagat gtcaaagtta taactaaaga taatgttaat atattaacag gttattatct   4500
taaggatgat ataaaaatct ctctttcttt gactctacaa gatgaaaaaa ctataaagtt   4560
aaatagtgtg catttagatg aaagtggagt agctgagatt ttgaagttca tgaatagaaa   4620
aggtagtaca aatacttcag attctttaat gagcttttta gaaagtatga atataaaaag   4680
tattttcgtt aatttcttac aatctaatat taagtttata ttagatgcta attttataat   4740
aagtggtact acttctattg gccaatttga gtttatttgt gatgaaaata ataatataca   4800
accatatttc attaagttta atacactaga aactaattat actttatatg taggaaatag   4860
acaaaatatg atagtggaac caaattatga tttagatgat tctggagata tatcttcaac   4920
tgttatcaat ttctctcaaa agtatcttta tggaatagac agttgtgtta ataaagttgt   4980
aatttcacca aatatttata cagatgaaat aaatataacg cctgtatatg aaacaaataa   5040
tacttatcca gaagttattg tattagatgc aaattatata aacgaaaaaa taaatgttaa   5100
tatcaatgat ctatctatac gatatgtatg gagtaatgat ggtaatgatt ttattcttat   5160
gtcaactagt gaagaaaata aggtgtcaca agttaaaata agattcgtta atgtttttaa   5220
agataagact ttggcaaata agctatcttt taactttagt gataaacaag atgtacctgt   5280
aagtgaaata atcttatcgt ttacaccttc atattatgag gatggattga ttggctatga   5340
tttgggtcta gtttctttat ataatgagaa attttatatt aataactttg gaatgatggt   5400
atctggatta atatatatta atgattcatt atattatttt aaaccaccag taaataattt   5460
gataactgga tttgtgactg taggcgatga taaatactac tttaatccaa ttaatggtgg   5520
agctgcttca attggagaga caataattga tgacaaaaat tattatttca accaaagtgg   5580
agtgttacaa acaggtgtat ttagtacaga agatggattt aaatattttg ccccagctaa   5640
tacacttgat gaaaacctag aaggagaagc aattgatttt actggaaaat taattattga   5700
cgaaaatatt tattattttg aagataatta tagaggagct gtagaatgga aagaattaga   5760
tggtgaaatg cactatttta gcccagaaac aggtaaagct tttaaaggtc taaatcaaat   5820
aggtgatgat aaatactatt tcaattctga tggagttatg caaaaaggat ttgttagtat   5880
aaatgataat aaacactatt ttgatgattc tggtgttatg aaagtaggtt acactgaaat   5940
agatggcaag catttctact ttgctgaaaa cggagaaatg caaataggag tatttaatac   6000
agaagatgga tttaaatatt ttgctcatca taatgaagat ttaggaaatg aagaaggtga   6060
agaaatctca tattctggta tattaaattt caataataaa atttactatt ttgatgattc   6120
atttacagct gtagttggat ggaaagattt agaggatggt tcaaagtatt attttgatga   6180
agatacagca gaagcatata taggtttgtc attaataaat gatggtcaat attattttaa   6240
tgatgatgga attatgcaag ttggatttgt cactataaat gataaagtct tctacttctc   6300
tgactctgga attatagaat ctggagtaca aaacatagat gacaattatt tctatataga   6360
tgataatggt atagttcaaa ttggtgtatt tgatacttca gatggatata aatattttgc   6420
```

```
acctgctaat actgtaaatg ataatattta cggacaagca gttgaatata gtggtttagt   6480

tagagttggt gaagatgtat attattttgg agaaacatat acaattgaga ctggatggat   6540

atatgatatg gaaaatgaaa gtgataaata ttatttcgtt ccagaaacta aaaaagcatg   6600

caaaggtatt aatttaattg atgatataaa atattatttt gatgagaagg gcataatgag   6660

aacgggtctt atatcatttg aaaataataa ttattacttt aatgagaatg gtgaaatcca   6720

atttggttat ataaatatag aagataagat gttctatttt ggtgaagatg gtgtcatgca   6780

gattggagta tttaatacac cagatggatt taaatacttt gcacatcaaa atactttgga   6840

tgagaatttt gagggagaat caataaacta tactggttgg ttaggtttag atgaaaagag   6900

atattatttt acagatgaat atattgcagc aactggttca gttattattg atggtgagga   6960

gtattatttt gatcctgata cagctcaatt agtgattagt gaatagataa              7010
```

<210> SEQ ID NO 4
<211> LENGTH: 7111
<212> TYPE: DNA
<213> ORGANISM: Clostridium difficile

<400> SEQUENCE: 4

```
atgagtttag ttaatagaaa acagttagaa aaaatggcaa atgtaagatt tcgtgttcag     60

gaagatgaat atgtagcaat attagatgca ttagaagaat atcataatat gtcagaaaat    120

actgtagttg aaaagtatct aaaattaaaa gatataaaca gtttaacaga tacctatata    180

gatacatata aaaaatctgg tccaaataaa gccttaaaaa aatttaaaga gtacttagtt    240

acagagtatt agaattaaaa aatagcaatt taactccagt cgagaaaaat ttacatttta    300

tatggattgg agggcaaata aatgatactg ctattaatta tataaatcaa tggaaagatg    360

taaatagtga ctataatgtt aatgtttttt atgatagtaa tgcatttttg ataaacacat    420

tgaaaaaaac tataatagaa tcagcatcaa atgataccct tgaatcattt agagaaaatt    480

taaatgatcc tgaatttaac cacactgcaa ttttcagaaa acgtatgcaa ataatctatg    540

ataaacagca aaatttcata aattactata aagctcaaaa agaagaaaat cctgacctta    600

taattgatga tattgtaaag acatatcttt caaacgagta ttcaaaggat atagatgaac    660

ttaatgctta tattgaagag tcattaaaca aagtcacaga aaatagtgga aatgatgtta    720

gaaactttga agaatttaaa actggagaag tattcaattt atatgaacaa gagttagtag    780

aaagatggaa tcttgctggt gcatctgata tattaagagt cgctatattg aaaaatattg    840

gtggagtcta tctagatgtt gatatgttgc caggaataca cccagattta tttaaagata    900

taaataagcc tgattcagta aagacagctg tagattggga agagatgcag ttagaagcca    960

taatgaaata taaagaatat ataccagaat atacttcaaa acattttgat acattggatg   1020

aagaagttca aagtagcttt gaatctgttc tagcttctaa gtctgataag tcagaaatat   1080

ttttaccact aggagatata gaggtatcac ctttagaagt aaaagttgca tttgccaaag   1140

gttctattat agatcaagct ctaatttctg caaaagactc atattgtagt gacttactaa   1200

taaaacaaat ccaaaacaga tataagatac tgaatgatac tttaggtcca attattagtc   1260

aaggtaatga ttttaatact acaatgaaca attttggtga aagtttggga gctatagcta   1320

atgaagagaa tataagtttt atagcaaaaa tcggaagtta tttaagggtt ggattttatc   1380

ctgaagctaa tactacatta ctttaagtgg tcctacaata tatgcaggag cttataaaga   1440

tttattaaca tttaaagaga tgagcataga tacttctata ttgtcgatct gagttaagaa   1500
```

-continued

```
attttgaatt tcctaaggtt aatatatctc aagcaacaga acaagagaaa aatagtttat   1560
ggcaatttaa tgaagaaaga gctaaaattc aatttgaaga atacaagaaa aattattttg   1620
aaggtgcact tggagaagat gataatcttg atttttctca aaatacagta actgacaaag   1680
aatatctttt agaaaagatc tcttcatcaa cgaagaagtt cagaaagagg atatgttcat   1740
tatattgttc aattacaagg agataaaatt agctatgaag cagcatgtaa cttatttgca   1800
aaaaatcctt atgacagtat actatttcaa aaaaatatag aagattcaga agtagcatat   1860
tactataatc ctacagatag tgaaatacaa gaaattgata agtatagaat tcctgataga   1920
atctctgata gacctaagat taaattgaca ctcattggtc atggcaaagc tgagtttaat   1980
actgatatat ttgcaggtct tgatgtggat tcattatctt cagaaataga aacaatatta   2040
gatttagcta aagcagatat ttctcctaaa tctatagaaa taaacttact gggatgtaac   2100
atgtttagct attctgtaaa tgtagaagag acttatcctg ggaaattatt acttagagtt   2160
aaagataaag tatcagaatt aatgccatct ataagtcaag actctattat agtaagtgca   2220
aatcaatatg aagttagaat taatagtgaa ggaagaagag aattattaga ccattctggt   2280
gaatggataa acaaagaaga aagtattata aaggatattt catcaaaaga atatatatca   2340
tttaatccta aagaaaataa aattatagta aaatctaaaa atttacccga attatctaca   2400
ttattacaag aaattagaaa caattctaat tcaagtgata ttgaactaga agaaaaagta   2460
atgttagcag aatgtgagat aaatgttatt tcaaatatag agacacaagt ggtagaagaa   2520
aggattgaag aagctaaaag cttaacttct gactctatta attatataaa gaatgaattt   2580
aaactaatag aatctatttc tgatgcacta tacgatttaa aacaacagaa tgaattagaa   2640
gagtctcatt ttatatcttt tgaggatata tcagaagact gatgaaggct ttagtataag   2700
atttattgat aaagaaactg gagaatctat atttgtagaa actgaaaagg caatattctc   2760
tgaatatgct aatcatataa ctgaagaaat ttctaagtta aaagatacta tatttgatac   2820
tgtaaatggt aagttggtga aaaaagtaac tttagatgct acacatgaag tgaatacttt   2880
aaatgctgca tttttatac aatcattaat tggatataat agttctaaag aatctcttag   2940
taatttaagt gtagcaatga aagttcaagt ttatgctcaa ttatttagta ctggtttaaa   3000
taccattaca gatgcggcta aagttgttga attagtatca actgcactag atgaaactat   3060
agatttactt cctacattat ctgaaggatt acctgtaatt gctactatta tagatggtgt   3120
aagtttaggt gcatcaatta aagagttgag tgaaacaagt gacccattat taagacaaga   3180
aatagaagca aaaataggta taatggcagt aaatttaaca gcagctacaa ctgcaattat   3240
tacttcatct ttaggaatag caagtggatt tagtatactt ttagttcctc tagcagggat   3300
ttcagcagga atcccaagtt tagtaaataa tgaacttata ttacgagctg aggcaaaaaa   3360
tgtcgtagat tattttggcc atatttcatt agctgaatct gaaggagcat ttactttgtt   3420
agatgataaa ataatgatgc cacaagatga tttagtaata tctgaaatag actttaataa   3480
caattcaata actttaggta aatgtgaaat atggagaatg gaaggtggtt caggtcatac   3540
tgtaaccgat gatatagatc acttcttctc agcaccatca acaacatata gggaaccata   3600
tttatctata tatgatgtat tagatgtaaa agaggaagaa cttgatttat caaaagattt   3660
aatggtatta gctaatgccc cagatagaat ctttggctgg gaaagaggat ggacgccagg   3720
tttaagaagc ttagaaaatg atggtacaaa actattagac cgtataagag atcattatga   3780
agggcagttt tattggagat tttcgcttt tatagctgat tctgtaataa caaaattaaa   3840
accaagatat gaagatacta atataagaat aagtttagac agtaatacta gaagttttat   3900
```

-continued

```
agttccagta ataactacag aatatataag agaaaaatta tcatattctt tttatggttc   3960
aggaggaact tatgcattat ctctttctca atacaatatg aatataaaca tagaattaaa   4020
tgaaaatgat acttgggtta tagatgtcga ctaatgcgta agagatgtca ctatagaatc   4080
tgataaaatt aaaaaaggag atttaataga aaatatttta tctaaattaa gtattgaaga   4140
caataaaatt attttagata atcatgaaat taatttctct ggaacattaa atggaggtaa   4200
tggatttgta tctttaacat tctcaatctt agaaggaata aatgcagtta tagaagttga   4260
tttattatct aaatcatata aagttcttat ttctggtgaa ctaaaaacat tgatggcaaa   4320
ttcaaattct gttcaacaga aaatagatta tataggattg aatagcgaat tacaaaaaaa   4380
tataccttat agttttatgg atgatgaagg aaaagaaaat ggatttatta attgttttac   4440
aaaagaaggt ttatttgtat ctgaattatc tgatgtagtt ctcataatta aagtttatat   4500
ggacaatagt aaacctccat ttggatatta tagtaatgat ttgaaagatg ttaaagttat   4560
aactaaagat gacgttatta taataacagg ttaatatctt aaaagatgat ataaaaatct   4620
ctctttcttt tactatacaa gataaaaata ctataaaatt aaatggagta tatttagatg   4680
aaaatggagt agctgaaata ttgaaattta tgaataaaaa aggtagtaca aatacttcag   4740
attctttaat gagcttttta gaaagtatga acataaaaag tattttcata aaatccttaa   4800
aatctaatgc taagcttata ttagatacta attttataat aagtggtact acttttattg   4860
gtcaatttga gtttatttgt gataaagata ataatataca accatatttc attaagttta   4920
atacactaga aactaaatat actctatatg taggtaatag acaaaatatg atagtagaac   4980
caaattataa tttagatgat tctggagaca tatcttcaac tgtcattaat ttttctcaga   5040
aatacctta tggaatagac agttgtgtta ataaagttgt aatttcacca gggatttata   5100
cagatgaaat aaatataacg cctgtacatg aagcaaataa tacttatcca gaagtgattg   5160
tattagatac aaattatata agtgaaaaaa tcaatattaa tatcaatgat ttatctatac   5220
gatatgtatg gagaagtgat ggtaatgatt ttattcttat gtcaactgat gaagagaaca   5280
aggtatcaca agttaaaata agatttacta atgtttttaa aggtaatact atatcagata   5340
agatatcttt taattttagt gacaagcaag atatatctat aaataaaatt atttcaacat   5400
ttacaccttc atattatgtg gaaggattac ttaattatga tttaggtctg atttctttat   5460
acaatgagaa attttatatt aataatttgg gaatgatggt gtctgggtta gtatatatta   5520
atgattcatt atattatttc aaaccaccaa taaagaactt gataactgga tttacaacta   5580
taggcgatga taaatactac tttaatccag attaatggag gacctgcttc agttggagaa   5640
acaataattg atggcaaaaa ctactatttc agccaaaatg gagtgttaca aacaggtgta   5700
tttagtacag aagatggatt taaatatttt gctccagcag atacacttga tgaaaatcta   5760
gaaggtgaag caattgattt tactggcaaa ctaattattg atgaaaatgt atattatttt   5820
ggagataatt atagagcagc tatagaatgg caaacattag atgatgaaat gtactatttt   5880
agcacagata caggtagagc ttttaaaggg ctaaatcaaa taggtgatga taaattctat   5940
ttcaactctg atggtattat gcaaaaagga tttgttaata taaatgataa gacattttat   6000
tttgatgatt ctggtgtgat gaagtcagga tatactgaaa tagatggaag atatttttac   6060
tttgctgaag atggagaaat gcaaatagga gtatttaata cagcagatgg atttaaatat   6120
tttgctcatc atgatgaaga tttaggaaat gaagaaggtg aagcactttc atattctggt   6180
atacttaatt ttaacaataa gatttattat tttgatgatt catttacagc agtagttgga   6240
```

-continued

```
tggaaggatt tagaagatgg ttcaaaatat tactttgatg aaaatacagc agaagcatct   6300

ataggtatat caataattaa tgatgggaaa tattatttta atgattctgg aatcatgcaa   6360

attggatttg tcacaataaa taatgaagtt ttttatttct ctgattctgg aatagtagaa   6420

tctggaatgc aaaatataga tgataactat ttctatataa gtgataatgg tctagttcaa   6480

attggtgtat ttgacacttc agatggatat aaatactttg caccagctaa tactgtaaat   6540

gataatattt atggacaagc agttgaatat agtggtttag ttagagttaa tgaagatgtg   6600

tatagttttg gagaatcata tacaattgaa actggatgga tatatgattc agaaaacgaa   6660

agtgataaat attatttcga tccagaagct aaaaaagcat ataaaggtat caatgtaatt   6720

gatgatataa aatactattt tgatgagaat ggcataatga gaacaggtct tataacattt   6780

gaagataatc attactattt taatgaagat ggtgaaatgc aatatggtta tctaaatata   6840

gaagataaga tgttctactt tagtgaagat ggtattatgc agattggagt atttaataca   6900

ccagatggat ttaaatattt tgcacatcaa aatactttag atgagaattt tgagggagaa   6960

tcaataaact atactggttg gttagattta gatgaaaaga gatattattt tacagatgaa   7020

tatatcgcag caactggttc agttattatt gatggtgagg agtattattt tgatcctgat   7080

acagctcaat tagtgattag tgaatagata a                                  7111
```

<210> SEQ ID NO 5
<211> LENGTH: 1264
<212> TYPE: DNA
<213> ORGANISM: Clostridium difficile

<400> SEQUENCE: 5

```
tagtaatgca tttttgataa acacattgaa aaaaactata atagaatcag catcaaatga     60

taccttgaa tcatttagag aaaatttaaa tgatcctgaa tttaaccaca ctgcaatttt    120

cagaaaacgt atgcaaatca tctatgataa acagcaaaat ttcataaatt actataaagt    180

tcaaaaagaa gaaaatcacc ttataattga tgatattgta aagacatatc tttcaaacga    240

gtattcaaag gatatagatg aacttaatgc ttatattgaa gagtcattaa acaaagtcac    300

agaaaatagt ggaaatgatg ttagaaactt tgaagaattt aaaactggag aagtattcaa    360

tttatatgaa caagagttgg tagaaagatg gaatcttgct ggtgcatctg atatattaag    420

agtcgctata ttgaaaaata ttggtggagt ctatctagat gttgatatgt taccaggaat    480

acacccagat ttatttaaag atataaataa gcctgattca gtaaagacag ctgtagattg    540

ggaagagatg cagttagaag ccataatgaa atataaagaa tatataccag aatatacttc    600

aaaacatttt gatacattgg atgaagaagt tcaaagtagc tttgaatctg ttctagcttc    660

taagtctaat aagtcagaaa tatttttacc actaggagat atagaggtat cacctttaga    720

agtaaaaatt gcatttgcca aaggttctat tataaatcaa gctctaattt ctgcaaaaga    780

ctcatattgt agtgacttac taataaaaca aatccaaaac agatataaga cactgaatga    840

tactttaggt ccaattatta gtcaaggtaa tgattttaat actacaatga acaattttgg    900

tgaaagtttg ggagctatag ctaatgaaga gaatataagt tttatagcaa aaatcggaag    960

ttatttaagg gttggatttt atcctgaagc taatactaca ttactttaag tggtcctaca   1020

atatatgcag gagcttataa agatttatta acatttaaag agatgagcat agatacttct   1080

atattgtcga tctgagttaa gaaatttcga atttcctaag gttaatatat ctcaagcaac   1140

agaacaagag aaaaatagtt tatggcaatt taacgaagaa agagctaaaa ttcaatttga   1200

agaatacaag aaaaattatt ttgaaggtgc acttggagaa gatgataatc ttgatttttc   1260
```

-continued tcag 1264

<210> SEQ ID NO 6
<211> LENGTH: 7090
<212> TYPE: DNA
<213> ORGANISM: Clostridium sordellii

<400> SEQUENCE: 6
atgagcttag ttaacaaagc ccaattacaa aaaatggtat atgtaagatt tcgtattcag 60
gaagatgagt acgtagcaat attaaatgct ctagaagaat atcacaacat gtcagaaaat 120
agtgtagttg aaaagtattt aaaattaaag gatataaata atctcacaga taattacctg 180
aacacatata aaaaatctgg aaggaataaa gccttaaaaa aatttaaaga atactaacta 240
tggagtatta gagctaaaaa ataatagtct aactccagtc gaaaaaaatt tacattttat 300
atggattgga ggacaaataa atgataccgc tatcaactat ataaatcaat ggaaagatgt 360
aaatagcgat tatacagtta aagtttttta tgatagtaat gcatttttga taaacacatt 420
gaagaaaact attgttgagt cagcaacaaa taatactctt gagtcattta gagaaaactt 480
aaatgaccct gaattcgatt ataataaaat ttatagaaaa cgtatggaaa taatatatga 540
taaacaacaa cattttatag attattataa gtctcagata gaagagaatc ctgacattat 600
aattgataat attataaaaa catatctctc aaatgagtat tcaaaagacc tagatgccct 660
taataagtat attgaagaat ctttaaataa aattactgct aataatggta atgatatcag 720
aaatctagaa aaatttgctg atgaggattt ggtcagatta tataatcaag agttagtaga 780
aagatggaat ttggctgctg cttctgacat attacgaata tctatgttaa aaaagatggt 840
ggtgtatatt tagatgttga catgttacca ggtatacaac cagatttatt taagatataa 900
acaagcctga ttcgataaca aatacaagtt gggaaatgat aaagttagag gccataatga 960
aatataagga atatatacca gggtatacgt caaagaattt tgacatgtta gatgaagaag 1020
ttcaacgcag ttttgaatct gctttaagtt ctaaatcaga taagtcagaa atttttttgc 1080
cacttgatga tataaaagta tccccgttag aagtaaaaat tgcatttgcc aataactctg 1140
ttataaatca agccttaatt tctttaaaag attcctattg tagtgattta gtaataaatc 1200
aaattaaaaa tagatataaa atcttgaacg acaacttaaa tccatccatt aatgaaggta 1260
ctgactttaa tactacaatg aaaattttta gtgacaaatt agcatctatt tctaatgaag 1320
ataatatgat gtttatgata aaaattacaa actatttaaa agttggattt gctccagatg 1380
ttagaagtac tattaacttt aagtggacct ggagtatata caggagctta tcaagatttg 1440
ttaatgttta aagataatag tacaaatatt catttactag aacctgagtt aagaaatttt 1500
gagtttccta aaactaaaat ttctcaatta acagaacagg aaataactag tttatggtca 1560
tttaaccaag caagagccaa gtctcaattt gaagaatata aaaaaggtta ttttgaaggt 1620
gcacttggag aagatgataa tcttgatttt gctcaaaata cagtacttga taaagattat 1680
gtttctaaaa aaatattatc atcaatgaaa acccgaaata aagaatatat tcattatatt 1740
gttcaactac aaggagataa aatcagctat gaagcatcat gtaacttatt ttcaaaagaa 1800
tccttattct agtatactat atcagaaaaa tatagaaggt tcagaaacag catattacta 1860
ttatgttgca gatgctgaga taaaagaaat agataaatat agaattccat atcaaatttc 1920
taataaacgt aatattaaat taacttttat tggtcatggt aaatctgaat ttaatactga 1980
tacatttgcc aatcttgatg tagattcatt atcttctgag atagaaacaa tattaaattt 2040

-continued agctaaagca gatatttctc ctaagtatat agaaataaat ttactgggat gtaacatgtt 2100
cagctactct atcagcgcag aagagactta tcctggaaaa cttttactta aaattaaaga 2160
tagagtatca gaattaatgc catctataag tcaagactct attacagtaa gtgcaaatca 2220
atatgaagtt agaataaatg aagaaggaaa aagagaaata ttagatcatt ctggtaaatg 2280
gataaataaa gaagaaagta ttataaagga tatttcatca aaagaatata tatcatttaa 2340
tccaaaagaa aataaaatta tagtgaaatc taaatattta catgagctgt ctacattatt 2400
acaagaaatt aggaataatg ccaattcaag tgatattgat ctagaaaaaa aagtaatgtt 2460
aacagaatgt gagataaatg ttgcttcaaa tatagataga cagattgtgg aaggaagaat 2520
tgaagaagct aaaaatttga cttctgactc tattaattat ataaaaaatg aatttaaact 2580
aatagaatct atttctgatt cattatatga tttaaaacat caaaatggat tagatgattc 2640
tcattttata tcttttgagg atatatccaa gactgaaaat ggatttagga taaggttcat 2700
taataaagaa actggaaact ctatatttat agaaactgaa aaagaaattt tctctgaata 2760
tgctactcat atatctaaag aaatttctaa tataaaagat actatatttg ataatgtaaa 2820
tggcaaatta gtaaaaaaag taaatctaga tgctgcacat gaagtaaata ctctaaattc 2880
tgcctttttt atacaatcat taatcgaata taatactact aaagaatcac ttagtaattt 2940
aagtgtagca atgaaggttc aagtttatgc tcaattattt agtactggtt taaatactat 3000
tacagatgct tctaaagttg ttgagttagt atcaactgca ttagatgaaa ctatagactt 3060
acttcctaca ttatctgaag gattacctgt aattgctaca ataatagatg gtgtaagctt 3120
aggcgcggca attaaagaac tcagcgaaac aaatgaccca ttattaagac aagaaataga 3180
agccaagata ggtataatgg ctgtaaattt aacagcagct tcaactgcaa tcgttacttc 3240
agctttagga atagctagtg gttttagcat acttttagtt cctttggcag gaatttcagc 3300
agggatacca agtttagtaa acaatgaact tatactccaa gataaggcaa caaaagttat 3360
agattatttt aaacatattt cattagctga gactgaggga gcatttacat tattagatga 3420
taaaaataatt atgcctcaag atgacttggt attatcagaa atagacttta ataataattc 3480
aataactttta ggtaaatgtg aaatctggag agctgaaggt ggttcaggcc ataccttaac 3540
tgatgatata gatcatttct tttcatcacc atcaataaca tatagaaaac catggttatc 3600
tatatatgat gtattaaata taaaaaaaga aaaaattgat ttttcaaaag atttaatggt 3660
attacctaat gcacctaata gggtatttgg ttatgaaatg ggatggacac cagggttcag 3720
aagtttagac aatgacggca ctaaattatt agatcgtata agagatcatt atgaaggtca 3780
attttattgg agatatttcg cttttatagc tgatgcttta ataacaaaat taaaaccacg 3840
atatgaagat actaatgtaa gaataaatct agatggcaat actagaagtt ttatagttcc 3900
agttataacc acagaacaaa taagaaaaaa tttatcttat tctttttatg gttcaggggg 3960
atcttattca ttatctcttt ctccatataa tatgaatata gatttaaatc tagttgaaaa 4020
tgatacttgg gttatagatg ttgataatgt tgtaaaaaac atcactatag agtcagatga 4080
aatacaaaaa ggtgaattaa tagaaaatat tttatctaag ctaaatattg aagataataa 4140
aattatttta aataatcata ctattaattt ctatggagat ataaatgaaa gcaacagatt 4200
tatatcttta acattttcaa ttttagagga tataaatata attatagaaa ttgatttagt 4260
atcaaaatct tataaaatac ttctttctgg taattgtatg aaattgatag aaaactcatg 4320
tgtattcaac aaaagataga tcatatagga tttaatggtg aacatcagaa atatatacct 4380
tatagttata tagataatga aactaaatac aacggtttta ttgactactc taaaaaagaa 4440

-continued

```
ggtctgttta cagctgaatt ttctaatgaa tccattataa ggaatattta tatgcctgat   4500
agtaataatt tatttatata ttctagtaaa gatttaaaag atattagaat tataaataaa   4560
ggtgatgtta aattactaat aggaaattac tttaaagatg atatgaaggt atcactttct   4620
ttcactatag aagatacaaa tactataaag ttgaatggtg tatatctaga tgaaaatgga   4680
gtagcacaaa tattgaaatt tatgaataat gcaaaaagtg ctttaaatac ttcaaactcg   4740
ttaatgaatt tcttagaaag tatcaacata aaaaatattt tctacaataa tctagaccct   4800
aatatcgagt ttatactaga tactaatttc ataataagtg gtagcaattc tattgggcaa   4860
tttgaactta tctgtgataa agataaaaat atacaaccat attttattaa ctttaaaata   4920
aaagaaacta gctatactct atatgtagga aatagacaaa atttgatagt ggaaccaagt   4980
tatcacttag atgattctgg aaatatatct tcaactgtca ttaatttctc tcagaaatat   5040
ctttatggaa tagaccgtta tgttaataaa gttataattg caccaaattt atatacagat   5100
gaaataaata taacacctgt atataaacca aattatattt gtccagaagt tattatatta   5160
gatgcaaatt atataaacga aaaaataaat gttaatatca atgacttatc tatacgatat   5220
gtatgggata atgatggtag tgatcttatt cttatagcaa atagtgagga agataatcaa   5280
ccacaagtta aaataagatt tgttaatgtc tttaaaagcg atactgcagc agataagttg   5340
tcttttaact tcagtgataa gcaagatgta tctgtaagta aaattatttc aacattttca   5400
cttgcagctt atagcgatgg atttttttgac tatgaatttg gtctgtttct ttagataatg   5460
attactttta tattaatagt tttggaaata tggtatctgg attaatatat attaatgatt   5520
cattatatta tttcaaacca ccaaaaaaata acttgataac tggattcaca actatagatg   5580
gtaataaata ttactttgac ccaacgaaga gtggagctgc atcaatagga gaaataacaa   5640
ttgatggtaa agattattac tttaacaaac aaggtatttt gcaagtagga gttattatta   5700
catctgatgg attaaagtat tttgctcctg ctggtacact tgatgaaaac ttagagggag   5760
atgcagtaaa ttttattgga aaattaaata ttgatggaaa aatttattat tttgaagata   5820
attatagagc cgctgtagag tggaaattat tagatgatga aacatactat ttcaatccaa   5880
aatcaggaga agcccttaaa ggtttacatc aaattggtga taataaatat tattttgatg   5940
ataatggaat tatgcaaact ggtttcatta ctataaatga taaggtattt tattttaata   6000
atgatggtgt gatgcaagtt ggatatattg aggtaaatgg taaatatttt tattttggca   6060
aaaatggaga aagacaatta ggagtattta atactccaga tggatttaaa tttttttggtc   6120
ctaaagatga tgatttagga actgaagaag gggaactaac cttatataat ggtatattga   6180
attttaatgg gaaaatctat tttttttgata tctcaaatac agctgtagtc ggatggggta   6240
ctcttgatga tggctctaca tattatttcg atgataatag agcagaagca tgcataggtt   6300
taacagtaat taatgattgt aagtattatt ttgatgataa cggaataagg caattaggat   6360
ttatcactat aaatgacaat atattttatt tctctgaatc tggaaaaata gagttaggat   6420
accaaaatat aaatggtaac tatttctaca tagatgaaag tggtttagtt ctaattggag   6480
tatttgatac cccagacgga tataaatatt ttgcacctct taatactgta aatgataata   6540
tttatggaca agcagttaaa tatagtggtt tagtaagggt taatgaggac gtatatagtt   6600
ttggtgaaac atataaaatt gaaactggat ggatagaaaa tgaaactgat aaatattatt   6660
ttgatccaga gactaaaaaa gcatataaag gcattaatgt agttgatgat ataaaatatt   6720
atttcgatga gaatggtata atgagaacag ggcttatatc atttgaaaat aataattatt   6780
```

-continued acttcaatga agatggtaaa atgcaatttg gttatctaaa tataaaagat aaaatgtttt 6840
attttggtaa agatggtaaa atgcagattg gagtatttaa taccccagat ggatttaaat 6900
actttgcaca tcaaaatact ttagatgaga attttgaggg ggaatcaata aactatactg 6960
gttggttaga tttagatggt aaaagatatt attttacaga tgaatatata gcagcaactg 7020
gctcattgac tattgatggt tacaattact attttgaccc tgatacagct gaattagtag 7080
ttagtgaata 7090

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
taatagaaaa cagttagaaa 20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
tccaatccaa acaaaatgta 20

<210> SEQ ID NO 9
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 9
tatataaatc aatggaaaga tgtaaatagt 30

<210> SEQ ID NO 10
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 10
tagtaatgca tttttgataa acacattgaa a 31

<210> SEQ ID NO 11
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 11
tttgaaagat atgtctttac aatatc 26

<210> SEQ ID NO 12
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 12
ttcttcaaag tttctaacat catttccac 29

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 13
atatcagaga ctgatgag 18

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
tagcatattc agagaatatt gt 22

<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
tgtagcaatg aaagtccaag tttacgc 27

<210> SEQ ID NO 16
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 16
ctttaaatgc tgcatttttt atacaatc 28

<210> SEQ ID NO 17
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 17
gaaagtccaa gtttacgctc aat 23

<210> SEQ ID NO 18
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 18
gctcaattat ttagtactgg tttaaatac 29

<210> SEQ ID NO 19

-continued

<211> LENGTH: 28
<212> TYPE: DNA
<213> ORGANISM: Artificial Sequence
<220> FEATURE:
<223> OTHER INFORMATION: oligonucleotide primer

<400> SEQUENCE: 19
tgcacctaaa cttacaccat ctataata 28

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 20
gctgcaccta aacttacacc a 21

<210> SEQ ID NO 21
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 21
cacttagctc tttgattgct gcacct 26

<210> SEQ ID NO 22
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 22
ctatttcttg tcttaataat gggtcac 27

<210> SEQ ID NO 23
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 23
gaaggtggtt caggtcatac 20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
aatggaaggt ggttcaggtc 20

<210> SEQ ID NO 25
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 25
cttaaacctg gtgtccatc 19

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 26
cattttctaa gcttcttaaa cctg 24

<210> SEQ ID NO 27
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 27
ggaaaagaga atggttttat taa 23

<210> SEQ ID NO 28
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 28
acaaaagaag gtttatttgt atc 23

<210> SEQ ID NO 29
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 29
atctttagtt ataactttga catcttt 27

<210> SEQ ID NO 30
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 30
cggttgttga attagtatca actgcacaac cg 32

<210> SEQ ID NO 31
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 31
ccggcgatgc ctcttcacat tgctccacct ttcctcgccg g 41

<210> SEQ ID NO 32
<211> LENGTH: 32
<212> TYPE: DNA

-continued

```
<213> ORGANISM: Artificial Sequence
<220> FEATURE:
<223> OTHER INFORMATION: oligonucleotide primer

<400> SEQUENCE: 32

cggttgttga attagtatca actgcacaac cg                          32


<210> SEQ ID NO 33
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 33

ccggcgatgc ctcttcacat tgctccacct ttcctcgccg g                41
```

DETECTION OF TOXIGENIC STRAINS OF *CLOSTRIDIUM DIFFICILE*

RELATED APPLICATION

This application claims priority under 35 U.S.C. §119(e) to U.S. Provisional Application No. 60/970,492, filed on Sep. 6, 2007, the content of which is incorporated by reference in its entirety.

FIELD OF THE INVENTION

The present invention relates to primers and probes for detection of toxin-producing (toxigenic) strains of *Clostridium difficile*, and to methods of detecting toxigenic strains using these primers and probes. More specifically, the invention relates to detection of *C. difficile* by nucleic acid-based amplification methods using particular primers and probes that bind to the toxin B (TcdB) gene. These primers and probes are used to amplify *C. difficile* nucleic acids in clinical samples to determine the presence of these toxigenic strains.

BACKGROUND OF THE INVENTION

*Clostridium difficile* is a spore-forming, gram-positive bacillus that produces exotoxins that are pathogenic to humans. *C. difficile*-associated disease (CDAD) ranges in severity from mild diarrhea to fulminant colitis and death. *C. difficile* typically has affected older or severely ill patients who are hospital inpatients or residents of long-term-care facilities. *C. difficile* is the major cause of pseudomembranous colitis and antibiotic associated diarrhea. *C. difficile*-associated disease occurs when the normal intestinal flora is altered, allowing *C. difficile* to flourish in the intestinal tract and produce a toxin that causes a watery diarrhea. One major cause for alteration of intestinal flora is the overuse of antibiotics. Repeated enemas, prolonged nasogastric tube insertion and gastrointestinal tract surgery also increase a person's risk of developing the disease. The overuse of antibiotics, especially penicillin (ampicillin), clindamycin and cephalosporins may also alter the normal intestinal flora and increase the risk of developing *C. difficile* diarrhea.

Toxigenic strains of *C. difficile* commonly produce two large toxins, an enterotoxin; toxin A (TcdA) and a cytotoxin; toxin B (TcdB), to which disease symptoms are attributed. They are expressed efficiently during growth of *C. difficile* in response to an environmental stimulus. Their activities modulate numerous physiological events in the cell and contribute directly to disease. In humans the two toxins cause diseases called pseudomembranous colitis and antibiotic associated diarrhea. Transmission occurs primarily in health care facilities, where exposure to antimicrobial drugs and environmental contamination by *C. difficile* spores are common (2, 3 and 4).

Toxin A and toxin B are encoded by genes tcdA and tcdB. Both have been sequenced and are found in single open reading frames. Together with three additional genes (tcdC, tcdD, tcdE), they form a 19.6 kb chromosomal pathogenicity locus (Paloc) (8). Both open reading frames are large, with tcdA spanning 8,133 nucleotides and tcdB being 7,098 nucleotides in length. FIG. 1 shows the genetic arrangement of the *C. difficile* Paloc. tcdD, renamed tcdR (Rupnik, M. et al., J. Med. Microbiol, 2005, 54: 113-117) is a proposed positive regulator, tcdE is a putative holin protein, and tcdC is a proposed negative regulator of toxin gene expression (Voth, D. E. et al., Clinical Microbiol. Reviews, 2005, 18: 247-263).

TcdA and TcdB are among the largest bacterial toxins reported, comparable in size to lethal toxin (TcsL) and hemorrhagic toxin (TcsH) of *C. sordellii* as well as alpha toxin (Tcns) of *C. novyi* (Voth, supra.). TcdA (308 kDa) and TcdB (270 kDa) are glucosyltransferases which inactivate small GTPases such as Rho, Rac and Cdc-42 within target cells (Voth, supra.). This inactivation causes disagreggation of the cellular cytoskeleton and alterations of other cellular processes which eventually lead to cell death (Voth, supra.). Both toxins use a highly conserved N-terminal domain (74% homology between TcdA and TcdB) to modify identical substrates. The proximal locations of tcdA and tcdB genes and the high sequence and functional homology between the two proteins inspired Von Eichel-Streiber to propose that the two genes may have arisen as the result of gene duplication (Knoop F. C. et al, Clin. Micro reviews, July 1993, 251-265).

TcdB also exhibits homology (85% homology and 74% identity) with lethal toxin (TscL) of *C. sordellii*, which glycosylates Ras, Rac, Rap and Ral. The major differences are found in the N terminus. These explain the differences in substrate specificity. TcdA is thought to be more similar in function to the hemorrhagic toxin (TcsH) of *C. sordellii* (Voth, supra.).

In early studies, it had been generally accepted that *C. difficile* toxigenic strains produced both toxin A and toxin B whereas nontoxigenic strains lacked both toxins (Rupnik et al. supra.; Lyerly et al., Clin. Micro. Rev., 1998, Jan., 1-18). Toxin variant strains were then discovered which failed to produce detectable toxin A, and yet produced toxin B (TcdA−/TcdB+). A third toxin (binary toxin CDT) has also been found in some *C. difficile* strains. Although the majority of binary toxin positive strains produce TcdA and TcdB (TcdA+TcdB+CDT+) some produce neither TcdA nor TcdB (TcdA−TcdB−CDT+). In the light of available data, *C. difficile* strains into toxigenic strains were classified as toxigenic if they produced at least one of the three known toxins, and nontoxigenic strains if they did not produce any of these three toxins (Rupnik et al., supra.).

While the primary work on TcdA and TcdB was carried out on toxins from the toxigenic reference strain VP1 10463, several genetic variants of these toxins now exist in clinical isolates (Voth et al., supra.). Two well-characterized strains which do not express toxin A (TcdA−TcdB+), 1470 and 8864, produce modified toxin B compared to VP1 10463. Strain 1470 produces a hybrid of toxins TcdB and TcsL. The strain produces TcdB-like cell contact and a TcsL-like enzymatic domain (morphological change and cell death like TcsL) (Voth, supra.; Chaves-Olarte E. et al, The Journal of biological chemistry, 1999, 274, no16, 11046-11052). As mentioned above, toxin B from reference strain 10463 inactivated small GTPases as Rho, Rac and Cdc-42. The impact is visible on electron microscopy with a modification of cellular aspect. Two types of cytopathic effects are described. The D-type is characterized by an arborized appearance of the cells whereas a spindle-like appearance is typical of the second type of cytopathic effect, the S-type (Mehlig, et al., FEMS Microbiol. Lett., 2001, 198:171-176). Toxin B of reference strain show D-type cytopathic effect as well as toxin A. Strains with lack of toxin A production, such as strain 1470 and strain 8864, produce toxin B with S-type cytopathic effect. Substrates for these toxins B are small GTPases Ras, Rac, Rap, Ral and Cdc-42. Both strains show variations in their toxin B gene (tcdB) compared to VP1 14063 tcdB gene. These variations explain the differences in substrate specificity. A difference in the N-terminal region of the tcdB of 1470 strain and VP1 10463 has been well documented (Von Eichel-Streiber et al, Mol Microbiol, 1995, 17: 313-321).

Another toxin B variant strain was discovered that produces functional toxin A. Thus, strain C34 is the first *C. difficile* strain that expresses a variant toxin B as 1470 and 8864, and a functional toxin A as reference type strain 14063 (Mehlig et al., supra.). This strain produces a toxin B with S-type cytopathic effect such as strain 1470 and 8864. C34 is the first *C. difficile* isolate coexpressing a D-type-inducing TcdA with an S-type-inducing TcdB molecule. The substrates of TcdA-C34 and the reference strain TcdA-10463 are identical (Rho, Rae and Cdc-42), and the substrates of TcdB-C34 and TcdA-1470 or 8864 are identical (Ras, Rac, Rap, Ral and Cdc-42). The tcdB sequence from C34 differs only in nucleotides from tcdB-1470 or 8864. Instead of having a deletion in tcdA that prevents toxin A production as strains 1470 and 8864, there is an inserted sequence in tcdA-C34. This small insertion does not have a negative effect on toxin A production. Nevertheless, in this strain, the S-type cytopathic effect on cells dominates over the D-type cytopathic effect (Mehlig et al., supra.).

To date, one variant strain has been described that produces a generally intact tcdB but a non-functional toxin B lacking a cytotoxic effect, and a functional toxin A having a cytotoxic effect. Toxinotyping data of this variant showed limited mutation in the Paloc and classified this strain in toxinotype IX (TcdA+/TcdB+/CDT+) (abstract, Maccannell et al, 2006). Recently, outbreaks of hypertoxigenic *C. difficile* strains have been reported in Canada and the United States. These isolates were positive for CDT binary toxin, had a deletion in the tcdC gene and produced greater amounts of toxins A and B (McDonald et al, New Engl. J. Med., December 2005, 353, no 23). The emergence of similar *C. difficile* isolates in the UK, Belgium and the Netherlands has also been described. The epidemic strain isolated in those countries was characterized as toxinotype III, North American PGEF 1 (NAP1), restriction endonuclease analysis group type B1 and PCR ribotype 027 (Kuijper E et al, document for European Centre for Disease prevention and Control, *Emergence of Clostridium difficile-associated disease in Canada, the United State of America and Europe*).

For *C. difficile* toxigenic strains, nucleotide sequence variations, deletions and duplications in the Paloc (tcdB and tcdA region) account for various types. A typing system has been developed which distinguishes the various types and classifies them as toxinotypes (1, 8, 9, 10, 11, 12, 13, 19). Toxinotyping involves detection of polymorphisms in the pathogenicity locus (Paloc) precisely in the tcdA and tcdB genes. There are now at least 24 toxinotypes (See Table 1). Strains in which the Paloc is identical to the reference strain VP1 10463 are referred as toxinotype 0. Not all variations of toxin genes affect toxin production. Strains of toxinotypes I-VII, TX, XII-XV and XVIII-XXIV produce both toxins A and B despite variations in their toxin genes (8, 11, 13, 19). Strains of toxinotype XI do not produce toxin A or B (13) whereas strains of toxinotypes VIII, X, XVI and XVII produce a functional toxin B but no toxin A (13). FIG. 2 describes well the relation between toxinotype and toxin expression. Strain 1470 belongs to toxinotype VIII and strain 8864 to toxinotype X. Most of the TcdA−/TcdB+ strains are known to belong to toxinotype VIII and produce a variant toxin B like strain 1470 while toxinotype X contains only strain 8864 (11).

TABLE 1

*Clostridium difficile* toxinotypes

| Toxinotype | Strain | Strain origin | Toxin production([1]) |
|---|---|---|---|
| 0 | VP1 10463 | USA | A+B+ CDT− |
| I | EX623 | Belgium | A+B+ CDT− |
| II | AC008 | France | A+B+ CDT− |
| IIIa | SE884 | Not available | A+B+ CDT+ |
| IIIb | R10278 | Not available | A+B+ CDT+ |
| IIIc | CH6230 | Not available | A+B+ CDT+ |
| IV | 55767 | Belgium | A+B+ CDT+ |
| V | SE881 | France | A+B+ CDT+ |
| VI | 51377 | Belgium | A+B+ CDT+ |
| VII | 57267 | Belgium | A+B+ CDT+ |
| VIII | 1470 | Belgium | A−B+ CDT− |
| IX | 51680 | Belgium | A+B+ CDT+ |
| X | 8864 | England | A−B+ CDT+ |
| XI a | IS58 | Not available | A−B− CDT+ |
| XI b | R11402 | Not available | A−B− CDT+ |
| XII | IS25 | Not available | A+B+ CDT− |
| XIII | R9367 | Not available | A+B+ CDT− |
| XIV | R10870 | England | A+B+ CDT+ |
| XV | R9385 | Not available | A+B+ CDT+ |
| XVI | SUC36 | Indonesia | A−B+ CDT+ |
| XVII | J9965 | Japan | A−B+ CDT+ |
| XVIII | GAI00166 | Korean | A+B+ CDT− |
| XIX | TR13 | Japan | A+B+ CDT− |
| XX | TR14 | Japan | A+B+ CDT− |
| XXI | CH6223 | USA | A+B+ CDT− |
| XXII | CH6143 | USA | A+B+ CDT− |
| XXIII | 8785 | Belgium | A+B+ CDT+ |
| XXIV | 597B | Kuwait | A+B+ CDT+ |

([1])A+ and B+ refers to production of toxin TcdA and TcdB; CDT+ refers to the presence of complete CDT locus.

The consensus sequence for the tcdB gene was determined using 6 available sequences in GenBank (See Appendix I). The first and seventh sequences in the tcdB alignment (SEQ ID NO: 1) (SEQ ID NO: 1) is are the reference strain VP1 14063 TcdA+/TcdB+. The second and third sequences in Appendix I (SEQ ID NOS 2 and 3, respectively) are two well-characterized TcdA−/TcdB+ strains (1470, second line and strain 8864, third line). The fourth line is another TcdA−/TcdB+ strain (5340) (SEQ ID NO: 4). The variant toxB and functional toxA strain C34 cluster 1-2 sequence (SEQ ID NO: 5) is shown in the fifth line, and the *C. sordellii* lethal toxin (TcsL) sequence (SEQ ID NO: 6) is shown in the sixth line as a specificity control. SEQ ID NO: 5 ends at nucleotide 1695. Thus, the six sequences in the alignment from nucleotides 1696 to 7095 (top to bottom) are SEQ ID NOS: 1, 2, 3, 4, 6, and 1, respectively. From nucleotides 7096 until the end of the sequence, SEQ ID NO: 1 is only shown once (top sequence), with the remaining sequences (top to bottom) being SEQ ID NOS: 1, 2, 3, 4, and 6, respectively. Certain regions of the tcdB gene are conserved among these different strains.

A positive culture for *C. difficile* without a toxin assay is not sufficient to make the diagnosis of *C. difficile*-associated disease. Thus, toxigenic *C. difficile* detection by a tissue culture cytotoxin assay is often considered the "gold standard." However, this assay is time consuming, as it implies an incubation period of at least 24 h. The present invention provides a real-time PCR assay targeting the *C. difficile* toxin gene tcdB that is rapid, sensitive, and specific, and allows detection of *C. difficile* directly from clinical samples, such stool samples.

SUMMARY OF THE INVENTION

The present invention provides primers and probes for detection of toxin-producing (toxigenic) strains of *C. difficile*. These primers and probes are shown in Tables 2-4, and methods of detecting toxigenic strains of *C. difficile* using these probes and primers.

One embodiment of the present invention is an oligonucleotide probe or primer up to about 100 nucleobases in length which is capable of hybridizing to a *C. difficile* toxin B (TcdB) gene, wherein said probe or primer comprises a sequence selected from the group consisting of SEQ ID NO: 1-33, or a sequence that exhibits at least about 85% identity to a sequence selected from the group consisting of SEQ ID NOS: 1-33. In one embodiment, the probe or primer has a sequence selected from the group consisting of SEQ ID NO: 1-33, or a sequence that exhibits at least about 85% identity to a sequence selected from the group consisting of SEQ ID NOS: 1-33. In another embodiment, the probe or primer has a sequence selected from the group consisting of SEQ ID NOS: 1-33. The present invention also provides a method for detecting the presence of a toxigenic strains of *C. difficile* in a biological sample, comprising contacting the sample with at least one pair of primers capable of binding to a *C. difficile* toxin B (TcdB) gene, in which each primer in the at least one pair of primers is up to about 100 nucleobases in length, and is capable of binding to a *C. difficile* toxin B (TcdB) gene, and in which each primer in the at least one pair of primers comprises a sequence shown in SEQ ID NOS: 1-33, or a sequence that exhibits at least about 85% identity to a sequence shown in SEQ ID NOS: 1-33; amplifying target nucleic acid from the sample; and detecting the presence or amount of an amplified product(s) as an indication of the presence of the toxigenic strain of *C. difficile* in said sample.

In one embodiment, the sample is a stool, sputum, peripheral blood, plasma, serum, lymph node, respiratory tissue or exudate sample. In another embodiment, the sample is contacted with one pair of primers. In yet another embodiment, the amplifying is carried out with polymerase chain reaction (PCR), ligase chain reaction (LCR), strand displacement amplification (SDA), replicase-mediated amplification or transcription-mediated amplification. Preferably, the amplifying is carried out using PCR. Types of PCR include AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR. In one embodiment, the PCT is quantitative real-time PCT (QRT-PCR). In another embodiment, each primer introduces exogenous nucleotide sequence which allows post-amplification manipulation of amplification products without a significant effect on amplification itself. In certain embodiments, the primer pair comprises SEQ ID NOS: 30 and 31 or 31 and 32. In one embodiment, each primer in the primer pair is flanked by complementary sequences comprising a fluorophore at the 5' end, and a fluorescence quencher at the 3' end.

DETAILED DESCRIPTION OF THE PREFERRED EMBODIMENT

Figure 1:
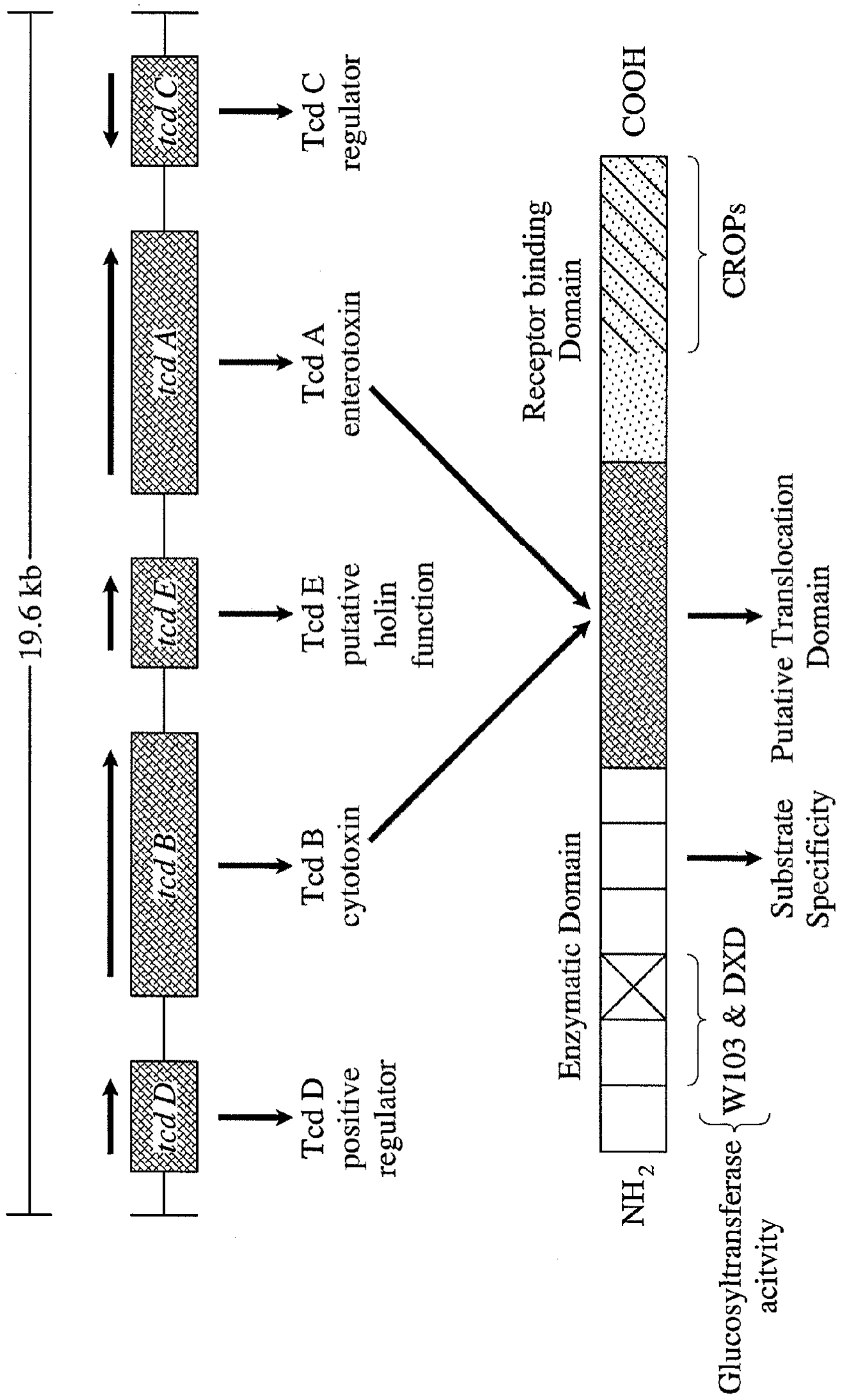
FIG. 1 shows the genetic arrangement of the *C. difficile* pathogenicity locus and proposed protein domain structure of the TcdA and TcdB genes.

The present invention relates to the detection of toxigenic strains of *Clostridium difficile* using particular primers and probes that bind to the toxin B (TcdB) gene of *C. difficile*. These primers and probes are used to amplify *C. difficile* nucleic acids in clinical samples to determine the presence of toxogenic strains.

As used herein, "template" refers to all or part of a polynucleotide containing at least one target nucleotide sequence.

As used herein, a "target nucleotide sequence" includes the nucleotide sequence of the final product having defined sequence and length, and may include other nucleotide sequences that are removed during post-amplification processing of the amplification product. Nucleotide sequences that are found in the target nucleotide sequence and later removed may include binding sites (annealing sites) for primers or probes, nucleotides involved in conversion of double-stranded DNA to single-stranded DNA, or sequences useful as recognition and/or cleavage sites for restriction endonucleases.

An "exogenous nucleotide sequence" as used herein, refers to a sequence introduced by primers or probes used for amplification, such that amplification products will contain exogenous nucleotide sequence and target nucleotide sequence in an arrangement not found in the original template from which the target nucleotide sequence was copied.

The template may be any polynucleotide suitable for amplification, where the template contains at least one target nucleotide sequence to be amplified. Suitable templates include DNA and RNA molecules, and may include polynucleotides having modified bases. Preferably, templates are genomic DNA, cDNA, or RNA molecules. In another preferred embodiment, methods disclosed herein can be used to amplify RNA templates directly, without reverse-transcribing the RNA template into cDNA.

By "clinical sample" is meant any tissue or material derived which may contain *C. difficile* nucleic acid, including, for example, stools (liquid or soft), sputum, peripheral blood, plasma, serum, biopsy tissue including lymph nodes, respiratory tissue or exudates, or other body fluids, tissues or materials. The sample may be treated to physically, chemically and/or mechanically disrupt tissue or cell structure, thus releasing intracellular components. Sample preparation may use a solution that contains buffers, salts, detergents and the like which are used to prepare the sample for analysis.

By "nucleic acid" is meant a polymeric compound comprising nucleosides or nucleoside analogs which have nitrogenous heterocyclic bases, or base analogs, linked together by nucleic acid backbone linkages (e.g., phosphodiester bonds) to form a polynucleotide. Conventional RNA and DNA are included in the term "nucleic acid" as are analogs thereof. The nucleic acid backbone may include a variety of linkages, for example, one or more of sugar-phosphodiester linkages, peptide-nucleic acid bonds, phosphorothioate or methylphosphonate linkages or mixtures of such linkages in a single oligonucleotide. Sugar moieties in the nucleic acid may be either ribose or deoxyribose, or similar compounds with known substitutions. Conventional nitrogenous bases (A, G, C, T, U), known base analogs (e.g., inosine), derivatives of purine or pyrimidine bases and "abasic" residues (i.e., no nitrogenous base for one or more backbone positions) are included in the term nucleic acid. That is, a nucleic acid may comprise only conventional sugars, bases and linkages found in RNA and DNA, or may include both conventional components and substitutions (e.g., conventional bases and analogs linked via a methoxy backbone, or conventional bases and one or more base analogs linked via an RNA or DNA backbone).

"Primer" means an oligonucleotide sequence that is designed to hybridize with a complementary portion of a target sequence, a probe, or a ligation product, and undergo primer extension. A primer functions as the starting point for the polymerization of nucleotides (Concise Dictionary of Biomedicine and Molecular Biology, (1996) CPL Scientific Publishing Services, CRC Press, Newbury, UK). A primer generally contains about sixteen to twenty-four nucleotides, but may contain up to about 50, 75 or 100 nucleotides. Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

The term "primer extension" means the process of elongating a primer that is annealed to a target in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand.

By "probe" is meant a nucleic acid oligomer that hybridizes specifically to a target sequence in a nucleic acid, under conditions that allow hybridization, thereby allowing detection of the target or amplified nucleic acid. The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe. Sequences are "sufficiently complementary" if they allow stable hybridization in appropriate hybridization conditions of a probe oligomer to a target sequence that is not completely complementary to the probe's target-specific sequence.

By "sufficiently complementary" is meant a contiguous nucleic acid base sequence that is capable of hybridizing to another base sequence by hydrogen bonding between a series of complementary bases. Complementary base sequences may be complementary at each position in the oligomer sequence by using standard base pairing (e.g., G:C, A:T or A:U) or may contain one or more residues that are not complementary (including abasic positions), but in which the entire complementary base sequence is capable of specifically hybridizing with another base sequence in appropriate hybridization conditions. Contiguous bases are preferably at least about 80%, more preferably at least about 90%, and most preferably 100% complementary to a sequence to which an oligomer is intended to hybridize. Those skilled in the art can readily choose appropriate hybridization conditions which can be predicted based on base sequence composition, or be determined by using routine testing (e.g., see Sambrook et al., Molecular Cloning, A Laboratory Manual, 2.sup.nd ed. (Cold Spring Harbor Laboratory Press, Cold Spring Harbor, N.Y., 1989).

The terms "duplex" means an intermolecular or intramolecular double-stranded portion of a nucleic acid which is base-paired through Watson-Crick, Hoogsteen, or other sequence-specific interactions of nucleobases. A duplex may consist of a primer and a template strand, or a probe and a target strand. A "hybrid" means a duplex, triplex, or other base-paired complex of nucleic acids interacting by base-specific interactions, e.g. hydrogen bonds.

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

In accordance with one aspect of the present invention, primers and/or probes are utilized to permit amplification of a *C. difficile* nucleic acid template containing a tcdB-derived target nucleotide sequence and to optionally introduce additional features into the amplification products. Each primer and/or probe contains a nucleotide sequence that is complementary to a region of target nucleotide sequence in the template, in order for each primer to bind (anneal) to the template. In one embodiment, at least one primer contains exogenous nucleotide sequence 5' (upstream) of the primer sequence complementary to the primer-binding target nucleotide sequence, with the result that each amplification product contains exogenous nucleotide sequence introduced by the primer.

Primers and/or probes having up to about 100 nucleotides comprising any of the primer and/or probe sequences described herein, and the use of these primers to detect the presence of the *C. difficile* TcdB gene in clinical samples using nucleic acid amplification-based methods (e.g., PCR), are also within the scope of the present invention. In addition, primers and/or probes that exhibit about 70%, 75%, 80%, 85%, 90%, 91%, 92%, 93%, 94%, 95%, 96%, 97%, 98% or 99% nucleic acid identity to any of the specific primers and/or probes described herein, and the use of these primers to detect the presence of the *C. difficile* TcdB gene in clinical samples using nucleic acid amplification-based methods, are also contemplated, as are primers and/or probes having up to about 100 nucleotides comprising any of these homologous sequences.

In another embodiment, two primers are used, where each primer introduces exogenous nucleotide sequence that allow post-amplification manipulation of amplification products without a significant effect on amplification itself. Alternately, more than two primers are used, where each primer introduces exogenous nucleotide sequence that allow post-amplification manipulation of amplification products without a significant effect on amplification itself. Primers for a particular embodiment may be designed by one of skill in the art according to well-known principles, for example as disclosed in Dieffenbach and Dveksler ("General Concepts For PCR Primer Design" in, PCR Primer: A Laboratory Manual, Dieffenbach and Dveksler, eds.)

Nucleic acid amplification refers to any known procedure for obtaining multiple copies of a target nucleic acid sequence or its complement or fragments thereof, using sequence-specific methods. Known amplification methods include, for example, Polymerase Chain Reaction (PCR), Ligase Chain Reaction (LCR), Strand Displacement Amplification (SDA), replicase-mediated amplification and transcription-mediated amplification.

PCR refers to a method well-known in the art for amplification of nucleic acid. PCR involves amplification of a target sequence using two or more extendable sequence-specific oligonucleotide primers that flank the target sequence. The nucleic acid containing the target sequence of interest is subjected to a precise program of multiple rounds of thermal cycling (denaturation, annealing and extension) in the presence of the primers, a thermostable DNA polymerase (e.g., Taq polymerase) and the four dNTPs, resulting in amplification of the target sequence. PCR uses multiple rounds of primer extension reactions in which complementary strands of a defined region of a DNA molecule are simultaneously synthesized by a thermostable DNA polymerase. At the end of each cycle, each newly synthesized DNA molecule acts as a template for the next cycle. During repeated rounds of these reactions, the number of newly synthesized DNA strands increases exponentially such that after 20 to 30 reaction cycles, the initial template DNA will have been replicated several thousand-fold or million-fold. Methods for carrying out different types and modes of PCR are thoroughly described in the literature, for example in "PCR Primer: A Laboratory Manual" Dieffenbach and Dveksler, eds. Cold Spring Harbor Laboratory Press, 1995, and by Mullis et al. in patents (e.g., U.S. Pat. Nos. 4,683,195, 4,683,202 and 4,800,159) and scientific publications (e.g. Mullis et al. 1987, Methods in Enzymology, 155:335-350) where the contents of each reference are hereby incorporated by reference in their entireties.

PCR generates double-stranded amplification products suitable for post-amplification processing. If desired, amplification products can be detected by visualization with agarose gel electrophoresis, by an enzyme immunoassay format using probe-based colorimetric detection, by fluorescence emission technology, or by other detection means known to one of skill in the art.

Methods for a wide variety of PCR applications are widely known in the art, and are described in many sources, for example, Ausubel et al. (eds.), Current Protocols in Molecular Biology, Section 15, John Wiley & Sons, Inc., New York (1994). Variations of PCR include AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR. These techniques are described, for example, at www.pcrlinks.com.

Real-time polymerase chain reaction, also called quantitative real time polymerase chain reaction (QRT-PCR), is used to simultaneously quantify and amplify a specific part of a given DNA molecule. It is used to determine whether a specific sequence is present in the sample; and if it is present, the number of copies of the sequence that are present. The term "real-time" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with fluorescence resonance energy transfer (FRET) probes measures fluorescent dye signal changes from cycle-to-cycle, preferably minus any internal control signals. The real-time procedure follows the general pattern of PCR, but the DNA is quantified after each round of amplification. Two common methods of quantification are the use of fluorescent dyes (e.g., Sybr Green) that intercalate into double-stranded DNA, and modified DNA oligonucleotide probes that fluoresce when hybridized with a complementary DNA.

LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.).

In strand displacement amplification, a double-stranded DNA target is denatured and hybridized with two primers, or the primers invade the DNA helix. The two primers contain an internal sequence for enzyme nicks to be placed in the newly formed DNA helix. The thermal stable DNA polymerase lacking a 5'→3' exonuclease activity, extends both primers. Generation of single stranded nicks creates new DNA extension sites and the hybridization of the first primer creates additional DNA extension sites for exponential DNA amplification.

Certain Embodiments of the invention include the following primers and probes (either RNA or DNA), that bind to the TcdB gene of *C. difficile.*

Design and Molecular Characterization of Probes and Primers

The design of primers and probes in any PCR diagnostic assay is always a compromise between sensitivity and specificity, and involves consideration of rapidity and hybridization temperature. The shortest amplicon is generally designed in order to maximize its accumulation and reduce the cycling time. The temperature difference between the melting temperature of the primers and the molecular beacon probe (defined below) is generally as high as possible. This can be achieved by varying the length and GC content of beacon stems. Such optimization of primers and probes requires a certain amount of theoretical data, obtained from database analysis and computations on nucleic acid sequences. A brief summary of relevant data is provided below.

Primers were designed using sequence databases and the software Oligo™ (version 6.0; National Biosciences). Primer design was based on melting temperature, GC content, the length of the amplicon, the ability to form as few hairpin structures as possible, their ability to form as few inter-secondary structures as possible with another primer molecule of the same sequence (homodimers), their ability to form as few inter-secondary structures as possible with other primers and probes (heterodimers), and their specificity for the toxB DNA gene sequence. Tm and GC % calculations were done using the Integrated DNA Technology (IDT) OligoAnalyzer 3.0 program, available on the IDT website (scitools.idtdna.com/Analyzer/oligocalc.asp). Parameters used were 0.2504 for all primers, 100 mM Na+ and DNA as target. To allow an overview of the primers of the BD GeneOhm™ Cdiff assay, the primers used to amplify the target are described in Table 2.

TABLE 2

| | NAME | SEQUENCE (5'-3') | POSITION | SEQ ID: |
|---|---|---|---|---|
| (1) | VJ-tcdB-F | TAATAGAAAACAGTTAGAAA | 12-31 | 7 |
| | VJ-tcdB-R | TCCAATCCAAACAAAATGTA | 312-293 | 8 |
| (2) | NP1-tcdB-F2 | TATATAAATCAATGGAAAGATGTAAATAGT | 340-369 | 9 |
| | NP1-tcdB-F1 | TAGTAATGCATTTTTGATAAACACATTGAAA | 396-426 | 10 |
| | NP1-tcdB-R2 | TTTGAAAGATATGTCTTTACAATATC | 635-610 | 11 |
| | NP1-tcdB-R1 | TTCTTCAAAGTTTCTAACATCATTTCCAC | 745-707 | 12 |
| (3) | tcdB-2667 (MGB-tcdB-F) | ATATCAGAGACTGATGAG | 2665-2682 | 13 |
| | tcdB-2746 (MGB-tcdB-R) | TAGCATATTCAGAGAATATTGT | 2767-2746 | 14 |
| (4) | NK-104 (NK-tcdB-F) | GTGTAGCAATGAAAGTCCAAGTTTACGC | 2945-2972 | 15 |
| | KERLA-tcdB-2873-F1 | CTTTAAATGCTGCATTTTTTATACAATC | 2873-2900 | 16 |
| | KE-tcdB-F | GAAAGTCCAAGTTTACGCTCAAT | 2955-2977 | 17 |
| | KENP-tcdB-F1 | GCTCAATTATTTAGTACTGGTTTAAATAC | 2971-2999 | 18 |
| | KENP-tcdB-3102-R1 | TGCACCTAAACTTACACCATCTATAATA | 3129-3102 | 19 |
| | KE-tcdB-R | GCTGCACCTAAACTTACACCA | 3131-3111 | 20 |
| | NK-105 (NK-tcdB-R) | CACTTAGCTCTTTGATTGCTGCACCT | 3148-3123- | 21 |
| | NKMER-tcdB-R3 | CTATTTCTTGTCTTAATAATGGGTCAC | 3181-3155 | 22 |
| (5) | SP-tcdB-F | GAAGGTGGTTCAGGTCATAC | 3517-3536 | 23 |
| | EF-tcdB-F1 | AATGGAAGGTGGTTCAGGTC | 3513-3542 | 24 |
| | EF-tcdB-R1 | CTTAAACCTGGTGTCCATC | 3722-3704 | 25 |
| | SP-tcdB-R | CATTTTCTAAGCTTCTTAAACCTG | 3736-3713 | 26 |
| (6) | JLP-tcdB-F | GGAAAAGAGAATGGTTTTATTAA | 4405-4427 | 27 |
| | JLPNP-tcdB-F | ACAAAAGAAGGTTTATTTGTATG | 4435-4457 | 28 |
| | JLP-tcdB-R | ATCTTTAGTTATAACTTTGACATCTT T | 4566-4540 | 29 |

F = FORWARD; R = REVERSE

Primers KERLA-tcdB-2873 and KENP-tcdB-3102 were designed for *Clostridium difficile* toxin B gene amplification. Their characteristics are shown in Table 3. This simplex allows the amplification of the target. This primer set was chosen because both have similar GC contents and melting temperatures ($T_m$). Furthermore, the amplicon generated with these primers is 257 bp long for the toxin B gene target, which is suitable for a real-time PCR assay using molecular beacon probes. The primers KERLA-tcdB-2873 and KENP-tcdB-3102 also serve as primers for the internal control pDIFFa.

TABLE 3

| Primer | Sequence | Tm (° C.) | Length (bp) | GC% | Orientation | Amplicon size (bp) |
|---|---|---|---|---|---|---|
| KERLA-tcdB-2873 | 5'CTTTAAATGCTGCATTTTTTATACAATC 3' (SEQ ID NO: 16) | 56.8 | 28 | 25.0 | Forward | 257 |
| KENP-tcdB-3102 | 5'TGCACCTAAACTTACACCATCTATAATA 3' (SEQ ID NO: 19) | 59.6 | 28 | 32.1 | Reverse | |

Molecular beacons are single-stranded oligonucleotide hybridization probes that form a stem-and-loop structure. The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo a conformational change that enables them to fluoresce brightly.

In the absence of targets, the probe is dark, because the stem places the fluorophore so close to the nonfluorescent quencher that they transiently share electrons, eliminating the ability of the fluorophore to fluoresce. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, restoring fluorescence.

Delta G at annealing temperature <0.

No mismatches between probe and appropriate target.

Temperature difference between the Tm of the primers and the molecular beacon as high as possible.

Sequence alignments do not demonstrate cross reactivity between probes nor between probes and primers.

Molecular Beacons NK-toxB-B34-A0 and Sign-B4-B0 (Table 4) were chosen because their characteristics correspond to the best compromise between all established theoretical criteria. The Sign-B4-B0 probe hybridizes with the forward strand of the internal control amplicons, while NK-toxB-B34-A0 hybridizes with the reverse strand of the *C. difficile* toxin B gene. For detection of toxin B gene amplicons, the molecular beacon NK-toxB-B34-A0 bears the fluorophore 5'-carboxyfluorescein (FAM) at its 5' end and the nonfluorescent quencher moiety dabcyl chloride (DABCYL) at its 3' end. For detection of the IC amplicons, the molecular beacon Sign-B4-B0 includes the fluorophore tetrachlorofluorescein (TET) at its 5' end, and the nonfluorescent quencher moiety DABCYL at its 3' end. The NK-toxB-B34-A0 probe provides the positive signal in the assay and Sign-B4-B0 determines the validity of the PCR reaction in the assay. Their characteristics are shown in Table 4.

TABLE 4

| Probe | Target | Fluorophore | Size (nucleotides) | GC% | Sequence* |
|---|---|---|---|---|---|
| NK-toxB-B34-A0 | tcdB | FAM | 32 | 43.8 | 5' cgGTTGTTGAATTAGTATCAACTGCAcaaccg 3' (SEQ ID NO: 30) |
| Sign-B4-B0 | pDIFFa | TET | 41 | 63 | 5' ccggcGATGCCTCTTCACATTGCTCCACCTTTCCTcgccgg 3' (SEQ ID NO: 31) |

*The stem sequences are in small letters as the hybridizing sequences are in capital letters. Some nucleotides from the hybridizing sequence can also be part of the stem sequence and are thus underlined.

Molecular beacons can be used as amplicon detector probes in diagnostic assays. Because nonhybridized molecular beacons are dark, it is not necessary to isolate the probe-target hybrids to determine the number of amplicons synthesized during an assay. Molecular beacons are added to the assay mixture before carrying out gene amplification and fluorescence is measured in real time. The assay tube remains sealed. Consequently, the amplicons cannot escape to contaminate untested samples. Furthermore, the use of molecular beacons provides an additional level of specificity. Because it is very unlikely that false amplicons or primer-dimers possess target sequences for the molecular beacons, the generation of fluorescence is exclusively due to the synthesis of the intended amplicons.

Molecular Beacon Design

Molecular beacons were designed to target the tcdB sequence and the internal control pDIFFa Using sequence databases and the software Oligo™ (version 6.0; National Biosciences). The different criteria taken into consideration when selecting molecular beacon probes are summarized below Contain conserved sequence only from species to detect (or from species characteristics to detect), and shows the required specificity.

Probe length ~20 to 30 nucleotides.

Probe does not hybridize on parts of the amplified target showing secondary structures.

Required Tm according to the assay.

GC content of 60% to 80%

Only one structure (hairpin loop) at both synthesis and annealing temperatures.

Formation of Hairpin Structures

The proper design of an assay also involves the verification of potential problems for the amplification reaction. The amplification efficiency can be greatly affected by secondary structures and mismatches between primers, probes and their respective targets. To prevent such occurrences, the ability of all primers to form hairpin structures was evaluated with IDT OligoAnalyzer 3.0 software available on IDT's website. Parameters used were 0.25 μM of each primer, 100 mM $Na^+$, 5.5 mM $MgCl_2$, target DNA, hybridization temperature of 57° C. Since the hybridization depends on the thermodynamic characteristics of the molecules involved, secondary structures or undesired matches can thus be predicted and avoided. In addition, in all reactions in a PCR assay occurring in solution, the Gibbs free energy (noted $\Delta G$ and expressed in kcal/mol) is predictive of whether or not a match is likely to occur. $\Delta G$ negative values are indicative of the formation of a proposed structure or match, whereas positive values of $\Delta G$ indicate that a proposed structure is thermodynamically unstable and a match is unlikely to occur. Two hairpin structures can be formed with primer KERLA-tcdB-2873 ($\Delta G$=0.86 and 0.89 kcal/mol), and two hairpin structures can be formed with primer KENP-tcdB-3012 ($\Delta G$=1.9 and 2.35 kcal/mol). These structures are all thermodynamically unstable (positive $\Delta G$).

Figure 2A:
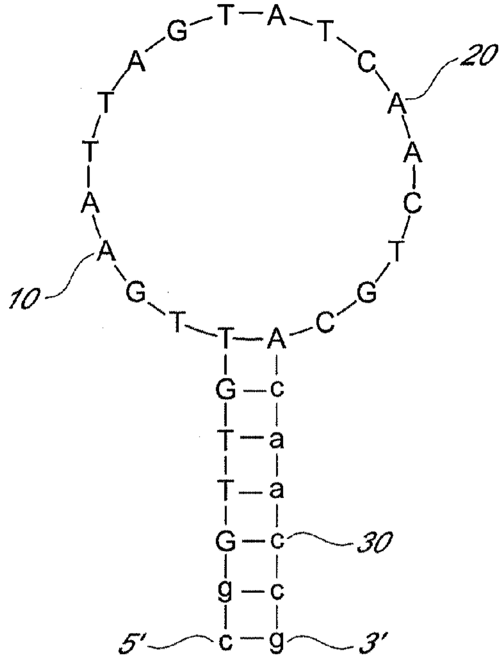
FIG. 2*a* is a schematic diagram showing the hairpin structure formed with the NK-toxB-B34-A0 target probe (SEQ ID NO:32).
Figure 2B:
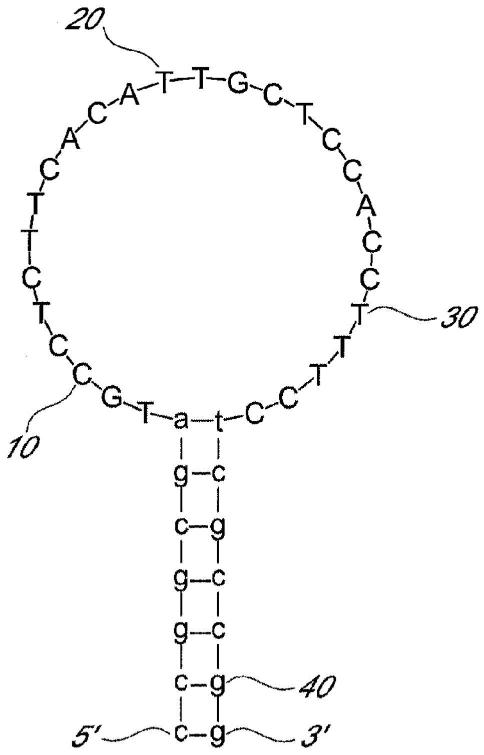
FIG. 2*b* is a schematic diagram showing the hairpin structure formed with the Sign-B4-B0 internal control probe (SEQ ID NO:33).
Figure 1:
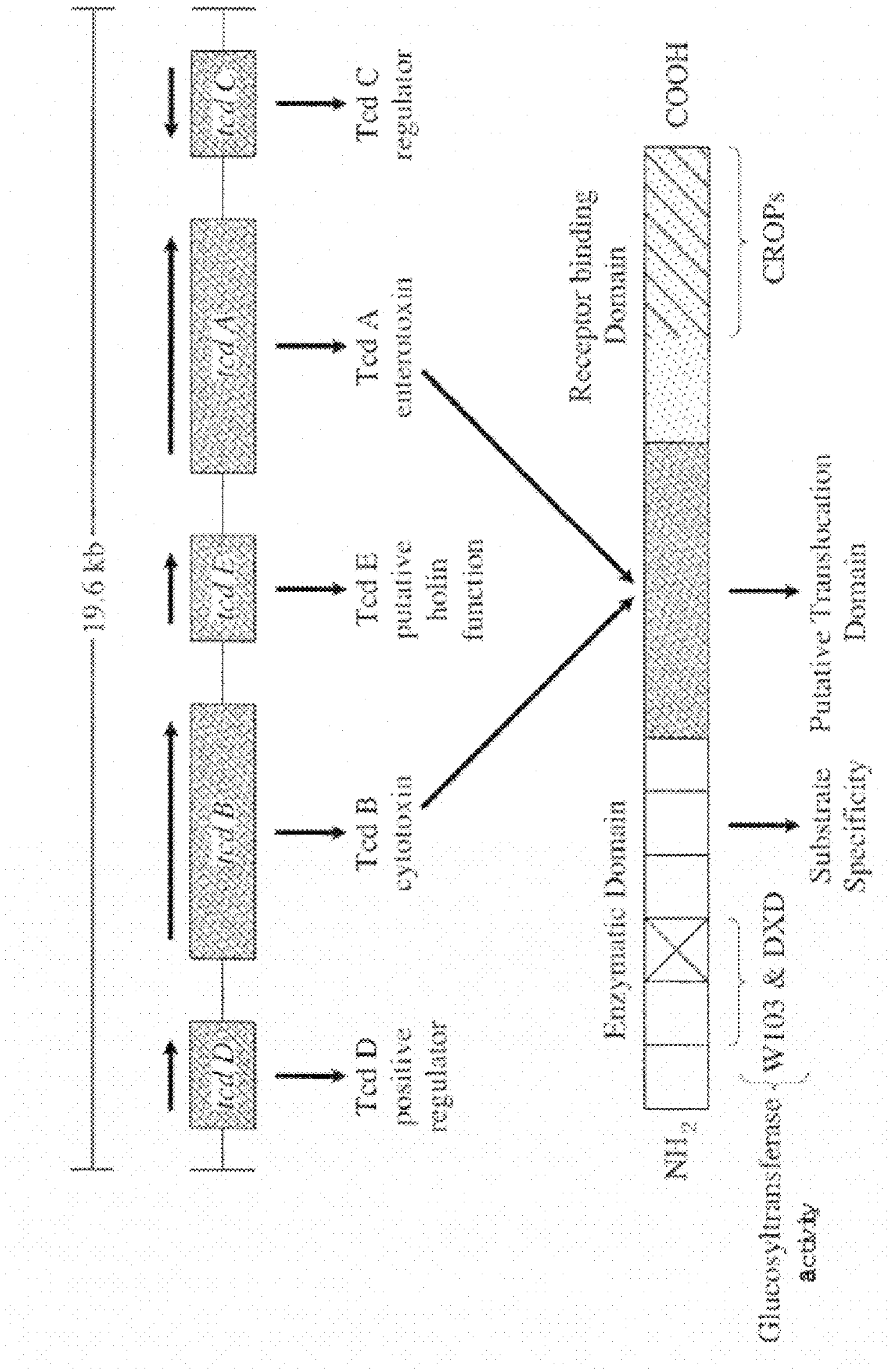

The NK-toxB-B34-A0 target probe and Sign-B4-B0 internal control probe molecule each has an oligonucleotide probe sequence flanked on each side by complementary sequences (arms), carrying a fluorophore at its 5' end and a fluorescence quencher at its 3' end. In a closed conformation, the arms form a stem and the probe sequence is located in a hairpin loop (FIGS. 2*a* and 2*b*). In this conformation the fluorescence is quenched. However, when hybridizing with the target DNA, the hairpin structure unfolds and allows fluorescence. For each probe, structure was determined at two temperatures using The Bioinformatics Center at Rensselaer and Wadsworth tools (DNA folding in applications section); this web server uses mfold (version3.1) by Zuker and Turner (Zuker, *Nucleic Acids Res.* 31 (13), 3406-15, 2003). First, the probe structure at the synthesis temperature and salt conditions was determined (10 mM $Na^+$ and 20° C. without $Mg^{2+}$) and then the structure at the annealing temperature and salt conditions of the PCR assay was determined (100 mM $Na^+$, 57° C. and 5.5 mM $Mg^{2+}$). Only one structure was obtained for target probe as well as for IC probe (synthesis conditions and PCR conditions (see FIGS. 2*a* and 2*b*)). No stable probe dimer was identified.

The ability of all primers and probes to form self dimers (homodimers) or duplexes with another primer or probes of the assay (heterodimers) was evaluated with the IDT OligoAnalyzer 3.0 software available on IDT's website. Parameters used for the analysis were 0.25 μM of each primer, 100 mM $Na^+$ and DNA as target. Homoduplexes of primers involving less than 7 consecutive base pairs corresponding to 25% of the total sequence (28 bp length) are very unlikely to form. Two structures formed with KERLA-tcdB-2873 involve 6 consecutive bases corresponding to 21% of the size of the primer. This is not enough to generate a stable duplex (Table 5). With KENP-tcdB-3102, hybridizations could occur with only 4 consecutive base pairs (14%). With probes, 17% and 22% of the total sequence of Sign-B4-B0 (7/41 bp) and NK-toxB-B34-A0 (7/32 bp), respectively, could be used to form homoduplexes. This is not sufficient to create stable structures. In the same way, heteroduplexes involving a number of consecutive nucleotides lower than 25% of the shortest sequence size are very unlikely to form (Table 5). Consequently, all the structures able to be formed will be unstable and 18% is the greatest percentage met.

TABLE 5

| | KERLA-tcdB-2873 (length 28 bp) | | KENP-tcdB-3102 (length 28 bp) | | Sign-B4-B0 (length 41 bp) | | NK-toxB-B34-A0 (length 32 bp) | |
|---|---|---|---|---|---|---|---|---|
| | Consecutive nucleotide duplexes | Delta G | Consecutive nucleotide duplexes | Delta G | Consecutive nucleotide duplexes | Delta G | Consecutive nucleotide duplexes | Delta G |
| KERLA-tcdB-2873 | 6 | −10.46 | | | | | | |
| (length 28 bp) | 6 | −8.74 | | | | | | |
| | 4 | −7.05 | | | | | | |
| KENP-tcdB-3102 | 4 | −7.05 | 4 | −7.05 | | | | |
| (length 28 bp) | 5 | −5.34 | 4 | −3.40 | | | | |
| | 3 | −5.09 | 3 | −2.91 | | | | |
| Sign-B4-B0 | 4 | −6.57 | 3 | −5.09 | 7 | −18.08 | | |
| (length 41 bp) | 4 | −5.37 | 3 | −5.09 | 4 | −9.75 | | |
| | 4 | −5.37 | 4 | −5.00 | 4 | −9.75 | | |
| NK-toxB-B34-A0 | 4 | −7.05 | 4 | −7.05 | 3 | −6.68 | 7 | −13.26 |
| (length 32 bp) | 4 | −5.24 | 4 | −4.50 | 3 | −6.68 | 4 | −7.05 |
| | 3 | −5.09 | 3 | −4.41 | 3 | −6.68 | 5 | −6.82 |

In one embodiment, to ensure the required specificity, the assay primers do not generate any amplified product with sequences other than *C. difficile*. Thus, the potential hybridization of the primers with non-*C. difficile* sequences was tested. Sequences homologous to each assay primer were identified using BLAST searches (version 2.2.15) from the GenBank databases. The likelihood of amplifying non-target sequences was then evaluated according to the following criteria:

- the hybridization of each primer pair on different strands or the hybridization of one given primer at two sites on the same target
- the number of nucleotides complementary to the target sequence. Namely, the last 2 nucleotides of primers 3' end should hybridize to the target to allow primer extension.
- the length of the DNA fragment generated by the primer pair. Fragments above 3 kb are well outside rapid PCR and molecular beacon detection technology's limits.

Results of these searches are summarized in Table 6. For both primers, only Toxin B gene sequence from *C. difficile* strains showed 100% identity with primer sequences.

TABLE 6

| Primer name | Primer length (nucleotides) | Total identified | tcdB 100% identity | Source (n) |
|---|---|---|---|---|
| KERLA-tcdB-2873 | 28 | 103 | 6 | *Clostridium difficile* 630 complete genome (AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |
| KENP-tcdB-3102 | 28 | 50 | 6 | *Clostridium difficile* 630 complete genome(AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |

To ensure that probes hybridized only with *C. difficile* amplicons, and had the required sensitivity, the potential hybridization of the probes with non-*C. difficile* sequences was tested. Sequences homologous to each of the assay probes were identified using BLAST searches (version 2.2.15) of the GenBank databases. Results of these searches are summarized in Table 7. For the target probe, only the Toxin B gene sequence from *C. difficile* strains showed 100% identity with the probe sequence. For the internal control probe, only the *Drosophila melanogaster* sequence showed 100% identity with the probe sequence. The Internal control probe was designed from the *Drosophila melanogaster* sequence.

TABLE 7

| | | Number of Identified sequences | | |
|---|---|---|---|---|
| Probe name | Probe length (nucleotides) | Total identified | 100% homology with target[1] | Source (n) |
| NK-toxB-B34-A0 | 24 | 23 | 6 | *Clostridium difficile* 630 complete genome (AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |
| Sign-B4-B0 | 27 | 77 | 14[2] | *Drosophila melanogaster* genomic scaffold 211000022280790<br>*Drosophila melanogaster* genomic scaffold 211000022280724<br>*Drosophila melanogaster* genomic scaffold 211000022280794<br>*Drosophila melanogaster* genomic scaffold 211000022280749<br>*Drosophila melanogaster* chromosome 3L, complete sequence<br>*Drosophila melanogaster* chromosome 2R, complete sequence<br>*Drosophila melanogaster* genomic scaffold 211000022280741<br>*Drosophila melanogaster* genomic scaffold 211000022280785<br>*Drosophila melanogaster* genomic scaffold 211000022280616<br>*Drosophila melanogaster* clone BACR11B22, complete sequence<br>*Drosophila simulans* w gene, retrotransposons ninja1, ninja2, ninja3, strain: w[mky]<br>*Drosophila simulans* w gene, retrotransposon ninja, strain: w[apl]<br>*Drosophila simulans* retrotransposon ninja DNA<br>*Drosophila melanogaster* retrotransposon aurora DNA |

[1]Toxin B gene for NK-toxB-B34-A0 or internal control signature sequence for Sign-B4-B0

[2]The Internal control was designed from *D. melanogaster* sequences

Specificity and Sensitivity

Twenty-two different *C. difficile* toxinotypes were tested with the probes shown in Table 4. Positive results were obtained for all toxinotypes, but not for any related species, *C. sordelli, C. difficile* A−/B− strain or non-toxigenic *C. difficile* strain. Thus, the probes are specific to toxigenic strains of *C. difficile*.

Real-time PCR was performed under standard conditions using *C. difficile* DNA obtained from liquid or soft human stool samples using the primers shown in Table 3. The real-time PCR assay was performed as described below.

Real-Time PCR Assay

Lyophilized reagents were reconstituted with 225 µl diluent to provide the following buffer used for the real-time PCR assay: 116 mM Tris-HCl, pH 8.3, 11.6 mM KCl, 3.48 mM $MgCl_2$, 5.8 mM $NH_2SO_4$, and subsequently divided into 25 µl aliquots. 0.5, 2.5, 5, 10 or 20 copies of *C. difficile* template DNA was added to each of 5 replicate reactions.

The PCR assay was run in a SMART CYCLER™ PCR machine under the following conditions: 60° C. for 6 see followed by 95° C. for 900 sec, followed by 45 cycles of 95° C. for 5 seconds, 63° C. for 10 see and 72° C. for 20 sec. The sensitivity and specificity obtained were 96.6% and 97.4%, respectively.

APPENDIX I

*C. difficile* tcdB sequence

```
  -5 ATTTTATGAG TTTAGTTAAT AGAAAACAGT TAGAAAAAAT GGCAAATGTA AGATTTCGTA CTCAAGAAGA TGAATATGTT GCAATATTGG ATGCTTTAGA
          ..... .......... .......... .......... .......... .........G T...G..... .........A ........A. ....A.....
          ..... .......... .......... .......... .......... .........G T...G..... .........A ........A. ....A.....
          ..... .......... .......... .......... .......... .........G T...G..... .........A ........A. ....A.....
          ..... C.C....... .......... .......... .......... .........G T......... .........A ........A. ....A.....
          ....g c........c .a.gcc..at ..c....... ..t.t..... .g........ t......... ...g..c..a ........aa .....c....
  -5 ATTTTATGAG TTTAGTTAAT AGAAAACAGT TAGAAAAAAT GGCAAATGTA AGATTTCGTA CTCAAGAAGA TGAATATGTT GCAATATTGG ATGCTTTAGA

  96 AGAATATCAT AATATGTCAG AGAATACTGT AGTCGAAAAA TATTTAAAAT TAAAAGATAT AAATAGTTTA ACAGATATTT ATATAGATAC ATATAAAAAA
     .......... .......... .A........ ...T.....G ...C...... .......... ...C...... .......C.. .......... ..........
     .......... .......... .A........ ...T.....G ...C...... .......... ...C...... .......C.. .......... ..........
     .......... .......... .A........ ...T.....G ...C...... .......... ...C...... .......CC. .......... ..........
     .......... .......... .A........ ...T.....G ...C...... .......... ...C...... .......CC. .......... ..........
     .........c ..c....... .a...g.... ...t.....g .......... ....g..... .....a.c.c .......a.. .cctga.c.c ..........
  96 AGAATATCAT AATATGTCAG AGAATACTGT AGTCGAAAAA TATTTAAAAT TAAAAGATAT AAATAGTTTA ACAGATATTT ATATAGATAC ATATAAAAAA

 196 TCTGGTAGAA ATAAAGCCTT AAAAAAATTT AAGGAATATC -TAGTTACAGA AG-TATTAGAG CTA-AAGAATA ATAATTTAAC TCCAGTTGAG AAAAATTTAC
     ......C... .......... .......... ..A..G..-. T......T..- ..A.......A T..G..-.... GC........ ......C... ..........
     ......C... .......... .......... ..A..G..-. T......T..- ..A.......A T..-..A.... GC........ ......C... ..........
     ......C... .......... .......... ..A..G..-. T.........- ..A.......A T..-..A.... GC........ ......C... ..........
     .....CC... .......... .......... ..A..G..-. T.......... ..-.......A T..-..A.... GC........ ......C... ..........
     .....a..g. .......... .......... ..a....... -..ac..tg.. ..-........ ...-..a.... ...g.c.... .......c..a .........
 196 TCTGGTAGAA ATAAAGCCTT AAAAAAATTT AAGGAATATC -TAGTTACAGA AG-TATTAGAG CTA-AAGAATA ATAATTTAAC TCCAGTTGAG AAAAATTTAC

 296 ATTTTGTTTG GATTGG GGT CAAATAAATG ACACTGCTAT TAATTATATA AATCAATGGA AAGATGTAAA TAGTGATTAT AATGTTAATG TTTTTTATGA
     .....A.A.. .........G .......... .T........ .......... .......... .......... ......C... .......... ..........
     .....A.A.. .........G .......... .T........ .......... .......... .......... ......C... .......... ..........
     .....A.A.. .........G .......... .T........ .......... .......... .......... ......C... .......... ..........
     .....A.A.. .........G .......... .T........ .......... .......... .......... ......C... .......... ..........
     .....a.a.. .........a .......... ....c..... c..c...... .......... .......... ...c...... .ca.....ag ..........
 296 ATTTTGTTTG GATTGGAGGT CAAATAAATG ACACTGCTAT TAATTATATA AATCAATGGA AAGATGTAAA TAGTGATTAT AATGTTAATG TTTTTTATGA
```

APPENDIX I-continued

*C. difficile* tcdB sequence

```
396  TAGTAATGCA TTTTTGATAA ACACATTGAA AAAAACTGTA GTAGAATCAG  CAAT-AAATCA TACACTTGAA TCATTTAGAG AAAACTTAAA TGACCCTAGA-
     .......... .......... .......... .......A.. A.........  ..-.C...... ...C...... .......... ....T..... ...T...-..A
     .......... .......... .......... .......A.. A.........  ..-.C...... ...C...... .......... ....T..... ...T...-..A
     .......... .......... .......... .......A.. A.........  ..-.C...... ...T...... .......... ....T..... ...T...-..A
     .......... .......... .......... .......A.. A.........  ..-.C...... ...T...... .......... ....T..... ...T...-..A
     .......... .......... .......... g......a.t ..t..g....  ...c-....a. ...t.....g .......... .......... .......-..a
396  TAGTAATGCA TTTTTGATAA ACACATTGAA AAAAACTGTA GTAGAATCAG  CAAT-AAATGA TACACTTGAA TCATTTAGAG AAAACTTAAA TGACCCTAGA-

496  TTTGACTATA ATAAATTCTT CAGAAAACGT ATGGAAATAA TTTATGATAA  ACAGAAAAAT TTCATAAACT ACTATAAAGC TCAAAGAGAA GAAAATCCTG
     ...A..C.C. C.GC...T.. .......... ...C...... .C........  ....C..... .......T.. .......... .....A.... ..........
     ...A..C.C. C.GC...T.. .......... ...C...... .C........  ....C..... .......T.. .......... .....A.... ..........
     ...A..C.C. C.GC...T.. .......... ...C...... .C........  ....C..... .......T.. .......... .....A.... ..........
     ...A..C.C. C.GC...T.. .......... ...C....C. .C........  ....C..... .......T.. .........T .....A.... ..........
     ..c..t.... .......t.a t......... .......... .a........  ...a...c.. ..t...g.t. .t.....gt. ...g.t.... ..g.......
496  TTTGACTATA ATAAATTCTT CAGAAAACGT ATGGAAATAA TTTATGATAA  ACAGAAAAAT TTCATAAACT ACTATAAAGC TCAAAGAGAA GAAAATCCTG

596  AACTTATAAT TGATGATATT GTAAAGACAT ATCTTTCAAA TGAGTATTCA  AAGGAGATAG ATGAACTTAA TACCTATATT GAAGAATCCT TAAATAAAAT
     .C........ .......... .......... .......... C.........  .....T.... .......... .G.T...... .....G..A. ....C...G.
     .C........ .......... .......... .......... C.........  .....T.... .......... .G.T...... .....G..A. ....C...G.
     .C........ .......... .......... .......... C.........  .....T.... .......... .G.T...... .....G..A. ....C...G.
     .C........ .......... .......... .......... C.........  .....T.... .......... .G.T...... .....G..A. ....C...G.
     ..t....... ....a..... a....a.... ....c..... ..........  ..a..cc... .t.cc..... ..ag...... ........t. ..........
596  AACTTATAAT TGATGATATT GTAAAGACAT ATCTTTCAAA TGAGTATTCA  AAGGAGATAG ATGAACTTAA TACCTATATT GAAGAATCCT TAAATAAAAT

696  TACACAGAAT AGTGGAAATG ATGTTAGAAA CTTTGAAGAA TTTAAAAATG  GAGA-GTCATT CAACTTATAT GAACAAGAGT TGGTAGAAAG GTGGAAT-TTA
     C...G.A... .......... .......... .......... .......C..  ....A..-... ...T...... .......... .A........ A......C..-
     C...G.A... .......... .......... .......... .......C..  ....A..-... ...T...... .......... CA........ A......C..-
     C...G.A... .......... .......... .......... .......C..  ....A..-... ...T...... .......... .A........ A......C..-
     C...G.A... .......... .......... .......... .......C..  ....A..-... ...T...... .......... .......... A......C..-
     ...tgct... .a...t.... ..a.c..... tc.a...a.. ...gctga..  ag..-t.tgg. c.ga...... a.t.....g. .a........ a......-..g
696  TACACAGAAT AGTGGAAATG ATGTTAGAAA CTTTGAAGAA TTTAAAAATG  GAGA-GTCATT CAACTTATAT GAACAAGAGT TGGTAGAAAG GTGGAAT-TTA
```

APPENDIX I-continued

*C. difficile* tcdB sequence

```
796   GCTGCTGCTT CTGACATATT AAGAATATCT GCATTAAAAG AA-ATTGGTGG TA-TGTATTTA GATGTTGATA TGTTACCAGG AATACAACCA GACTTATTTG
      ....G...A. ....T..... ....G.CG.. AT...G...- ..T.......  -.G.C...C.. .......... .......... ......C... ..T......A
      ....G...A. ....T..... ....G.CG.. AT...G...- ..T.......  -.G.C...C.. .......... .......... ......C... ..T......A
      ....G...A. .C..T..... ....G.CG.. AT...G...- ..T.......  -.G.C...C.. .......... ....G..... ......C... ..T......A
      ....G...A. ....T..... ....G.CG.. AT...G...- ..T.......  -.G.C...C.. .......... .......... ......C... ..T......A
      .......... .......... .c........ atg....... ..-ga.....  .-g.a...... ........c. .g........ t......... ..t......a
796   GCTGCTGCTT CTGACATATT AAGAATATCT GCATTAAAAG AA-ATTGGTGG TA-TGTATTTA GATGTTGATA TGTTACCAGG AATACAACCA GACTTATTTG

896   A-GTCTATAGA GAAACCT-AGT TCAGTAA---CAG -TGGATTTTTG GGAA-ATGACA AAGTTAGAAG CTATAATGAA ATACAAAGAA TATATACCAG AATATACCTC
      .A.A-....A. T..G...G.-. .......AGA... C..T.GA..-. ....G.-..TG C......... .C........ .C.T...... .......... .......T..
      .A.A-....A. T..G...G.-. .......AGA... C..T.GA..-. ....G.-..TG C......... .C........ .C.T...... .......... .......T..
      .A.A-....A. T..G...G.-. .......AGA... C..T.GA..-. ....G.-..TG C......... .C........ ...T...... .......... .......T..
      .A.A-....A. T..G...G.-. .......AGA... C..T.GA..-. ....G.-..TG C......... .C........ ...T...... .......... .......T..
      .-.a.....a. c..g...-ga. ..ga......c.a -atacaag... ....-....t. ........g. .......... ...t..g... .......... gg.....g..
896   A-GTCTATAGA GAAACCT-AGT TCAGTAA---CAG -TGGATTTTTG GGAA-ATGACA AAGTTAGAAG CTATAATGAA ATACAAAGAA TATATACCAG AATATACCTC

996   AGAA-CATTTT GACATGTTAG ACGAAGAAGT TCAAAGTAGT TTTGAATCTG -TTCT-AGCTTC TAAGTCAGAT AAATCAGAAA TATTCTCATC ACTTGGTGAT
      -...A...... ..T.CA..G. .T........ .........C .......... -..T.-...... ......T... ..G....... ....T.T.C. ...A..A...
      -...A...... ..T.CA..G. .T........ .........C .......... -..T.-...... ......T... ..G....... ....T.T.C. ...A..A...
      .A..-...... ..T.CA..G. .T........ .........C .......... -....-...... ......T... ..G....... ....T.T.C. ...A..A.G.
      .A..-...... ..T.CA..G. .T........ .........C .......... -....-...... ......T... ..G....... ....T.T.C. ...A..A...
      .-..ga..... .......... .t........ ....c.c... .......... c..-.a..-... ...a...... ..g....... .t..t.tgc. .....a....
996   AGAA-CATTTT GACATGTTAG ACGAAGAAGT TCAAAGTAGT TTTGAATCTG -TTCT-AGCTTC TAAGTCAGAT AAATCAGAAA TATTCTCATC ACTTGGTGAT

1096  ATGGAGGCAT CACCACTAGA AGTTAAAA-TT GCATTTAATA GTAAGGGT--AT TATAAATCAA GGGC-TAATTT CTGTGAAAGA CTCATATTGT AGCAATTTAA
      ..A....T.. ....TT.... ...A....-.. ......GCC. --....T.CT.. .......... .CT.-...... ...CA..... T......... ..TG.C...C
      ..A....T.. ....TT.... ...A....-.. ......GCC. --....T.CT.. .......... .CT.-...... ...CA..... T......... ..TG.C...C
      ..A....T.. ....TT.... ...-....G.. ......GCC. --....T.CT.. ....G..... .CT.-...... ...CA..... .......... ..TG.C...C
      ..A....T.. ....TT.... ...A....-.. ......GCC. --....T.CT.. .......... .CT.-...... ...CA..... .......... ..TG.C...C
      ..aa.a.t.. .c..gt.... ...a....-.. ......gcc. a...ctc.--g. .......... -.c.t...... ..t.a..... t..c...... ..tg.....g
1096  ATGGAGGCAT CACCACTAGA AGTTAAAA-TT GCATTTAATA GTAAGGGT--AT TATAAATCAA GGGC-TAATTT CTGTGAAAGA CTCATATTGT AGCAATTTAA
```

APPENDIX I-continued

C. *difficile* tcdB sequence

```
1196  TAGTAAAACA AATCGAGAAT AGATATAAAA TATTGAATAA TAGTTTAAAT CCAGCTATTA G-CG-AGGATAA TGATTTTAAT ACTACAACGA ATACCTTTAT
      ..A....... ....C.A..C ........G. ..C.....G. ..C....GG. ...AT..... .T.A-...-... .......... .......T.. .C.AT...GG
      ..A....... ....C.A..C ........G. ..C.....G. ..C....GG. ...AT..... .T.A-...-... .......... .......T.. .C.AT...GG
      ..A....... ....C.A..C ........G. ..C.....G. ..C....GG. ...AT..... .T.A-...-... .......... .......T.. .C.AT...GG
      ..A....... ....C.A..C ........G. C.C.....G. ..C....GG. ...AT..... .T.A-...-... .......... .......T.. .C.AT...GG
      ..a....t.. ...ta.a... .......... .c.....cg. c.ac...... ...t.c.... a-t.a...-..c ...c...... .......t.. .a.tt....g
1196  TAGTAAAACA AATCGAGAAT AGATATAAAA TATTGAATAA TAGTTTAAAT CCACCTATTA G-CG-AGGATAA TGATTTTAAT ACTACAACGA ATACCTTTAT

1296  TG--ATAGTATAATG-GCTGA-AG CTAATGCAGAT-A-ATGGTA-GATTTATGAT-GGAACTA--GGAAA GT-ATTTAAGAGTTGG-TTT-CT-TCCCAGATGT TAAAACTACT
      ..--.A...T.GG-.A...-.T.. ......A...G-.-..A-..A.T.....-.--.C..AA.TC....- ..T.......G.....A...--.A...T-..A.C ...T.....-
      ..--.A...T.GG-.A...-.T.. ......A...G-.-..A-..A.T.....-.--.C..AA.TC....- ..T.......G.....A...--.A...T-..A.C ...T.....A
      ..--.A...T.GG-.A...-.T.. ......A...G-.-..A-..A.T.....-.--.C..AA.TC....- ..T.......G.....A...--.A...T-..A.C ...T.....A
      ..--.A...T.GG-.A...-.T.. ......A...G-.-..A-..A.T.....-.--.C..AA.TC....-...T.......G.....A...--.A...T-..A.C ...T.....A
      ..ac.a.t..gc..---..-.ttt ......a....a.t...a.--.-.........aaa..t..---c... t.-......a......a...g.--.-......... ..g..g....
1296  TG--ATAGTATAATG-GCTGA-AG CTAATGCAGAT-A-ATGGTA-GATTTATGAT-GGAACTA--GGAAA GT-ATTTAAGAGTTGG-TTT-CT-TCCCAGATGT TAAAACTACT

1396  A-TTAACTT-AAGTGGCCCTG-A AGCATATGC-G GCAGCTTATC AAGATTTATT AATGTTTAAA GA-A-G-GCAGTATGAATA-TCC-AT-TTGA-TAGAA GCTGATTTAA
      .G...-...T......T...AC. .T-......A. .-.......A .......... ..CA...... ..G.T.A...-..-..-..C.T.T..A...--..C-.T -....G....
      .-...-...T......T...AC. .T-......A. .-.......A .......... ..CA...... ..G.T.A...-..-..-..C.T.T..A...--..C-.T -....G....
      .-...-...T......T...AC. .T-......A. .-.......A .......... ..CA...... ..G.T.A...-..-..-..C.T.T..A...--..C-.T -....G....
      .-...-...T......T...AC. .T-......A. .-.......A .......... ..CA...... ..G.T.A...-..-..-..C.T.T..A...--..C-.T.-....G....
      .-.......-......a....-g ..t....a.a. .-........ .......g.. .......... ..t.---at....ca....-.t.-..-..-.c..... c....g....
1396  A-TTAACTT-AAGTGGCCCTG-A AGCATATGC-G GCAGCTTATC AAGATTTATT AATGTTTAAA GA-A-G-GCAGTATGAATA-TCC-AT-TTGA-TAGAA GCTGATTTAA

1496  GAAACTTTGA AATCTC-TAAA ACTAATATTT CTCAATCAAC TGAACAAGA-A ATGGCTAGCT TATGGTCA-TT TGACGATGCA AGAGCTAAAG- CTCAATTTGA
      ....T..... .T.-..C...G GT......A. .....G.... A........G. .AAA-...T. .....-..A.. .A.T..A.A. .........A- T.........
      ....T..... .T.-..C...G GT......A. .....G.... A........G. .AAA-...T. .....-..A.. .A.T..A.A. .........A- T.........
      ....T..... .T.-..C...G GT......A. .....G.... A........G. .AAA-...T. .....-..A.. .A.T..A.A. .........A- T.........
      ....T..C.. .T.-..C...G GT......A. .....G.... A........G ..AAA-..... .....-..A.. .A....A.A. .........A- T.........
      ....t....- .g.t..c.... .....a.... ......t... a.....g..-. ..aa....t. ........-.. .a..c.a... .....-c...t ..........
1496  GAAACTTTGA AATCTC-TAAA ACTAATATTT CTCAATCAAC TGAACAAGA-A ATGGCTAGCT TATGGTCA-TT TGACGATGCA AGAGCTAAAG- CTCAATTTGA
```

APPENDIX I-continued

*C. difficile* tcdB sequence

```
1596  AGAATAT--AA-A AGGAATTATT TTGAAGGTTC TCTTGGTGAA GATGATAATC TTGATTTTTC TCAAAATA-TA GTAGTTGACA AGGAGTATCT TT-TAGAAAAA
      ......C--..G. .A-....... ........G. A.....A... .......... .......... ........-C. ...AC..... .A..A..... ..-.......G
      ......C--..G. .A-....... ........G. A.....A... .......... .......... ........-C. ...AC..... .A..A..... ..-.......G
      ......C--..G. .A-....... ........G. A.....A... .......... .......... ........C.- ...AC..... .A..A..... ..-.......G
      ......C--..G. .A-A...... ........G. A.....A... .......... .......... ...G
      .......aa..-. ...--..... ........g. a.....a... .......... ........g. ........-c. ...c....t. .a..t...g. ..c..-.....
1596  AGAATAT--AA-A AGGAATTATT TTGAAGGTTC TCTTGGTGAA GATGATAATC TTGATTTTTC TCAAAATA-TA GTAGTTGACA AGGAGTATCT TT-TAGAAAAA

1696  ATATCTTCAT TAGC-AA-G-AAG TTC-AGAGAGA GGATATATAC ACTATATTGT TCAGTTACAA GGAGATAAAA TTAGTTATGA AGCAGCATGT AACTTATTTG
      ..C....... C.A.G..-.-... ...-...A... ......G.G. .T........ ...A...... .......... ....C..... .......... ..........
      ..C....... C.A.G..-.-... ...-...A... ......G.G. .T........ ...A...... .......... ....C..... .......... ..........
      ..C....... C.A.G..-.-... ...-...A... ......G.T. .T........ ...A...... .......... ....C..... .......... ..........
      ...--..-.. c.t.-..t.a..a cc.g.a.t.a. .a......t. .t........ ...ac..... .......... .c..c..... ....t..... .........t
1696  ATATCTTCAT TAGC-AA-G-AAG TTC-AGAGAGA GGATATATAC ACTATATTGT TCAGTTACAA GGAGATAAAA TTAGTTATGA AGCAGCATGT AACTTATTTG

1796  C-AAAGACTCC TTATGATAGT GTACTGTTTC AGAA-AAATAT AGAAGATTCA GAAATTGCAT ATTATTATAA TCCTGGAGAT GGTGAAATAC AAGAAATAGA
      .-...A.A... ......C... A....A.... .A..-...... .......... ...G.A.... ....C..... ....AC.... A......... .......T..
      .-...A.A... ......C... A....A.... .-..G...... .......... ...G.A.... ....C..... ....AC.... A......... .......T..
      .-...A.A... ......C... A....A.... .A..-...... .......... ...G.A.... ....C..... ....AC.... A......... .......T..
      .a.....A... ....tc.... a....a.a.. ....-...... .....g.... ....ca.... ....c...t. .gt..c.... .c...g...a. ..........
1796  C-AAAGACTCC TTATGATAGT GTACTGTTTC AGAA-AAATAT AGAAGATTCA GAAATTGCAT ATTATTATAA TCCTGGAGAT GGTGAAATAC AAGAAATAGA

1896  CAAGTATAAA ATTCCA-AGTA T--AATTTCTGA TAGACCTAAG ATTAAATTAA CATTTATTGG TCATGGTAAA GATGAATTTA ATACTGATAT ATTTG-CAGGT
      T.......G. .....TG.-.. G--...C..... .......... .......... ....C..... ......C... .C........ .......... .....-.....
      T.......G. .....TG.-.. G--...C..... .......... .......... ....C..... ......C... .C........ .......... .....-.....
      T.......G. .....TG.-.. G--...C..... .......... ........G. ..C....... ......C... .C...G.... .......... .....-.....
      t..a....g. .....--.-.. .ca.......a. ..a..g...t .......... .t........ .......... tc........ .........c .....c..-a.
1896  CAAGTATAAA ATTCCA-AGTA T--AATTTCTGA TAGACCTAAG ATTAAATTAA CATTTATTGG TCATGGTAAA GATGAATTTA ATACTGATAT ATTTG-CAGGT

1996  TTTGATGTAG ATTCATTATC CACAGAAATA GAAGCAGCAA TAGATTTAGC TAAAG-AGGAT ATTTCTCCTA AGTCA-ATAGA AATAAATTTA TTAGGATGTA
      C......... .......... TT........ ...A...... ...G...... C....-..... .......... .A..T-..... ......C... C.G.......
      C......... .......... TT........ ...A...... ...G...... C....-..... .......... .A..T-..... ......C... C.G.......
      C.......G. .......... TT........ ...A..AT.T .......... .....C..-.. .......... .A..T-..... ......C... C.G.......
      c......... .......... tt.t..g... ...a..at.t ..a....... .....c.-... .......... ...-.t..... .......... c.g.......
1996  TTTGATGTAG ATTCATTATC CACAGAAATA GAAGCAGCAA TAGATTTAGC TAAAG-AGGAT ATTTCTCCTA AGTCA-ATAGA AATAAATTTA TTAGGATGTA

2096  ATATGTTTAG CTACTCTATC AACGTAGAGG AGACTTATCC TGGAAAA-TTA TTACTTAAAG TTAAAGATAA AATATCAGAA TTAATGCCAT CTATAAGTCA
      .C........ ...T...G.A ..T.....A. .......... ...G...-... .......G.. .......... .G........ .......... ....G.....
      .C........ ...T...G.A ..T.....A. .......... ...G...-... .......G.. .......... .G........ .......... ....G.....
      .C........ ...T...G.A ..T.....A. .......... ...G...-... .......G.. .......... .G........ .......... ..........
      .c.....c.. .......... .g..c...a. .......... .......c..- .........a .........g .g........ .......... ..........
2096  ATATGTTTAG CTACTCTATC AACGTAGAGG AGACTTATCC TGGAAAA-TTA TTACTTAAAG TTAAAGATAA AATATCAGAA TTAATGCCAT CTATAAGTCA

2196  AGACTCTATT ATAGTAAGTG CAAATCAATA TGAAGTTAGA ATAAATAG-TG AAGGAAGAAG AGAATTATTG GATCATTCTG GTGAATGGAT AAATAAAGAA
      .......... .......... .......... .......... ........-.. .......... .........A ..C....... .......... ...C......
      .......... .......... .......... .......... ........-.. .......... .........A ..C....... .......... ...C......
      .......... .......... .......... .......... ..T.....-.. .......... .........A ..C....... .......... ...C......
      .......... .c........ .......... .......... ......-.aa. ......a... ....a....a .......... ..a....... ..........
2196  AGACTCTATT ATAGTAAGTG CAAATCAATA TGAAGTTAGA ATAAATAG-TG AAGGAAGAAG AGAATTATTG GATCATTCTG GTGAATGGAT AAATAAAGAA

2296  GAAAGTATTA TAAAGGATAT TTCATCAAAA GAATATATAT CATTTAATCC TAAAGAAAAT AAAATTACAG TAAAATCTAA AAATTTACCT GAGCTATCTA
      .......... .......... .......... .......... .......... ......G... ...G...T.. .......... .......... ..AT......
      .......... .......... .......... .......... .......... ......G... .......T.. .......... .......... ..AT......
      .......... .......... .......... .......... .......... .......... .......T.. .......... .........C ..AT......
      .......... .......... .......... .......... .......... a......... .......t.. .g........ .t......a. .....g....
2296  GAAAGTATTA TAAAGGATAT TTCATCAAAA GAATATATAT CATTTAATCC TAAAGAAAAT AAAATTACAG TAAAATCTAA AAATTTACCT GAGCTATCTA
```

APPENDIX I-continued

C. *difficile* tcdB sequence

```
2396  CATTATTACA AGAAATTAGA AATAATTCTA ATTCAAGTGA TATTGAACTA GAAGAAAAAG TAATGTTAAC AGAATGTGAG ATAAATGTTA TTTCAAATAT
      .......... .......... .......... .......... .......... .......... ........G. .......... .......... ..........
      .......... .......... .......... .......... .......... .......... ........G. .......... .......... ..........
      .......... .......... ..C....... .......... .......... .......... ........G. .......... .......... ..........
      .......... .........g ......g.c. .......... ......t... ...a...... .......... .......... .........g c.........
2396  CATTATTACA AGAAATTAGA AATAATTCTA ATTCAAGTGA TATTGAACTA GAAGAAAAAG TAATGTTAAC AGAATGTGAG ATAAATGTTA TTTCAAATAT

2496  AGATACG-CAA ATTGTTG-AGG AAAGGATTGA AGAAGCTAAG AAT-TTAACTT CTGACTCTAT TAATTATATA AAAGA-TGAAT TTAAACTAAT AGAATCTATT
      ...G..A-... G.G..A.-.A. ....A..... .........- ..GC...... .......... .......... ..-..A.... .......... ..........
      ...G..A-... G.G..A.-.A. ....A..... .........- ..GC...... .......... .......... ..-..A.... .......... ..........
      ...G..A-... G.G..A.-.A. .......... .........- ..GC...... .......... .......... ..-..A.... .......... ..........
      .....-.a..g .....g.a... -...a..... .........a ...-..g... .......... .......... ...a.-.... .......... ..........
2496  AGATACG-CAA ATTGTTG-AGG AAAGGATTGA AGAAGCTAAG AAT-TTAACTT CTGACTCTAT TAATTATATA AAAGA-TGAAT TTAAACTAAT AGAATCTATT

2596  TCTGATGCAC TATGTGACTT AAAACAACAG AATGAATTAG AAGATTCTCA TTTTATATCT TTTGAGGACA TAT-CAGA-GAC TGATGAGGGA TTTAGTATAA
      .......... .......... .......... .......... .......... .......... .......... ...-....-... .........G ..........
      .....G.... .......... .......... .......... .......... .......... .......... ...-....-... .........G ..........
      .......... ...AC..T.. .......... .......... ....G..... .......... ........T. ...-....A... ......A..C ..........
      ......t..t ...a...t.. ......t..a ....g..... .t........ .......... ........t. ...c..-.-... ...aa.t... .....g....
2596  TCTGATGCAC TATGTGACTT AAAACAACAG AATGAATTAG AAGATTCTCA TTTTATATCT TTTGAGGACA TAT-CAGA-GAC TGATGAGGGA TTTAGTATAA

2696  GATTTATTAA TAAAGAAACT GGAGAA-TCTA TATTTGTAGA AACTGAAAAA- ACAATATTCT CTGAATATGC TAATCATATA ACTGAAGAGA TTTCTAAGAT
      .......... .......... ......-.... .......... ..........- .......... .......... .......... .......... ..........
      .......... .......... ......-.... .......... ..........- .......... .......... .......... .......... ..........
      .......G.. .......... ......-.... .......... .........G- G......... .......... .......... ........A. ........T.
      .g..c..... .......... ...-..c.... ....a..... ..........g .-...t.... .......... ..c....... t..a...a.. .......t..
2696  GATTTATTAA TAAAGAAACT GGAGAA-TCTA TATTTGTAGA AACTGAAAAA- ACAATATTCT CTGAATATGC TAATCATATA ACTGAAGAGA TTTCTAAGAT
```

APPENDIX I-continued

*C. difficile* tcdB sequence

```
                                                                                                               KERLA-tcdB-F1
2796  AAAAGGTACT ATATTTGATA CTGTAAATGG TAAGTTAGTA AAAAAAGTAA ATTTAGATAC TACACACGAA GTAAATACTT TAAATGCTGC ATTTTTTATA
      .......... .......... .......... .......... .......... .......... .......... .......... .......... ..........
      .......... .......... .......... .......... .......... .......... .......... .......... .......... ..........
      .....A.... .......... .......... ......G..G .......... C.......G. ......T... ..G....... .......... ..........
      .....a.... .......... a......... c..a...... .......... ..c.....g. .g....t... .........c .....t.... c.........
2796  AAAAGGTACT ATATTTGATA CTGTAAATGG TAAGTTAGTA AAAAAAGTAA ATTTAGATAC TACACACGAA GTAAATACTT TAAATGCTGC ATTTTTTATA

2896  CAATCATTAA TAGAATATAA TAGTTCTAAA GAATCTCTTA GTAATTTAAG TGTAGCAATG AAAGTCCAAG TTTACGCTCA ATTATTTAGT ACTGGTTTAA
      .......... .......... .......... .......... .......... .......... .....T.... .......... .......... ..........
      .......... .......... .......... .......... .......... .......... .....T.... .......... .......... ..........
      .......... .T.G...... .......... .......... .......... .......... .....T.... ....T..... .......... ..........
      .......... .C........ ..C.A..... .....A.... .......... .......... ..g..t.... ....t..... .......... ..........
2896  CAATCATTAA TAGAATATAA TAGTTCTAAA GAATCTCTTA GTAATTTAAG TGTAGCAATG AAAGTCCAAG TTTACGCTCA ATTATTTAGT ACTGGTTTAA

                                       NK-toxB-B34A0
2996  ATACTATTAC AGATGCAGCC AAAGTTGTTG AATTAGTATC AACTGCATTA GATGAAACTA TAGACTTACT TCCTACATTA TCTGAAGGAT TACCTATAAT
      .......... .......... .G........ .......... .......... .......... .......... .......... .......... ..........
      .......... .......... .G........ .......... .......... .......... .......... .......... .......... ..........
      ....C..... ......G..T .......... .......... .......C.. .......... ....T..... .......... .......... .....G....
      .......... ......tt.t .......... .g........ .......... .......... .......... .......... .......... .....G....
2996  ATACTATTAC AGATGCAGCC AAAGTTGTTG AATTAGTATC AACTGCATTA GATGAAACTA TAGACTTACT TCCTACATTA TCTGAAGGAT TACCTATAAT

                 KENP-tcdB-R1
3096  TGCAACTATT ATAGATGGTG TAAGTTTAGG TGCAGCAATC AAAGAGCTAA GTGAAACGAG TGACCCATTA TTAAGACAAG AAATAGAAGC TAAGATAGGT
      .......... .......... .......... .......... .......... .......... .......... .......... .......... ..........
      .......... .......... .......... .......... .......... .......... .......... .......... .......... ..........
      ...T...... .......... .......... ....T....T ......T.G. .......A.. .......... .......... .......... A..A......
      ...t..a..a .......... ....c..... c..g.....t .....a..c. .c.....a.a .......... .......... .......... c.........
3096  TGCAACTATT ATAGATGGTG TAAGTTTAGG TGCAGCAATC AAAGAGCTAA GTGAAACCAG TGACCCATTA TTAAGACAAG AAATAGAAGC TAAGATAGGT
```

APPENDIX I-continued

*C. difficile* tcdB sequence

```
3196  ATAATGGCAG TAAATTTAAC AACAGCTACA ACTGCAATCA TTACTTCATC TTTGGGGATA GCTAGTGGAT TTAGTATACT TTTAGTTCCT TTAGCAGGAA
      .......... .......... .......... .......... .......... .......... .......... .......... .......... ..........
      .......... .......... .......... .......... .......... .......... .......... .......... .......... ..........
      .......... .......... .G........ ........T. .......... ...A..A... ..A....... .......... .......... C......G..
      ........t. .......... .g....t... .........g .......g.. ...a..a... ........t. ....c..... .......... ..g.......
3196  ATAATGGCAG TAAATTTAAC AACAGCTACA ACTGCAATCA TTACTTCATC TTTGGGGATA GCTAGTGGAT TTAGTATACT TTTAGTTCCT TTAGCAGGAA

3296  TTTCAGCAGG TATACCAAGC TTAGTAAACA ATGAACTTGT ACTT-CGAGAT AAGGCAACAA AGGTTGTAGA TTATTTTAAA CATGTTTCAT TAGTTGAAAC
      .......... .......... .......... .......... ....-...... .......... .......... .......... .......... ..........
      .......... .......... .......... .......... ....-...... .......... .......... .......... .......... ..........
      .......... A..C.....T ........T. ........A. .-..A...C. G......A.. .T..C..... .......GGC ...A...... ...C....T.
      .......... g.......t. .......... ........a. ...c-.a... .......... .a...a.... .......... ...a...... ...c...g..
3296  TTTCAGCAGG TATACCAAGC TTAGTAAACA ATGAACTTGT ACTT-CGAGAT AAGGCAACAA AGGTTGTAGA TTATTTTAAA CATGTTTCAT TAGTTGAAAC

3396  TGAAGGAGTA TTTACTTTAT TAGATGATAA AATAATGATG CCACAAGATG ATTTAGTGA-T ATCAGAAATA GATTTTAATA ATAATTCAAT AGTTTTAGGT
      .......... .......... .......... .G........ .......... ........-. .......... .......... .......... ..........
      .......... .......... .......... .G........ .A........ ........-. .......... .......... .......... ..........
      .......C.. .......G.. .......... .......... .......... .......A-. ...T...... ..C....... ..C....... .AC.......
      ...g...c.. ....a..... .......... ......t... ..t....... .c..g..-.t .......... ..c....... .......... .AC.......
3396  TGAAGGAGTA TTTACTTTAT TAGATGATAA AATAATGATG CCACAAGATG ATTTAGTGA-T ATCAGAAATA GATTTTAATA ATAATTCAAT AGTTTTAGGT

3496  AAATGTGAAA TCTGGAGA-AT GGAAGGTGGT TCAGGTCATA- CTGTAACTGA TGATATAGAT CACTTCTTTT CAGCACCATC AATAACATAT AGAGAGCCAC
      .......... ........-.. .......... ..........- .......... .......... .......... .......... .......... ..........
      .......... ........-.. .......... ..........- .......... .......... .......... .......... .......... ..........
      .......... .A......-.. .......... ..........- ......C... .......... .......C.. .......... ..C....... ..G..A...T
      .......... ........gc. -......... .....c...c ..-....... .......... ..t....... ..t....... .......... ...a.a...t
3496  AAATGTGAAA TCTGGAGA-AT GGAAGGTGGT TCAGGTCATA- CTGTAACTGA TGATATAGAT CACTTCTTTT CAGCACCATC AATAACATAT AGAGAGCCAC

3596  ACTTATCTAT ATATGACGTA TTGGAA GTAC AAAAAG-AAGA ACTTGATTTG TCAAAAGATT TAATGGTATT ACCTAATGCT CCAAATAGAG TATTTG-CTTG
      .......... .......... ...... .... ......-.... .......... .......... .......... .......... .......... ......-....
      .......... .......... ...... .... ......-.... .......... .......... .......... .......... .......... ......-....
      .T........ ......T... ..A..T ...- ...G..G.... .........A .......... .......... .G.......C ..G.....A. .C....G..-.
      gg........ ......t... ..-a..ta..a ......-...a ..a......t .......... .......... .........a ..t....g.. ......-g..a
3596  ACTTATCTAT ATATGACGTA TTGGAA-GTAC AAAAAG-AAGA ACTTGATTTG TCAAAAGATT TAATGGTATT ACCTAATGCT CCAAATAGAG TATTTG-CTTG

3696  GGAAACAGGA TGGACACCAG GTTTAAGAAG CTTAGAAAAT GATGGCACAA AACTGTTAGA CCGTATAAGA GATAACTATG AAGGTG-AGTT TTATTGGAGA
      .......... .......... .......... .......... .......... .......... .......... .......... ......-.... ..........
      .......... .......... .......... .......... .......... .......... .......... .......... ......-.... ..........
      ....G..... .....G.... .......... .......... ....T..... ...A...... .......... ...C.T.... ....-.C.... ..........
      t....tg... .......... .g..c..... t....c.... ..c....t.. ..t.a..... t......... ...c.t.... .....c-.a.. ..........
3696  GGAAACAGGA TGGACACCAG GTTTAAGAAG CTTAGAAAAT GATGGCACAA AACTGTTAGA CCGTATAAGA GATAACTATG AAGGTG-AGTT TTATTGGAGA

3796  TATTTT-GCTT TTATAGCTGA TGCTTTAATA ACAACATTAA AACCAAGATA TGAAGATACT AATATAAGAA TAAATTTAGA TAGTAATACT AGAAGTTTTA
      ......-.... .......... .......... .......... .......... .......... .......... .......... .......... ..........
      ......-.... .......... .......... .......... .......... .......... .......... .......... .......... ..........
      .-....C.... .......... .T..G..... ...A...... .......... .......... .......... ...G...... C......... ..........
      .....c-.... .......... .......... ...a...... .....c.... .......... ...g...... .....c.... .g.c...... ..........
3796  TATTTT-GCTT TTATAGCTGA TGCTTTAATA ACAACATTAA AACCAAGATA TGAAGATACT AATATAAGAA TAAATTTAGA TAGTAATACT AGAAGTTTTA

3896  TAGTTCCAAT AATAACTACA GAATATATAA GAGAAAAA-TT ATCATATTCT TTCTATGGTT CAGGAGGAAC TTATGCATTG TCTCTTTCTC AATATAATAT
      .......... .......... .......... ........-.. .......... .......... .......... .......... .......... ..........
      .......... .......... .......... ........-.. .......... .......... .......... .......... C......... ..........
      .......G.. .......... .......... ........-.. .......... ..T....C.. .......... ........A. .......... ....C.....
      .......g.. t.....c... ...c.a.... ..-.....t.. ...t...... ..t....... ....g...t. ....t...a. .......... c.........
3896  TAGTTCCAAT AATAACTACA GAATATATAA GAGAAAAA-TT ATCATATTCT TTCTATGGTT CAGGAGGAAC TTATGCATTG TCTCTTTCTC AATATAATAT
```

APPENDIX I-continued

*C. difficile* tcdB sequence

```
3996  GGGTATAAAT ATAGAAT-TAA G-TGAAAGTGA TGTTTGGATT ATAGATGTTG  ATAATGTTGT GAGAGATGTA ACTATAGAAT CTGATAAAAT TA-AAAAAGGT
      .......... .......-... .-......... .......... ..........  .......... .......... .......... .......... ..-........
      .......... .......-... .-......... .......... ..........  .......... .......... .......... .......... ..-........
      .AA......C .......-... A-.....A... .AC....G.. ........C.  .C.....C.. A.......C. .......... .......... ..-.......A
      .aa....g.. t..-...c.-. .t.....a... .ac....g.. ..........  .......... a.a.a.ca.c ........g. .a...g...- ..c........
3996  GGGTATAAAT ATAGAAT-TAA G-TGAAAGTGA TGTTTGGATT ATAGATGTTG  ATAATGTTGT GAGAGATGTA ACTATAGAAT CTGATAAAAT TA-AAAAAGGT

4096  GATTTAATAG AAGGTATTTT ATCTACA-CTA AGTATTGAAG AGAATAAAAT  TATCTTAAAT AGCCATGA-GA TTAATTTTTC TGGTGAGGT-A AATGGAAGTA
      .......... .......... .......-... .......... ..........  .......... ........-.. .......... .........-. ..........
      .......... .......... .......-... .......... ..........  .......... ........-.. .......... .........-. ..........
      .......... ..AA...... .....A.-T.. .......... .C........  ...T...G.. .AT.....-A. .......C.. ...A-.CA.T. ......G...
      ..a....... ..aa...... .....-.g... .a........ .t........  ...t...... .at...-.ct. .......c.a ...a..ta.-. ....a...c.
4096  GATTTAATAG AAGGTATTTT ATCTACA-CTA AGTATTGAAG AGAATAAAAT  TATCTTAAAT AGCCATGA-GA TTAATTTTTC TGGTGAGGT-A AATGGAAGTA

4196  ATGGATTTGT TTCTTTAACA TTTTCAATTT TAGAAGGA-AT AAATGCAATT  ATAGAAGTTG ATTTATTATC TAAATCATAT AAA-TTACTTA TTTCTCCCCA
      .......... .......... .......... ........-.. ..........  .......... .......... .......... ...-....... ..........
      .......... .......... .......... ........-.. ..........  .......... .......... .......... ...-....... ..........
      .......... A......... ..C.....C. ........-.. .......G..  .......... .......... .......... ...G..-.... .......T..
      .ca.....a. a......... .......... ...-....t.. ....at....  ......a... .....g.... a.....t... ...-a.....c .......-t.
4196  ATGGATTTGT TTCTTTAACA TTTTCAATTT TAGAAGGA-AT AAATGCAATT  ATAGAAGTTG ATTTATTATC TAAATCATAT AAA-TTACTTA TTTCTGGCGA

4296  A-T-TAAAAATA TTGAT-GTTAA ATTCAAAT-CA TATTCAACAG AAA-ATAGATT ATATAGGATT CAATAGCGAA TTA-CAGAAAA ATATACCATA TAGCTT-TGTA
      .-.-........ .....-..... ........-.. .......... ...-....... .......... .......... ...-....... .......... ......-....
      .-.-........ .....-..... ........-.. .......... ...-....... .......... .......... ...-....... .......... ......-....
      .-C-......C. .....-.GC.. ........T.- .G........ ...-....... .......... G......... ...-..A.... .......T.. ...T..-.A.G
      .t.g..tg..-. .....a.-a.. .c...tg.-g- .........- ...g.....c .......... t...g.t... -c.t......t .......t.. ...-..a.a..
4296  A-T-TAAAAATA TTGAT-GTTAA ATTCAAAT-CA TATTCAACAG AAA-ATAGATT ATATAGGATT CAATAGCGAA TTA-CAGAAAA ATATACCATA TAGCTT-TGTA

4396  GAT-AGTGAAG GAAAAGAGAA TGGTTTTATT-AATGGTTC-AA CAAAAGAAGG TTTATTTGTA TCTGAATTAC CTGATGTAGT TC-TTATAAGT AAGGTTTATA
      ...-....... .......... ..........-........-.. .......... .......... .......... .......... ..-........ ..........
      ...-....... .......... ..........-........-.. .......... .......... ..A....... .......... ..-........ ..........
      ...G.-..... .......A.. ...A......-...T...T-T. .......... .......... .........T .......... ..-.C....T. ..A.......
      ...-.a....a ct...t.t.. c.........g.c.-ac..t.. -......... .c.g...ac. g.......tt ..a...-.a. c.a.......g ..ta......
4396  GAT-AGTGAAG GAAAAGAGAA TGGTTTTATT-AATGGTTC-AA CAAAAGAAGG TTTATTTGTA TCTGAATTAC CTGATGTAGT TC-TTATAAGT AAGGTTTATA

4496  TGGATGATAG TAAGCCTTCA TTTGGATATT ATAGTAATA-A TTTGAAAGAT GTCA-AAGTTA TAACTAAACA TAATGTT-AAT ATATTAACAG GTTATTATC-T
      .......... .......... .......... .........-. .......... ....-...... .......... .......-... .......... .........-.
      .......... .......... .......... .........-. .......... ....-...... .......... .......-... .......... .........-.
      ....CA.... ...A...C.. .......... ........G-. .......... ..T.-...... .......... .G.C...-.T. ...A...... ....A....-.
      ..cc...... ...taa..t. ...at..... c.......-.g ...a...... a.t.g..-... ...a.....g .g.....a... -..c...t.. .aa.....-.t
4496  TGGATGATAG TAAGCCTTCA TTTGGATATT ATAGTAATA-A TTTGAAAGAT GTCA-AAGTTA TAACTAAACA TAATGTT-AAT ATATTAACAG GTTATTATC-T

4596  TAAG-GATGAT ATAAAAATCT CTCTTTCTTT GACTCTACAA GATGA-AAAA-A CTATAAAGTT AAATAGTGTG CATTTAGATG AAAGTGGAGT AGCTGAGATT
      ....-...... .......... .......... .......... .....-....-. .......... .......... .......... .......... ..........
      ....-...... .......... .......... .......... .....-....-. .......... .......... .......... .......... ..........
      ...AA...... .......... .......... T...A..... ...-.-....T. .......A.. ....G.A..A T......... ...A...... ......A..A
      ...a-...... ..g..gg.a. .a........ c...a..g.. ...-.c...t-. .......... g...g....a t..c...... ...a...... ...ac.a..a
4596  TAAG-GATGAT ATAAAAATCT CTCTTTCTTT GACTCTACAA GATGA-AAAA-A CTATAAAGTT AAATAGTGTG CATTTAGATG AAAGTGGAGT AGCTGAGATT

4696  TTGAAGTTCA TGAAT-A-G-AAA AGGTAATACA AATACTTCAG ATTCTTTAAT GAGCTTT-TTA GAAAGTATGA ATATAAAAAG TATTTTCGT-T AAT-TTCTTAC
      .......... .....-.-.-... .....G.... .......... .......... .......-... .......... .......... .........-. ...-.......
      .......... .....-.-.-... .....G.... .......... .......... .......-... .......... .......... .........-. ...-.......
      .....A..T. .....-.-A-... .....G.... .......... .......... .......-... .......... .C........ .......A.-A ..A-.C....A
      .....a..t. .....a.t.c... .a..gc.tt. .........a .c..g..... ..-a...c... .........c. .........a .......-.ac ...aa..-..g
4696  TTGAAGTTCA TGAAT-A-G-AAA AGGTAATACA AATACTTCAG ATTCTTTAAT GAGCTTT-TTA GAAAGTATGA ATATAAAAAG TATTTTCGT-T AAT-TTCTTAC
```

APPENDIX I-continued

*C. difficile* tcdB sequence

```
4796  AATCTAATAT TAAGTTTATA TTAGATGCTA ATTTTATAAT AAGTGGTA-CT ACTTCTATTG GCCAATTTGA GTTTATTTGT GATGAAA-ATG ATAATATACA
      .......... .......... .......... .......... ........-.. .......... .......... .......... .......-..A ..........
      .......... .......... .......... .......... ........-.. .......... .......... .......... .......-..A ..........
      ........GC ....C..... ......A... .......... ........-.. ....T..... .T........ .......... ...-...G..A ..........
      .cc....... cg........ c.....a... ....c..... .......g.-. .a........ .g........ ac....c... ...-...g..a .a........
4796  AATCTAATAT TAAGTTTATA TTAGATGCTA ATTTTATAAT AAGTGGTA-CT ACTTCTATTG GCCAATTTGA GTTTATTTGT GATGAAA-ATG ATAATATACA

4896  ACCATATTTC ATTAAGTTTA ATACACTAGA AACTAATTAT ACTTTATATG TAGGAAATAG ACAAAATATG ATAGTGGAAC CAAATTATGA TTTAGATGAT
      .......... .......... .......... .......... .......... .......... .......... .......... .......... ..........
      .......... .......... .......... .......... .......... .......... .......... .......... .......... ..........
      .......... .......... .......... ......A... ...C...... ....T..... .......... .....A.... ........A. ..........
      .........t .....c.... .a.t.aa... .....gc... ...c...... .......... .......t.. .......... ...g....c. c.........
4896  ACCATATTTC ATTAAGTTTA ATACACTAGA AACTAATTAT ACTTTATATG TAGGAAATAG ACAAAATATG ATAGTGGAAC CAAATTATGA TTTAGATGAT

4996  TCTGGAGATA TATCTTCAAC TGTTATCAAT TTCTCTCA-AA AGTATCTTTA TGGAATAGAC AGTTGTGTTA ATAAAGTTGT AATTTCACCA AATATT-TATA
      .......... .......... .......... ........-.. .......... .......... .......... .......... .......... ......-....
      .......... .......... .......... ........-.. .......... .......... .......... .......... .......... ......-....
      ........C. .......... ...C..T... ..T.....G.. .-..C..... .......... .......... .......... .........C GGG...-....
      ......a... .......... ...c..t... ........g.. .-........ .......... c...a..... ........a. ....g..... ...-..a....
4996  TCTGGAGATA TATCTTCAAC TGTTATCAAT TTCTCTCA-AA AGTATCTTTA TGGAATAGAC AGTTGTGTTA ATAAAGTTGT AATTTCACCA AATATT-TATA

5096  CAGATGAAAT AAATATAACG CCTGTATATG AAA-CAAATAA TACTTATCCA GAAGTTATTG TATTAGATGC AAATTATATA AATGAAAAAA TAAATGTTAA
      .......... .......... .......... ...-....... .......... .......... .......... .......... ..C....... ..........
      .......... .......... .......... ...-....... .......... .......... .......... .......... ..C....... ..........
      .......... .......... ......C... ..G-....... .......... .....G.... ........A. .......... .G........ .C...A....
      .......... .........a .........- ...c.....t. ..t..g.... ........a. .......... .......... ..c....... ..........
5096  CAGATGAAAT AAATATAACG CCTGTATATG AAA-CAAATAA TACTTATCCA GAAGTTATTG TATTAGATGC AAATTATATA AATGAAAAAA TAAATGTTAA

5196  TATCAATGAT C-TATCTATAC GATATGTAT-G GAGTAA-TGAT GGTAATGATT TTATTCTTAT-GTCAACT-AGT GAAGAAAATA AGGTGTCACA AGTTAAAATA
      .......... .-......... .........-. ......-.... .......... ..........-.......-... .......... .......... ..........
      .......... .-......... .........-. ......-.... .......... ..........-.......-... .......... .......... ..........
      .......... T-......... .........-. ...-..G.... .......... ..........-.......G.-. .....G..C. ....A..... ..........
      .........- .t......... .........g. ..-...-.... ....g....c ..........a.-...a.-... ..g..g.... .tcaac.... ..........
5196  TATCAATGAT C-TATCTATAC GATATGTAT-G GAGTAA-TGAT GGTAATGATT TTATTCTTAT-GTCAACT-AGT GAAGAAAATA AGGTGTCACA AGTTAAAATA

5296  AGATTCGTTA ATGT-TTTTAA AGATAAGACT TTGGCAAATA AGCTATCTTT TAACTTTAGT GATAAACAAG ATGTACCTGT AAGTGAAATA ATCTT-ATCAT
      .......... ....-...... .......... .......... .......... .......... .......... .......... .......... .....-.....
      .......... ....-...... .......... .......... .......... .......... .......... .......... .......... .....-...G.
      .....TAC.. ....-...... ..G...T... A.AT..G... ..A....... ...T...... ..C..G.... ..A..T..A. ..A.A...T. ..-..C.A...
      .....t.... ....c...a.. ..-cg.t... gca...g... ..t.g..... ......c... .....g.... .....t.... ....a...t. ..-..c.a...
5296  AGATTCGTTA ATGT-TTTTAA AGATAAGACT TTGGCAAATA AGCTATCTTT TAACTTTAGT GATAAACAAG ATGTACCTGT AAGTGAAATA ATCTT-ATCAT

5396  TTACACCTT-C ATATTATGAG-GATGGATTGA-TTGGCTATG-A TTTGGGTCT-A GTTTCTTTAT ATAATGAGAA ATTTTATATT AATAACTTTG G-AATGATGGT
      .........-. ..........-..........-.........-. .........-. .......... .......... .......... .......... .-.........
      .........-. ..........-..........-.........-. .........-. .......... .......... .......... .......... .-.........
      .........-. ........T.-..A.....-.C..AAT....-. ...A.....G. -......... .C........ .......... .....-.... .G.........
      ..t.-....g. .gc.....-..c.......tt-...a.....a. ...-.....-g -........g .......tt. c......... ....gt.... .a...-.....
5396  TTACACCTT-C ATATTATGAG-GATGGATTGA-TTGGCTATG-A TTTGGGTCT-A GTTTCTTTAT ATAATGAGAA ATTTTATATT AATAACTTTG G-AATGATGGT

5496  ATCTGGATTA ATATATATTA ATGATTCATT ATATTATTTT AAACCACCAG TAAATAATTT GATAACTGGA TTTGTGACTG TAGGCGATGA TAAATACTAC
      .......... .......... .......... .......... .......... .......... .......... .......... .......... ..........
      .......... .......... .......... .......... .......... .......... .......... .......... .......... ..........
      G.....G... G......... .......... .........C .........A ....G..C.. .......... ..ACA...A. .......... ..........
      .......... .......... .......... .........c .........a a.....c... .......... ..caca...a ...at.g.a. ......t...
5496  ATCTGGATTA ATATATATTA ATGATTCATT ATATTATTTT AAACCACCAG TAAATAATTT GATAACTGGA TTTGTGACTG TAGGCGATGA TAAATACTAC
```

APPENDIX I-continued

*C. difficile* tcdB sequence

```
5596  TTTAATCCA-A TTAATG-GTGG AGCTGCTTCA ATTGGAGAGA CAATAATTGA TGACAAAAAT TATTA-TTTCA ACCAAA-GTGG-AGTGTTACAA ACAGGTG-TAT
      .........-. ......-.... .......... .......... .......... .......... .....-..... ......-....-.......... .......-...
      .........-. ......-.... .......... .......... .......... .......... .....-..... ......-....-.......... .......-...
      .........G. .-....-.A.. .C........ G......A.. .......... ..G.....C. ..C..-..... G.....-A..-.......... .......-...
      ...g.c...-. cg..-.a.... ......a... ..a.....a. t..c...... ..gt...g.. .....c...-. .-....caa..t.-.t..g... gt...a.t..-
5596  TTTAATCCA-A TTAATG-GTGG AGCTGCTTCA ATTGGAGAGA CAATAATTGA TGACAAAAAT TATTA-TTTCA ACCAAA-GTGG-AGTGTTACAA ACAGGTG-TAT

5696  TTAGTACAGA AGATGGATTT AAA-TATTTTG CCCCAGCTA-A TACACTTGAT GAAAACCTAG AAGGAGAAGC AATTGATTTT ACTGGAAAAT TAATTATTGA-
      .......... .......... ...-....... .........-. .......... .......... .......... .......... .......... ..........-
      .......... .......... ...-....... .........-. .......... .......... .......... .......... .......... ..........-
      .......... .......... ...-....... .T.....-.G. .......... .....T.... ....T..... .......... .....C...C ..........-
      .t.t....tc t......-.. ...g....... .t..t...g-g .......... ......t... .g.....t.. .g.aa..... .t........ ...a......t
5696  TTAGTACAGA AGATGGATTT AAA-TATTTTG GCCCAGCTA-A TACACTTGAT GAAAACCTAG AAGGAGAAGC AATTGATTTT ACTGGAAAAT TAATTATTGA-

5796  CGAAAATATT TATTATTTTG-ATGATAATTA TAGAGGAGCT GTAGAATGG-A AAGAATTAGA TGGTGAAATG CACTATTTTA GCCCAGAAAC AGGTA-AAGCT
      .......... ..........-.A........ .......... .........-. .......... .......... .......... .......... .....-.....
      .......... ..........-.A........ .......... .........-. .......... .......... .......... .......... .....-.....
      T.....G.A. ..........G.-........ .....C.... A.......C. ..C.-..... ..A....... T......... ..A...T... .....-G....
      g.....-... ..........-.a........ .....cc... .....g...-. ..tt...... ..a.....ca t.......c. at...a..T. ...-.g....c
5796  CGAAAATATT TATTATTTTG-ATGATAATTA TAGAGGAGCT GTAGAATGG-A AAGAATTAGA TGGTGAAATG CACTATTTTA GCCCAGAAAC AGGTA-AAGCT

5896  TTTAAAGGTC TAAATCAAAT AGGTGATTAT AAATACTATT TCAATTCTGA TGG-AGTTATG CAAAAAGGAT TT-GTTAGTAT AAATGATAAT AAACACTATT
      .......... .......... .......G.. .......... .......... ...-....... .......... ..-........ .......... ..........
      .......... .......... .......G.. .......... .......... ...-....... .......... ..-........ .......... ..........
      ........G. .......... .......G.. ....T..... ....C..... ...T.-..... .......... ..-....A... .........G .C.TTT....
      c........t ..c....... t......a.. .....t.... .tg..ga.a. ...-.a..... ....ct..-. ..ca...c... .........g gt.ttt....
5896  TTTAAAGGTC TAAATCAAAT AGGTGATTAT AAATACTATT TCAATTCTGA TGG-AGTTATG CAAAAAGGAT TT-GTTAGTAT AAATGATAAT AAACACTATT

5996  TTGATGATTC TGGTGTTATG AAAGT-AGGTT ACACTGAAAT AGATGGCAAG C-ATTTCTACT TT-GCTGAAAA CGGAGAAATG-CAAATAGGAG TATTTAATAC
      .......... .......... .....-..... .......... .......... .-......... ..-........ ..........-.......... ..........
      .......... .......... .....-..... .......... .......... .-......... ..-........ ..........-.......... ..........
      .......... ......G... ..-..C...A. .T........ ......-... AT....T... ...-.....G.. T.........-.......... ..........
      ..a..a..ga ......g... c....-t..a. .t.t...gg. .a....t..a t-....t..t ...g..-a.... t.........-.a...t.... ..........
5996  TTGATGATTC TGGTGTTATG AAAGT-AGGTT ACACTGAAAT AGATGGCAAG C-ATTTCTACT TT-GCTGAAAA CGGAGAAATG-CAAATAGGAG TATTTAATAC

6096  AGAAGATGGA TTTAAATATT TTGCTCATCA TA-ATGAAGAT TTAGGAAATG AAGAAGGTGA AGAAATCTCA TATTCTGGTA TA-TTAAATTT CAATAATAAA
      .......... .......... .......... ..-........ .......... .......... .......... .......... ..-........ ..........
      .......... .......... .......... ..-........ .......... .......... .......... .......... ..-........ ..........
      ..C....... .......... .......... .G-........ .......... .......... ..C.C.T... .......... ..C...T... -..C.....G
      tcc....... .......t.. ...g..c.-. a.g....t... .......c.. .......g.. .ct..c..t. ...aa..... ..-..g..... t...ggg...
6096  AGAAGATGGA TTTAAATATT TTGCTCATCA TA-ATGAAGAT TTAGGAAATG AAGAAGGTGA AGAAATCTCA TATTCTGGTA TA-TTAAATTT CAATAATAAA

6196  ATTTACTATT TTGATGAT-TC ATTTACAGCT GTAGTTGGAT-GGAAAGAT-TT AGAGGATGGT TC-AAAGTATT ATTTTGATGA-AGATACAGCA GAAGCATATA
      .......... ........-.. .......... ..........-........-.. .......... ..-........ ..........-.......... ..........
      .......... ........-.. .......... ..........-........-.. .......... ..-........ ..........-.......... ..........
      .....T.... ........-.. .........A ..........-....G...-.. ...A...... ..-...A.... .C........-.A......... .......C..
      ..c..t.t.. .....-..c.. .aa....... .....c....g..gt.-c.c.. -..t.....c ..t.c.-.... ....c.....t.-...g.... .......gc.
6196  ATTTACTATT TTGATGAT-TC ATTTACAGCT GTAGTTGGAT-GGAAAGAT-TT AGAGGATGGT TC-AAAGTATT ATTTTGATGA-AGATACAGCA GAAGCATATA

6296  TAGGTTTGTC ATTAATAAAT GATGGTCAA-T ATTATTTTAA TGATGATGGA ATTATGCAAG TT-GGATTTGT CACTATAAAT GATAA-AGTCT TCTACTTCTC
      .......... .......... .........-. .......... .......... .......... ..-........ .......... .....-..... ..........
      .......... .......... .........-. .......... .......... .......... ..-........ .......... .....-..... ..........
      .....A.A.. .A....T... .....GA..-. .......... ....TC.... ..C.....A. ..-........ ...A...... A..G.-...A. .T..T.....
      .......aa. .g....t... ....t..-..g. ........g. ....a.c... ..a.g....- ..a......a. .......... ..c..t.-.a. .t..t.....
6296  TAGGTTTGTC ATTAATAAAT GATGGTCAA-T ATTATTTTAA TGATGATGCA ATTATGCAAG TT-GGATTTGT CACTATAAAT GATAA-AGTCT TCTACTTCTC
```

APPENDIX I-continued

*C. difficile* tcdB sequence

```
6396  TGACTCTGGA ATTA-TAGAAT CT-GGAGTA-CA AAACATAGAT GACAATTATT TCTATATA-GA TGATAA-TGGT ATAGTTCAAA TTGGTGTATT TGATACTTCA
      .......... ....-...... ..-......-.. .......... .......... ........-.. ......-.... .......... .......... ..........
      .......... ....-...... ..-......-.. .......... .......... ........-.. ......-.... .......... .......... ..........
      ...T...... ..-.G...... ..-...A.G-.. ...T...... ..T..C.... ........A.-. ..A..-.... C......... .......... ...C......
      ...a...... .aa.-....g. -.a...-..c.. ...t...a.. .gt..c.... ....c...... ....g.... t.....t.. ....a..... ......cc..
6396  TGACTCTGGA ATTA-TAGAAT CT-GGAGTA-CA AAACATAGAT GACAATTATT TCTATATA-GA TGATAA-TGGT ATAGTTCAAA TTGGTGTATT TGATACTTCA

6496  GATGGATATA AATATTTTGC ACCTGC-TAAT ACTGTAAATG ATAATATTTA CGGACAAGCA GTTGAATATA GTGGTTTAGT TAGAGTTGGG GAAGATGTAT
      .......... .......... ......-.... .......... .......... .......... .......... .......... .........T ..........
      .......... .......... ......-.... .......... .......... .......... .......... .......... .........T ..........
      .......... ....C..... ...A..-.... .......... .......... T......... .......... .......... .......AAT ........G.
      ..c....... .......... ....-.t.... .......... .......... t......... ...a...... .......... a..g...aat ..g..c....
6496  GATGGATATA AATATTTTGC ACCTGC-TAAT ACTGTAAATG ATAATATTTA CGGACAAGCA GTTGAATATA GTGGTTTAGT TAGAGTTGGG GAAGATGTAT

6596  ATTA-TTTTGG AGAAACATAT ACAATTGAGA CTGGATGGAT ATATGATATG- GAAAATGAAA GTGATAAATA TTATTTCAAT CCAGAAACTA AAAAAGCATG
      ....-...... .......... .......... .......... ..........- .......... .......... .......G.. .......... ..........
      ....-...... .......... .......... .......... ..........- .......... .......... .......GT. .......... ..........
      ..-.G...... ....T..... ........A. .......... .......-.CA ....T..... .......... .......G.. ......G... .........A
      ..-.G...... t......... .a.....a. ......-.-- ----....--- .......... c......... ......tg.. .....g.... .........a
6596  ATTA-TTTTGG AGAAACATAT ACAATTGAGA CTGGATGGAT ATATGATATG- GAAAATGAAA GTGATAAATA TTATTTCAAT CCAGAAACTA AAAAAGCATG

6696  CAAAGGTATT AATTTAATTG ATGATATAAA ATATTATTTT GATGAGAAGG GCATAATGAG AAC-GGGTCTT ATATCATTTG AAAATAATAA TTATTACTTT
      .......... .......... .......... .......... .......... .......... ...-....... .......... .......... ..........
      .......... .......... .......... .......... .......... .......... ...-....... .......... .......... ..........
      T.......C ...G...... .......... ...C...... ........T. .......... ...-A...... ...A...... ..G.....C. ...C..T...
      t.....c... ...g..g... .......... .........c ........t. .t........ ...a..-.... .......... .......... .........c
6696  CAAAGGTATT AATTTAATTG ATGATATAAA ATATTATTTT GATGAGAAGG GCATAATGAG AAC-GGGTCTT ATATCATTTG AAAATAATAA TTATTACTTT
```

APPENDIX I-continued

*C. difficile* tcdB sequence

```
6796  AATGA-GAATG GTGAAATGCA ATTTGGTTAT ATAAATATAG AAGATAAGAT GTTCTATTTT GGTGAAGATG GTGTCATGCA GATTGGAGTA TTTAATACAC
      .....-.... .......... .......... .......... .......... .......... .......... .......... .......... ..........
      .....-.... .......C.. .......... .......... .......... .......... .......... .......... .......... ..........
      .....A..-.. .......... ..A....... C......... .......... ......C... A......... ..A.T..... .......... ..........
      .....a..-.. ..a....... .......... c........a .......a.. ...t...... ...a...... ..aaa..... .......... ........c.
6796  AATGA-GAATG GTGAAATGCA ATTTGGTTAT ATAAATATAG AAGATAAGAT GTTCTATTTT GGTGAAGATG GTGTCATGCA GATTGGAGTA TTTAATACAC

6896  CAGATGGATT TAAATACTTT GCACATCAAA ATACTTTGGA TGAGAATTTT GAGGGAGAAT CAATAAACTA TACTGGTTGG TTAGATTTAG ATGA-AAAGAG
      .......... .......... .......... .......... .......... .......... .......... .......... .......... ....-......
      .......... .......... .......... .......... .......... .......... .......... .......... ....G..... ....-......
      .......... ......T... .......... .......A.. .......... .......... .......... .......... .......... ....-......
      .......... .......... .......... .......a.. .......... .....g.... .......... .......... .......... ...gt...-..
6896  CAGATGGATT TAAATACTTT GCACATCAAA ATACTTTGGA TGAGAATTTT GAGGGAGAAT CAATAAACTA TACTGGTTGG TTAGATTTAG ATGA-AAAGAG

6996  ATATTATTTT ACAGATGAAT ATATTGCAGC AACTGGTTCA GTT-ATTATTGATGGTGAGGA GTATTATTTT GATCCTGATA CAGCTCAATT AGT-GATTAGT
      .......... .......... .......... .......... ...-................. .......... .......... .......... ...-.......
      .......... .......... .......... .......... ...-................. .......... .......... .......... ...-.......
      .......... .......... ....C..... .......... ...-................. .......... .......... .......... ...-.......
      .......... .......... ....a..... ......c... -..g.c.........t.ca. t..c...... ..c....... .....g.... ...a.-.....
6996  ATATTATTTT ACAGATGAAT ATATTGCAGC AACTGGTTCA GTT-ATTATTGATGGTGAGGA GTATTATTTT GATCCTGATA CAGCTCAATT AGT-GATTAGT

7096  GAATAGATAA
      ..........
      ..........
      ..........
      .....
```

Note:

(1) *C. diff* strain VPI10463 (Toxinotype 0) (Gene bank = X92982) Toxin B sequence, 7101 bp (first line)

(2) *C. diff* strain 5340 ToxA−/ToxB+ (Gene Bank = AF217292) Toxin B sequence, (INFECTION AND IMMUNITY, 2000, 68 p. 5480. Sambol S. et al. Toxin gene analysis of a variant strain of *C. diff* that causes human clinical diseases)(second line)

(3) *C. diff* strain 1470 ToxA−/ToxB+ (Toxinotype VIII) (Gene Bank = Z23277) Toxin B sequence, (MOL. MICROBIOL., 1995, 17 p. 313, Von Eichel-Striber C. et al. Cloning on the Toxic domain through analysis of a variant *C. Diff* cytotoxin B) (third line)

(4) *C. diff* strain 8864 Tox A−/Tox B+ (Toxinotype X) (Gene Bank = AJ011301) Toxin B sequence (fourth line)

(5) *C. diff* strain C34 Cluster 1-2 (Gene Bank = AJ 294944) Toxin B partial sequence, (FEMS MICROBIOL. LET., 2001, 198 p. 171, Mehlig M. et al. Variant toxin B and a functional toxin A produced *C. Diff* C34). (fifth line)

(6) *C. sordellii* cytotoxin (Gene Bank = X 82638) sequence, (GENE, 1995, 161 p. 57, Green G. A. et al. Cloning and characterization of the cytotoxin L-encoding gene of *C. sordellii*: homology with *C. Diff* cytotoxin B) (sixth line)

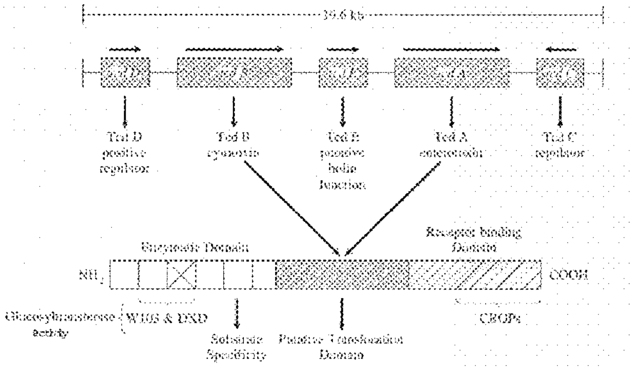

What is claimed is:

1. A method for determining the presence of a toxigenic strain of *C. difficile* in a biological sample, comprising:

contacting said sample with at least one pair of primers capable of binding to a *C. difficile* toxin B (TcdB) gene, wherein each primer in said at least one pair of primers is up to 50 nucleobases in length, and is capable of binding to a *C. difficile* toxin B (TcdB) gene, wherein said at least one pair of primers comprises a primer comprising the sequence of SEQ ID NO: 16 and a primer comprising the sequence of SEQ ID NO: 19;

amplifying target nucleic acid from said sample; and detecting the presence or amount of an amplified product (s) as an indication of the presence of said toxigenic strain of *C. difficile* in said sample.

2. The method of claim 1, wherein said sample is selected from the group consisting of stool, sputum, peripheral blood, plasma, serum, lymph nodes, respiratory tissue and exudates.

3. The method of claim 2, wherein said sample is a stool sample.

4. The method of claim 1, wherein said sample is contacted with one pair of primers.

5. The method of claim 4, wherein each primer introduces exogenous nucleotide sequence which allows post-amplification manipulation of amplification products without a significant effect on amplification itself.

6. The method of claim 4, wherein one primer in said one pair of primers comprises the sequence of SEQ ID NO: 16 and the other primer in said one pair of primers comprises the sequence of SEQ ID NO 19.

7. The method of claim 4, wherein one primer in said one pair of primers consists of the sequence of SEQ ID NO: 16 and the other primer in said one pair of primers consists of the sequence of SEQ ID NO 19.

8. The method of claim 7, wherein detecting the presence or amount of the amplified product(s) comprises contacting the amplified product(s) with an oligonucleotide probe capable of hybridizing to the amplified product(s), wherein the oligonucleotide probe comprises the sequence of SEQ ID NO: 30.

9. The method of claim 1, wherein said amplifying is carried out by a method selected from the group consisting of polymerase chain reaction (PCR), ligase chain reaction (LCR), strand displacement amplification (SDA), replicase-mediated amplification and transcription-mediated amplification.

10. The method of claim 9, wherein said amplifying is carried out using PCR.

11. The method of claim 10, wherein said PCR is selected from the group consisting of AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR.

12. The method of claim 11, wherein said PCR is quantitative real-time PCR (QRT-PCR).

13. The method of claim 1, wherein detecting the presence or amount of the amplified product(s) comprises contacting the amplified product(s) with an oligonucleotide probe capable of hybridizing to the amplified product(s).

14. The method of claim 13, wherein said oligonucleotide probe comprises a fluorophore at the 5' end, and a fluorescence quencher at the 3' end.

15. The method of claim 13, wherein the oligonucleotide probe comprises the sequence of SEQ ID NO: 30.

* * * * *

UNITED STATES PATENT AND TRADEMARK OFFICE

CERTIFICATE OF CORRECTION

PATENT NO. : 9,096,638 B2
APPLICATION NO. : 12/203694
DATED : August 4, 2015
INVENTOR(S) : Paquette et al.

It is certified that error appears in the above-identified patent and that said Letters Patent is hereby corrected as shown below:

The title page, showing the illustrative figure, should be deleted and substitute therefor the attached title page.

In column 2 (title page 2, item 56) at line 30, Under Other Publications, change "Dexcription" to --Description--.

The drawing sheet, consisting of fig. 1, should be deleted to be replaced with the drawing sheet, consisting of fig. 1, as shown on the attached page.

In the specification,

In column 2 at line 7, Change "disagreggation" to --disaggregation--.

In column 2 at line 52 (approx.), Change "no16," to --no. 16,--.

In column 3 at line 14 (approx.), Change "Rae" to --Rac--.

In column 3 at line 57 (approx.), Change "TX," to --IX,--.

In column 4 at lines 34-35 (approx.), Change "(SEQ ID NO: 1) (SEQ ID NO: 1) is are" to --(SEQ ID NO: 1) are--.

In column 6 at line 13, Change "toxogenic" to --toxigenic--.

In column 10 at line 64 (approx.), Change "0.2504" to --0.25 μM--.

In column 10 at line 65 (approx.), Change "Na+" to --$Na^+$--.

In columns 11-12 (Table 2) at line 33 (approx.), Change "ACAAAAGAAGGTTTATTTGTATG" to --ACAAAAGAAGGTTTATTTGTATC--.

In column 13 at line 65, Change "80%" to --80%.--.

In column 17 at line 13 (approx.), Change "target" to --target.--.

In column 20 at line 63 (approx.), Change "see" to --sec,--.

In column 20 at line 65 (approx.), Change "see" to --sec--.

In columns 45-46 at line 30 (approx.), Change "Eichel-Striber" to --Eichel-Streiber--.

Signed and Sealed this
Twenty-first Day of June, 2016

Michelle K. Lee

Michelle K. Lee
*Director of the United States Patent and Trademark Office*

In the claims,

In column 87 at line 50 (approx.), In Claim 6, change “SEQ ID NO 19.” to --SEQ ID NO: 19.--.

In column 87 at line 54 (approx.), In Claim 7, change “SEQ ID NO 19.” to --SEQ ID NO: 19.--.

(12) United States Patent
Paquette et al.

(10) Patent No.: US 9,096,638 B2
(45) Date of Patent: Aug. 4, 2015

(54) **DETECTION OF TOXIGENIC STRAINS OF *CLOSTRIDIUM DIFFICILE***

(75) Inventors: Nancy Paquette, Quebec (CA); Marie-Eve Rochette, Quebec (CA); Rachel Labourdette, Quebec (CA)

(73) Assignee: GENEOHM SCIENCES CANADA, INC., Quebec (CA)

(*) Notice: Subject to any disclaimer, the term of this patent is extended or adjusted under 35 U.S.C. 154(b) by 876 days.

(21) Appl. No.: 12/203,694

(22) Filed: Sep. 3, 2008

(65) Prior Publication Data

US 2009/0208948 A1 Aug. 20, 2009

Related U.S. Application Data

(60) Provisional application No. 60/970,492, filed on Sep. 6, 2007.

(51) Int. Cl.

| | |
|---|---|
| ***C12Q 1/68*** | (2006.01) |
| ***C07H 21/00*** | (2006.01) |
| *C07H 21/04* | (2006.01) |

(52) U.S. Cl.

CPC ................ *C07H 21/04* (2013.01); *C07H 21/00* (2013.01); *C12Q 1/689* (2013.01); *C12Q 2561/101* (2013.01); *C12Q 2561/113* (2013.01)

(58) Field of Classification Search

None

See application file for complete search history.

(56) References Cited

U.S. PATENT DOCUMENTS 8,114,601 B2 * 2/2012 Bergeron et al. ........... 435/6.12

FOREIGN PATENT DOCUMENTS

| | | |
|---|---|---|
| JP | 2006333785 | 12/2006 |
| WO | WO 2008/041354 | 4/2008 |

OTHER PUBLICATIONS

GenBank Accession No. X53138, Barroso et al, "*Clostridium difficile* toxB gene for toxin B," Apr. 2005.*

GenBank Accession No. AJ011301, Kohl. "*Clostridium difficile* (strain 8864) pathogenicity DNA locus,"Jan. 2001.*

GenBank Accession No. Z23277, von Eichel-Streiber et al, "*C. difficile* gene for toxin B," Apr. 2005.*

Plant-Microbe Genomics Facility (PMGF) at the Ohio State University, "Procedures and Recommendations for Quantitative PCR," version 1.2, Apr. 2003.*

Abed. Y. et al. World Journal of Microbiology & Biotechnology 11(5):478-480 (Sep. 1995).*

Belanger, S.D. et al. Rapid detection of *Clostridium difficile* in Feces by RealTime PCR. Journal of Clinical Microbiology. Feb. 2003. vol. 41, No. 2. pp. 730-734, ISSN 0095-1137.

Van Den Berg, RJ. et al. Rapid diagnosis of toxinogenic *Clostridium difficile* in faecal samples with internally controlled real-time PCR. Clinical Microbiology and Infection. Feb. 2006, vol. 12. No. 2, pp. 184-186. ISSN 1198-743X.

(Continued)

*Primary Examiner* — Diana B Johannsen

(74) *Attorney, Agent, or Firm* — Knobbe, Martens, Olson & Bear LLP

(57) ABSTRACT

Primers and probes for detection of toxin-producing (toxigenic) strains of *Clostridium difficile*, and to methods of detecting toxigenic strains using these primers and probes. Toxigenic strains of *C. difficile* are detected by nucleic acid-based amplification methods using particular primers and probes that bind to the toxin B (TcdB) gene. These primers and probes are used to amplify *C. difficile* nucleic acids in clinical samples to determine the presence of these toxigenic strains.

15 Claims, 3 Drawing Sheets